(12) United States Patent
Adey et al.

(10) Patent No.: US 10,876,933 B2
(45) Date of Patent: Dec. 29, 2020

(54) AUTOMATED TISSUE DISSECTION INSTRUMENT AND METHODS OF USING THE SAME

(71) Applicants: Ventana Medical Systems, Inc., Tucson, AZ (US); Roche Sequencing Solutions, Inc., Pleasanton, CA (US)

(72) Inventors: Nils B. Adey, Salt Lake City, UT (US); Dale B. Emery, Salt Lake City, UT (US); Leonid Fomin, Santa Clara, CA (US); Rene M. Guerrero, Alameda, CA (US); Emmanuel Naouri, Livermore, CA (US); Robert J. Parry, Park City, UT (US); Peter Romanowich, San Jose, CA (US)

(73) Assignees: VENTANA MEDICAL SYSTEMS, INC., Tucson, AZ (US); ROCHE SEQUENCING SOLUTIONS, INC., Pleasanton, CA (US)

( * ) Notice: Subject to any disclaimer, the term of this patent is extended or adjusted under 35 U.S.C. 154(b) by 55 days.

(21) Appl. No.: 15/807,500

(22) Filed: Nov. 8, 2017

(65) Prior Publication Data
US 2018/0128714 A1    May 10, 2018

Related U.S. Application Data

(60) Provisional application No. 62/419,948, filed on Nov. 9, 2016.

(51) Int. Cl.
*G01N 1/06* (2006.01)
*G01N 1/04* (2006.01)
(Continued)

(52) U.S. Cl.
CPC ............... *G01N 1/06* (2013.01); *G01N 1/04* (2013.01); *G01N 1/286* (2013.01); *G05B 15/02* (2013.01);
(Continued)

(58) Field of Classification Search
CPC  G01N 1/06; G01N 1/286; G01N 1/04; G01N 33/4833; G01N 2001/383;
(Continued)

(56) References Cited

U.S. PATENT DOCUMENTS

| 281,695 A | 7/1883 | Holcombe et al. |
|---|---|---|
| 3,238,889 A | 3/1966 | Huber et al. |

(Continued)

FOREIGN PATENT DOCUMENTS

| AU | 2002233157 A1 | 7/2002 |
|---|---|---|
| CN | 101018502 A | 8/2007 |

(Continued)

OTHER PUBLICATIONS

Adey, N. et al., A mill based instrument and software system for dissecting slide-mounted tissue that provides digita guidance and documentation, BMC Clinical Pathology, (2013), p. 29, vol. 13 No. 1.

(Continued)

*Primary Examiner* — Randy W Gibson
*Assistant Examiner* — Gedeon M Kidanu
(74) *Attorney, Agent, or Firm* — Charney IP Law LLC; Thomas M. Finetti

(57) ABSTRACT

A system, an instrument, a computer-implemented method, and a clinical workflow for mesodissection of biological specimens on tissue slides by incorporating annotations. An image of an annotated reference slide is acquired and transposed onto a plurality of serial samples on the tissue slides along with the corresponding annotations and meta- (Continued)

data. The serial samples are milled based on the annotations, and the milled tissue is automatically collected along with a milling buffer solution inside milling tips, and then dispensed in designated collection vials. The instrument automates the filling of aqueous buffer inside the milling tips and the monitoring of the buffer solution and the sequential filling of the milling tips. The workflow provides an integrated interface that performs tissue annotation, alignment, dissection, tracking, and reporting on a single screen. The degree of precision, ease of use and repeatability will improve PCR and NGS test results, ultimately providing timely patient results.

20 Claims, 46 Drawing Sheets

(51) Int. Cl.
*G01N 1/28* (2006.01)
*G05B 15/02* (2006.01)
*G01N 1/38* (2006.01)
*G01N 33/483* (2006.01)

(52) U.S. Cl.
CPC ... *G01N 33/4833* (2013.01); *G01N 2001/061* (2013.01); *G01N 2001/383* (2013.01)

(58) Field of Classification Search
CPC ............. G01N 2001/061; G05B 15/02; G01G 11/003; G01G 17/04; G01G 17/06
See application file for complete search history.

(56) References Cited

U.S. PATENT DOCUMENTS

| | | | |
|---|---|---|---|
| 3,732,858 A | 5/1973 | Banko | |
| 4,320,761 A | 3/1982 | Haddad | |
| 4,679,446 A | 7/1987 | Sheehan et al. | |
| 5,218,645 A | 6/1993 | Bacus | |
| 5,428,690 A | 6/1995 | Bacus et al. | |
| 5,456,125 A | 10/1995 | Gagne | |
| 5,511,556 A | 4/1996 | Desantis | |
| 5,817,955 A | 10/1998 | Gherson et al. | |
| 5,843,644 A | 12/1998 | Liotta et al. | |
| 5,843,657 A | 12/1998 | Liotta et al. | |
| 5,925,834 A | 7/1999 | Sgourakes | |
| 6,010,888 A | 1/2000 | Liotta et al. | |
| 6,135,946 A | 10/2000 | Konen et al. | |
| 6,161,442 A | 12/2000 | Sgourakes | |
| 6,204,030 B1 | 3/2001 | Liotta et al. | |
| 6,251,516 B1 | 6/2001 | Bonner et al. | |
| 6,342,143 B1 | 1/2002 | Minden | |
| 6,565,728 B1 | 5/2003 | Okagaki | |
| 6,602,071 B1 | 8/2003 | Ellion | |
| 6,673,086 B1* | 1/2004 | Hofmeier ............... C12M 45/02 606/169 |
| 6,684,720 B2 | 2/2004 | Sgourakes | |
| 6,702,990 B1 | 3/2004 | Camacho et al. | |
| 7,093,508 B2 | 8/2006 | Harris | |
| 7,185,551 B2 | 3/2007 | Schwartz | |
| 7,473,401 B1 | 1/2009 | Baer | |
| 7,482,169 B2 | 1/2009 | Gjerde et al. | |
| 7,673,531 B2 | 3/2010 | May et al. | |
| 7,794,664 B2 | 9/2010 | Pelletier et al. | |
| 7,803,634 B2 | 9/2010 | Klimov et al. | |
| 7,883,666 B2* | 2/2011 | Ting ....................... G01N 1/286 422/538 |
| 7,907,259 B2 | 3/2011 | Sagmuller et al. | |
| 8,293,497 B2 | 10/2012 | Schutze | |
| 8,431,078 B2 | 4/2013 | Schutze et al. | |
| 8,545,517 B2 | 10/2013 | Bodduluri et al. | |
| 8,668,872 B2 | 3/2014 | Klimov et al. | |
| 8,870,788 B2 | 10/2014 | Shimizu et al. | |
| 9,028,757 B2 | 5/2015 | Klimov et al. | |
| 9,101,351 B2 | 8/2015 | Thompson et al. | |
| 9,200,989 B2 | 12/2015 | Niehren | |
| 9,547,898 B2 | 1/2017 | Hall et al. | |
| 2002/0091441 A1 | 7/2002 | Guzik | |
| 2002/0108857 A1 | 8/2002 | Paschetto | |
| 2002/0134175 A1 | 9/2002 | Mehra | |
| 2003/0179916 A1 | 9/2003 | Magnuson | |
| 2004/0053326 A1 | 3/2004 | Emmert-Buck | |
| 2004/0142488 A1 | 7/2004 | Gierde | |
| 2005/0042692 A1 | 2/2005 | Star et al. | |
| 2005/0175511 A1 | 8/2005 | Cote | |
| 2005/0250211 A1 | 11/2005 | Reinhardt et al. | |
| 2006/0074346 A1 | 4/2006 | Hibner | |
| 2006/0243110 A1 | 11/2006 | Ostermann et al. | |
| 2007/0086917 A1 | 4/2007 | Lemme | |
| 2007/0271179 A1 | 11/2007 | Kubota | |
| 2008/0019878 A1 | 1/2008 | Trump | |
| 2008/0148913 A1 | 6/2008 | Chen | |
| 2008/0161842 A1* | 7/2008 | Ting ....................... G01N 1/286 606/167 |
| 2008/0235055 A1 | 9/2008 | Mattingly et al. | |
| 2010/0000383 A1 | 1/2010 | Koos | |
| 2010/0145326 A1 | 6/2010 | Hoey | |
| 2011/0104642 A1* | 5/2011 | Luksch ............... A61C 13/081 433/201.1 |
| 2012/0045790 A1 | 2/2012 | Van Dijk | |
| 2013/0344500 A1 | 12/2013 | Trautman | |
| 2014/0098214 A1 | 4/2014 | Schlaudraff et al. | |
| 2014/0329269 A1* | 11/2014 | Adey ....................... G01N 1/04 435/30 |
| 2014/0348410 A1 | 11/2014 | Grunkin | |
| 2014/0356876 A1 | 12/2014 | Ragan | |
| 2015/0316478 A1 | 11/2015 | Klimov et al. | |
| 2016/0116729 A1 | 4/2016 | Casas | |
| 2017/0322124 A1* | 11/2017 | Barnes ..................... G01N 1/286 |
| 2017/0328817 A1* | 11/2017 | Barnes ..................... G06T 7/33 |
| 2018/0025210 A1 | 1/2018 | Remiszewski | |
| 2018/0149561 A1 | 5/2018 | Schlaudraff | |
| 2018/0340870 A1 | 11/2018 | Gustafson | |

FOREIGN PATENT DOCUMENTS

| | | |
|---|---|---|
| CN | 101267546 A | 9/2008 |
| CN | 201262598 Y | 6/2009 |
| CN | 101543413 A | 9/2009 |
| CN | 103384818 A | 11/2013 |
| CN | 103443609 B | 1/2016 |
| DE | 19818425 A1 | 7/1999 |
| EP | 1067374 B1 | 3/2013 |
| EP | 1969340 B1 | 7/2019 |
| JP | S62292144 A | 12/1987 |
| JP | H07184908 A | 7/1995 |
| JP | 2001500772 A | 1/2001 |
| JP | 2001041864 A | 2/2001 |
| JP | 2004069666 A | 3/2004 |
| JP | 2004258017 A | 9/2004 |
| JP | 2006506672 A | 2/2006 |
| JP | 2006518654 A | 8/2006 |
| JP | 2007209360 A | 8/2007 |
| JP | 2007286697 A | 11/2007 |
| JP | 2009103701 A | 5/2009 |
| JP | 2010267092 A | 11/2010 |
| JP | 2012198234 A | 10/2012 |
| JP | 2013506835 A | 2/2013 |
| JP | 5215969 B2 | 6/2013 |
| JP | 2013178825 A | 9/2013 |
| JP | 2013195133 A | 9/2013 |
| JP | 2013245988 A | 12/2013 |
| JP | 2013245998 A | 12/2013 |
| JP | 2014504728 A | 2/2014 |
| KR | 100271053 B1 | 11/2000 |
| KR | 20020085123 A | 11/2002 |
| KR | 20050027607 A | 3/2005 |
| KR | 20050027609 A | 3/2005 |
| WO | 2000057153 A1 | 9/2000 |
| WO | 2002037159 A2 | 5/2002 |
| WO | 2002057746 A2 | 7/2002 |
| WO | 2004045768 A1 | 6/2004 |

(56) References Cited

FOREIGN PATENT DOCUMENTS

| WO | 2006011510 A1 | 2/2006 |
|---|---|---|
| WO | 2006123967 A2 | 11/2006 |
| WO | 2007076934 A1 | 7/2007 |
| WO | 2008156566 A1 | 12/2008 |
| WO | 2009008843 A1 | 1/2009 |
| WO | 2010093861 A2 | 8/2010 |
| WO | 2010125495 A2 | 11/2010 |
| WO | 2012102779 A2 | 8/2012 |
| WO | 2012115948 A1 | 8/2012 |
| WO | 2012102779 A3 | 9/2012 |
| WO | 2014140070 A2 | 9/2014 |
| WO | 2014140070 A3 | 11/2014 |
| WO | 2016120433 A1 | 8/2016 |
| WO | 2020057746 A1 | 3/2020 |

OTHER PUBLICATIONS

International Search Report and Written Opinion dated Feb. 9, 2018 in corresponding PCT/EP2017/078623 filed Nov. 8, 2017, pp. 1-13.
Suarez-Quian et al., "Laser Capture Microdissection: A New Tool for the Study of Spermatogenesis," Journal of Andrology, vol. 21, No. 5, Sep./Oct. 2000.
Walker et al., "Quantitative PCR for DNA identification absed on genome-specific interspersed repetitive elements," Genomics 83 (2004) 518-527.
Moelans et al., "HER-2/neu amplification testing in breast cancer by Multiplex Ligation-dependent Probe Amplification: Influence of manual- and laser microdissection," BMC Cancer 2009, 9:4.
Adey, N. et al.; "A mill based instrument and software system for dissecting slide-mounted tissue that provides digital guidance and documenation" BMC Clinical Pathology, (2013) p. 29; vol. 13 No. 1.
Beltinger et al.; A simple combined microdissection and aspiration device for the rapid procurement of single cells from clinical peripheral blood smears; Molecular Pathology; 1998; pp. 233-236; vol. 51.
De Bruin et al; Macrodissection versus microdissection of rectal carcinoma: minor influence of stroma cells to tumor cell gene expression profiles; BMC Genomics; Oct. 14, 2005; 10 pages; vol. 6, No. 142; BioMed Central.
Extended European search report issued Aug. 29, 2017, in EP Application No. EP 11 85 7029, filed Nov. 16, 2011, 11 pages.
Going et al.; Practical histological microdissection for PCR analysis; The Journal of Pathology; May 1996; pp. 121-124; vol. 179, Issue 1; John Wiley & Sons, Ltd.
Going; Histological microdissection in diagnostic and investigative pathology; Diagnostic Histopathology; Jan. 2010; pp. 43-48; vol. 16, Issue 1; Elsevier.
Hernandez et al.; Manual versus laser micro-dissection in molecular biology; Ultrastructural Pathology; 2006; pp. 221-228; vol. 30, No. 3; Informa Healthcare.

http://en.nanotec.com/hollowshaft_steppermotors.html.
http://www.andrologyjournal.org/cgi/reprint/21/5/601.pdf.
http://www.dell.com/us/p/inspiron-mini1018/pd?refid+inspiron-1018&s=dhs&cs=19.
http://www.dino-lite.com.
http://www.etaluma.com/Index.php.
http://www.griffinmotion.com/product-detail.asp?productid=20.
http://www.micromark.com/MicroLux-Micro-Milling-Machine.9683.html.
http://www.ncbi.nlm.nih.gov/pmc/articles/PMC2631004.
http://www.ncbi.nlm.nih.gov/pubmed/_12711348.
http://www.rolynoptics.thomasnet.com/item/d-microscope-sections-microscope-stages-and-mounts//mechanical-stage/80/5166-id-1769-?.
International Search Report and Written Opinion dated Jan. 26, 2016 in corresponding PCT/EP2016/051895 filed on Jan. 29, 2016, pp. 1-11.
International Search Report and Written Opinion dated Feb. 9, 2018 in corresponding PCT/EP2017/078623 filed on Nov. 8, 2017, pp. 1-13.
International Search Report and Written Opinion, dated May 2, 2016 for PCT/EP2016/051894.
Japanese office action dated Aug. 23, 2018 in corresponding Japanese patent application No. 2017-539656.
Lee et al.; A simple, precise and economical microdissection technique for analysis of genomic DNA from archival tissue sections; Oct. 1998; pp. 305-309; vol. 433, Issue 4; Springer-Verlag.
Linton et al.; Preparation of formalin-fixed paraffin-embedded (FFPE) tissue for RNA extraction; BioTechniques; Nov. 2009; p. 54;.
Martin et al.; Differences in the Tumor Microenvironment between African-American and European-American Breast Cancer Patients; PLoS One; Feb. 2009; 14 pages; vol. 4, Issue 2; www.plosone.org.
Office Action for Chinese application 201180069499.6 dated Jul. 10, 2015, 6 pages including English Translation.
Office Action for Chinese application 201180069499.6 dated Oct. 10, 2015, 4 pages including English Translation.
Office Action for Chinese application 201180069499.6 dated Oct. 20, 2014, 20 pages including English Translation.
PCT Application PCT/US2011/061075; Filing date Nov. 16, 2011; Adey Nils B et al.; International Search Report dated Jul. 18, 2012.
Quistorff et al.; Simple Techniques for Freeze Clamping and for Cutting and Milling of Frozen Tissue at Low Temperature for the Purpose of Two- or Three-Dimensional Metabolic Studies in Vivo; Analytical Biochemistry; 1980; pp. 237-248; vol. 108; Academic Press, Inc.
Sarkar et al.; "A Robust Method for Inter-Marker Whole Slide Registration of Digital Pathology Images Using Lines Based Features" 11th International Symposium on Biomedical Imaging; Jul. 31, 2014.
Walker, et al.: Quantatative PCR for DNA identification based on genome-specific interspersed repetitive elements; Genomics; 2004; pp. 518-527; vol. 83; Elsevier.

* cited by examiner

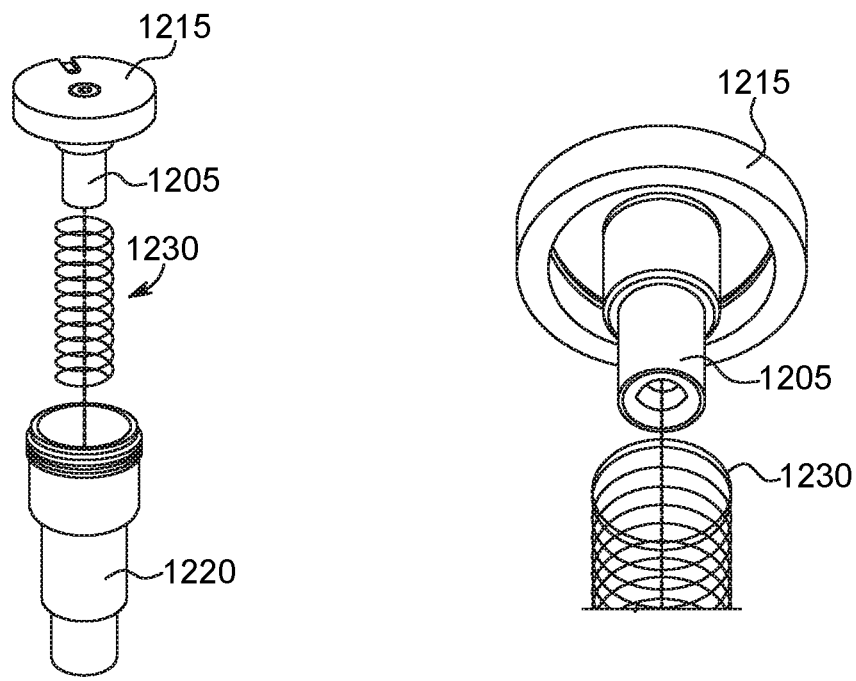
FIG. 12F
FIG. 12G
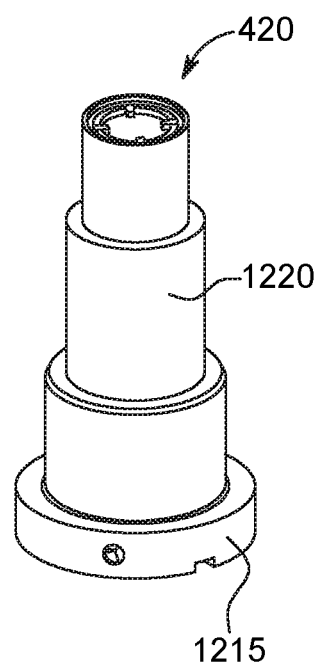
FIG. 12H

« RETURN TO CASE LIST

CASE INFO
ACCESSION NUMBER
SP14-002123B
PATHOLOGIST
GORDON, K.

PATIENT NAME
PRATT, W.

REQUEST SITE
VENTANA TUCSON

DATE OF BIRTH
11-23-1980

NOTES
Need to extract 400 m³ for all 8 slides and ma...

GENDER
M

REFERENCE IMAGE

IMPORT REFERENCE

If a digital reference is not available, leave this field blank

SAMPLE INFO
TARGET VOLUME
000 mm³ — 2620

TISSUE TYPE
Choose

TISSUE THICKNESS
μm

DOWNSTREAM APPLICATION

Add +
☑ PCR
☑ NGS
☐ NEXTGEN SEQ
☐ OTHER

PCR ×  NGS ×  HER ×

NOTES
ADD NOTES HERE — 2630

CONTINUE

◆ SAMPLE ━━━ ◆ REFERENCE ━━━

Stage Setup

| POSITION 1 | GROUP 1 | POSITION 2 |

Milling Tip             Milling Tip

Milling Tip Size        Milling Tip Size
250 μm
Milling Tip Lot         Milling Tip Lot
Number                  Number Collection Vial         NOT REQUIRED
                        Collection Vial
← 410

Vial Accession Numb     Vial Accession Numb
Enter Here              Enter Here

DISSECTION FLUID TYPE   DISSECTION FLUID LOT NUMBER    DISSECTION FLUID LEVEL

☐ Manual Workflow    ( DISSECT )

AUTOMATED TISSUE DISSECTION INSTRUMENT AND METHODS OF USING THE SAME

CROSS-REFERENCE TO RELATED APPLICATIONS

This patent application is based on and claims priority to U.S. Provisional Application No. 62/419,948, filed Nov. 9, 2016, which is incorporated herein by reference as if set forth in its entirety.

TECHNICAL FIELD

The present disclosure generally relates to a tissue dissection instrument that hosts an automated workflow for providing a tissue dissection platform and a method of using the same. More particularly, the present platform provides, among other things, precise, automated, quantifiable, and serial microdissection (mesodissection) of slide-mounted biological specimens for use in molecular or genomic analysis.

BACKGROUND

Biological specimens such as tissue sections, blood, cell cultures, and like biological samples, are mounted on a slide, stained with one or more combinations of stain and biomarkers, and the resulting assay is imaged for further analysis of the content of the specimens using a digital pathology system. Moreover, either stained or unstained paraffin embedded tissue sections may be dissected for further molecular or genomic analysis.

Clinical laboratories conventionally utilize either manual dissection using a blade, laser dissection, or mesodissection. The manual process is very rudimentary and substantially relies on the user to visually align a reference slide, such as a formalin-fixed, paraffin-embedded (FFPE) slide and to use a scalpel to ablate the tissue section. Other manual means include taking "curls" or large tissue sections directly from a FFPE block of tissue. These manual dissection methods often lack resolution in light of tissue heterogeneity, process traceability, and documentation.

While laser microdissection methods were developed to address lack of resolution, the laser-based ablation instruments are relatively expensive, labor intensive, and often rely on special slides or photoactivation films. An exemplary laser microdissection method is described in U.S. Pat. No. 7,907,259.

Mesodissection systems provide better precision than manual methods, and less expensive than laser methods, while also providing digital image guidance and electronic process documentation. An exemplary mesodissection system is described in U.S. patent application, publication No. 20140329269, titled "Devices, Systems, And Methods For Extracting A Material From A Material Sample," which is incorporated herein in its entirety by this reference. Another mesodissection system is described in patent application WO2016120433 A1. While the mesodissection systems may provide suitable results, there still remains room for improvements.

It is anticipated that tissue dissection platforms will become widely adapted in analyzing biological specimens for therapeutic, prognostic, or diagnostic decision support. As a result, what is needed is an efficient tissue dissection platform that provides precise, automated, quantifiable, and serial microdissection of slide-mounted biological specimen.

SUMMARY

The present disclosure addresses the above-identified concerns and provides additional improvements by providing a system, an instrument, a computer-implemented method of operation, and a clinical workflow for mesodissection of biological specimens on tissue slides.

In some embodiments, an image of an annotated reference slide is acquired and transposed onto a plurality of serial samples along with the corresponding annotations and metadata. The serial samples are dissected based on the annotations, and the milled tissue is automatically collected along with a milling buffer solution inside milling tips, and then dispensed in designated collection vials. The instrument automates the filling of aqueous buffer inside the milling tips and the monitoring of the buffer solution and the serial filling of the milling tips.

In some embodiments, the workflow provides an integrated interface that performs tissue annotation, alignment, dissection, tracking, and reporting on a single screen. The degree of precision, ease of use, and repeatability will improve PCR or NGS test results, ultimately providing timely patient results.

To accomplish the foregoing tasks, in some embodiments the instrument is provided with a base, a stage, a fill station, a backdrop assembly, and a head assembly. In operation, instead of filling the milling tips manually, the instrument automates the filling and unloading of the milling tip into a collection vial. An equal number of milling tips and collection vials can be concurrently loaded onto the stage. The instrument can monitor and report on all the collection vials, as well as the area and volume collected of the buffer solution and excised tissue fragments.

In some embodiments, the instrument and the workflow provide the user with the ability to control all aspects of the dissection process to include, for example:

Selecting the areas of interest to dissect. The workflow permits the user to input the tissue thickness and nucleic density of the tissue samples. With this input, the workflow can actively monitor how much volume or nucleic concentration is collected, and can alert the user when the minimum amount of buffer solution is collected based on the user's predetermined preferences. The user also has the ability to redraw the areas of interest.

Viewing in real time the reference and serial cut selection.

Dissecting across multiple serial selections at one time.

Changing the lighting conditions, focus, and iris, in order to identify and compare key cellular tissue sections on a slide.

In some embodiments, the workflow enables full automation of the annotations, dissection, and sample collection steps. As an example, four different areas of interest can be dispensed into four separate collection vials. Once the user has the areas of interest marked on the system, the user can press the "Dissect" key to let the workflow complete the remaining process without any significant input from the user.

To this end, once the milling tips and collection vials are loaded onto the stage, and the user presses the "Dissect" key, the instrument can automatically pick up the first milling tip at the tip holder and move the tip to the camera. In some embodiments, the workflow uses a color recognition algorithm to determine if the correct milling tips and collection vials have been loaded, in terms of presence and size. While previous methods typically "eyeball" the presence of the loaded milling tips, the present instrument provides a camera to visually verify the sizes and presence of the milling tips and the collection vials in the correct positions on the stage, through color recognition. This feature ensures that the samples can be collected reliably throughout the process.

In some embodiments, the user can use different buffer solutions for the extraction process, allowing the user to closely integrate the dissection process with a downstream tissue extraction process, thus reducing the number of steps and improving the tissue extraction times. The workflow enables the user to verify that the dissection buffer solution was collected using color recognition.

In some embodiments, the fill station allows the user to fill a single receptacle that is used to automatically fill buffer solution in the milling tip through the automation process. The fill station is electronically monitored to determine if enough liquid is available for dissection.

In some embodiments, the instrument and workflow offer numerous other features, among which are the following:

Providing flexible weight settings based on tissue types and an integrated software workflow.

Two barcode readers, one located on the head assembly to read the slide barcodes, and a hand-held barcode reader to read barcode information from the collection vials and the milling tips. The camera can, for example, acquire an image of the reference slide with the barcode reader on the head assembly.

The alignment of the serial sample slides with the reference slide is done through a backdrop assembly that is controlled by the user. The backdrop assembly optimizes the contrast of the reference slide image, by selecting the correct backdrop (e.g., white, silver, black, or having any other color) based on the type of sample slides on the stage.

An automatic tip pressure actuator allows the user to adjust the amount of tip pressure based on the tissue type and the milling tip type. The end result is that the instrument consistently dissects samples across various sample types and milling tips.

At the completion of the milling (dissection or excision) process, the user is provided with a clinical report that provides the user with full traceability of the operator, buffers used, sample collection history, and user notes. The data can be linked to a hospital LIS for downstream data review.

BRIEF DESCRIPTION OF THE DRAWINGS

The various features of the present disclosure and the manner of attaining them will be described in greater detail with reference to the following description, claims, and drawings wherein:

FIGS. 5 through 16 depict certain components of the stage of FIG. 4, according to an exemplary embodiment of the present disclosure, wherein:

FIG. 5 depicts a tray;

FIG. 6 depicts an assembly view of a load cell block and the tray of FIG. 5;

FIG. 7 depicts the load cell block assembled to the tray of FIG. 6;

FIG. 8 depicts an assembly view of the tray with the embedded load cell block, a bottom slide frame, a glass window, and a top slide frame;

FIG. 9 depicts a top view of the top slide frame of FIG. 8, further illustrating a calibration grid secured thereto, as well as a fill station opening;

FIG. 10 depicts the assembled view of the components shown in FIG. 8, in addition to a slide clamp spring assembly;

FIG. 11 depicts the assembled view of the components shown in FIG. 10, in addition to a slide clamp cover;

FIGS. 12A, 12B, 12C, 12D, 12E, 12F, 12G, depict sequential assembly views of a milling tip holder assembly;

FIG. 12H depicts an isometric view of an assembled milling tip holder;

FIG. 13 depicts the stage provided with four milling tip holders, with a load cell block shown accessible through the top slide frame;

FIG. 14 depicts a reservoir riser being secured to the assembled load cell block of FIG. 13;

FIG. 16 depicts an assembly view of the components illustrated in FIG. 14, as well as the support platform of FIG. 15A and FIG. 1B;

FIG. 26 illustrates an exemplary screen shot associated with an "Instrument Setup" step of the workflow of FIG. 25, according to an exemplary embodiment of the present disclosure;

FIG. 28 represents another exemplary screen shot associated with the stage overview step of the workflow of FIG. 25, for a monitoring and collecting dashboard according to an exemplary embodiment of the present disclosure;

FIG. 39 represents a screen shot of the final report that is prepared according to an exemplary embodiment of the present disclosure;

DETAILED DESCRIPTION

Tissue Dissection Instrument 100

Figure 1:
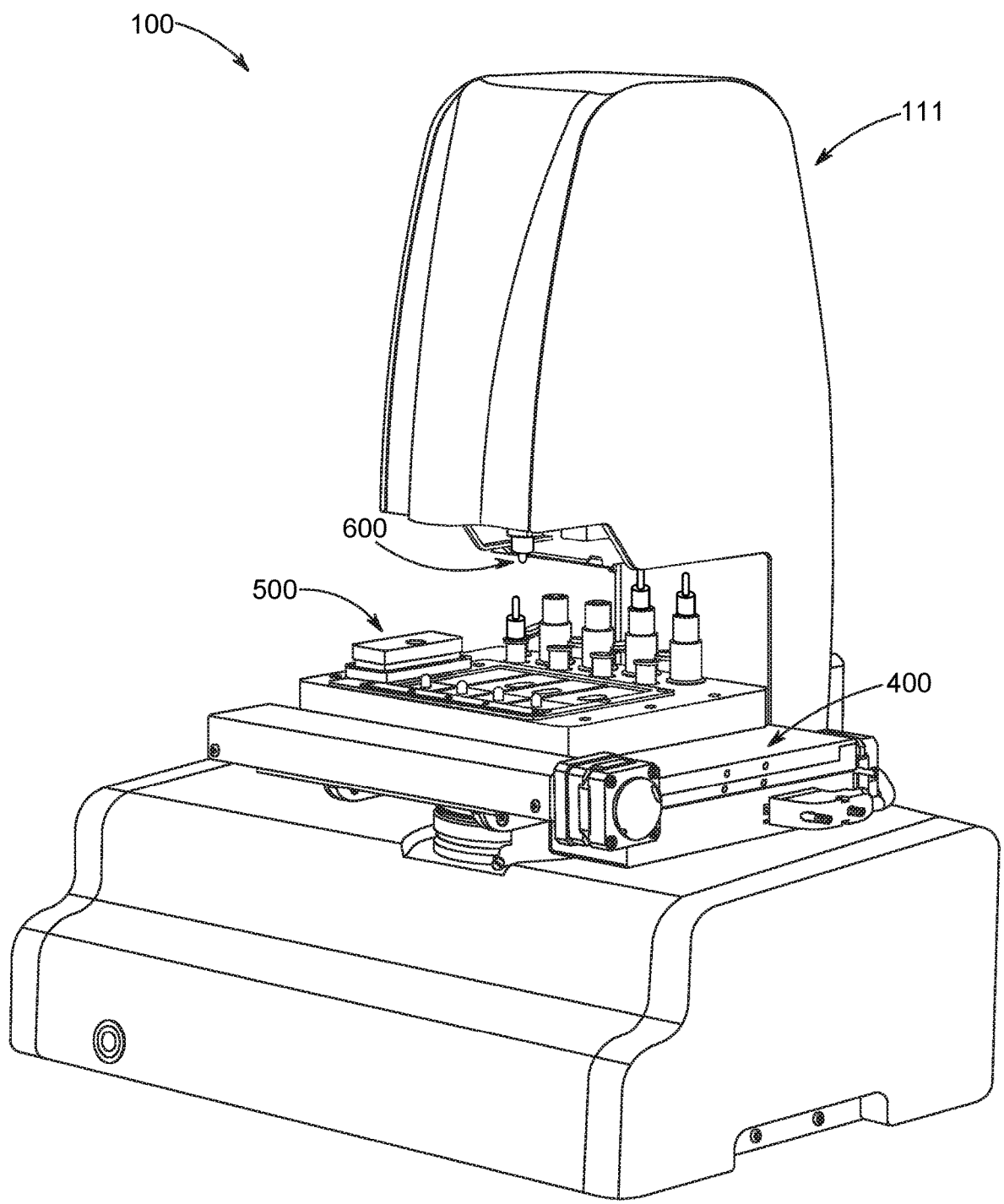
FIG. 1 depicts a computer-based tissue dissection instrument that hosts a workflow residing on a workflow module, for providing a tissue dissection platform, in accordance with an exemplary embodiment of the present disclosure.

FIG. 1 depicts an exemplary computer-based tissue dissection instrument (or system) 100, an exemplary computer-implemented method, and an exemplary clinical workflow residing on a workflow module 320 (FIG. 3), for meso-dissection of biological specimens and tissue slides in accordance with the present disclosure. Alternatively, a separate computer and monitor can be used. As used herein, the term "tissue" encompasses various types of biological specimens such as tissue sections, blood, cell cultures, and like biological samples, that can be mounted on a slide.

In use, the workflow of the instrument 100 is an integrated, single user interface workflow that provides the user with the ability to accurately and precisely create digital annotations, transfer annotations from a reference slide, to a plurality of serially dissected tissues that are mounted on slides, to perform dissections at a high precision level. The degree of precision, ease of use, and repeatability will improve PCR or NGS test results, ultimately providing more accurate and timely patient reports.

The instrument 100 automates the consecutive filling and unloading of a plurality of milling tips to corresponding sample collection vials. In one embodiment, four milling tips and four collection vials can be concurrently loaded into the instrument 100. The instrument 100 further provides an extended sample tracking feature. In one embodiment, the instrument 100 can monitor and report on the type, area, and volume of the collected tissues in the vials, as well as the type of reagents and buffer solutions used.

According to some embodiments, the user can load four slides that can be reviewed and annotated against a reference slide at one time. While the conventional laser capture systems and manual method do not allow transferring and recording annotations on more than a single slide, the present instrument 100 enables the user to perform these tasks on a single platform and for multiple slides.

Furthermore, the present disclosure can enable the user to control all aspects of the dissection process, including: the selection of the areas of interest to dissect; the real time viewing of the reference and serial cut selection; the dissection across multiple serial selections at one time; and changing the lighting conditions, focus, iris to identify and compare key cellular tissue sections on a slide.

Yet another advantage of the present instrument 100 is that it provides full automation of the annotations, dissection, and sample collection of different areas of interest into a plurality of separate milling tips. Once the user marks the areas of interest on the slides, the user can press a "Dissect" key and the instrument 100 will automatically perform the remainder of the tasks. More specially, the instrument 100 will dissect the marked areas of interest, and discharge the collected samples into distinct collection vials.

In addition, the users can use their buffer solution for the extraction process, allowing the users to closely integrate the dissection process with their downstream tissue extraction process, thus reducing the number of steps and improving the tissue extraction times. The users can choose the buffer solutions from a large spectrum of aqueous solutions and mineral oils.

Upon completion of the sample collection process, the instrument 100 can generate an integrated diagnostic report, which provides the user with full traceability of the operator, buffer solutions used, sample collection history, and user notes. The data can be linked to the hospital laboratory information system ("LIS") for downstream data review.

Figure 2:
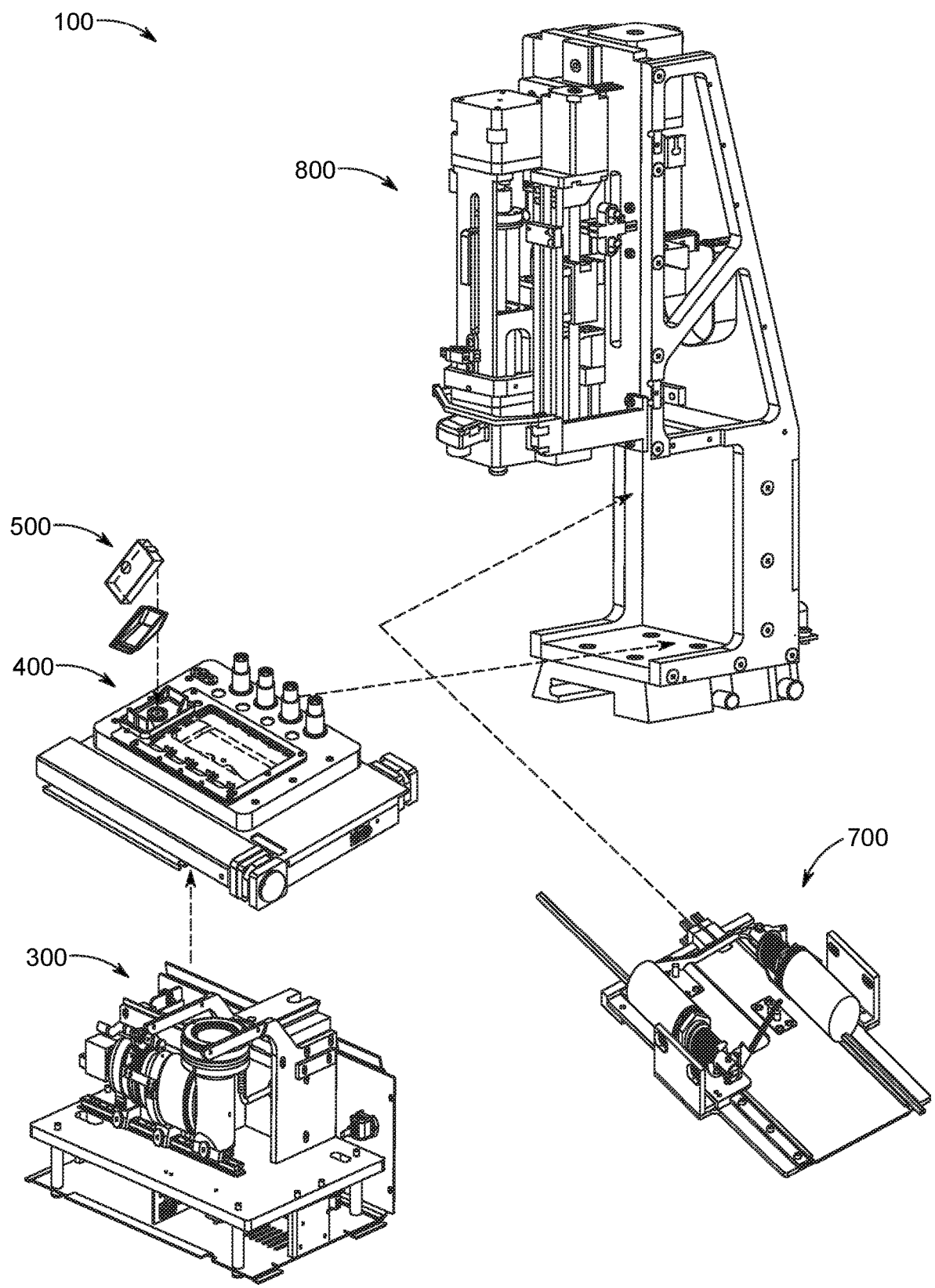
FIG. 2 depicts an assembly view of the tissue dissection instrument of FIG. 1, which includes a base, a stage, a head assembly, a fill station, and a backdrop assembly, according to an exemplary embodiment of the present disclosure.
Figure 18:
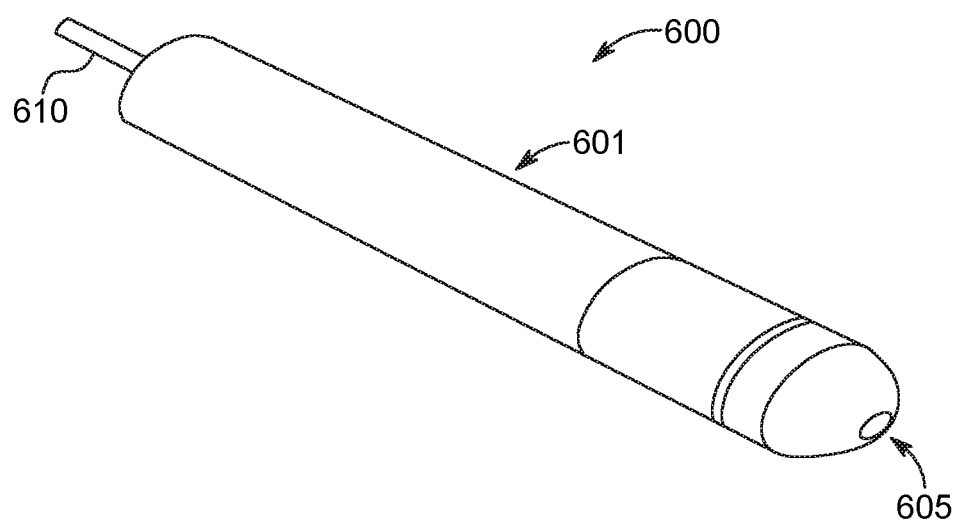
FIG. 18 depicts an isometric view of a milling tip for use in the tissue dissection instrument, according to an exemplary embodiment of the present disclosure.
Figure 19:
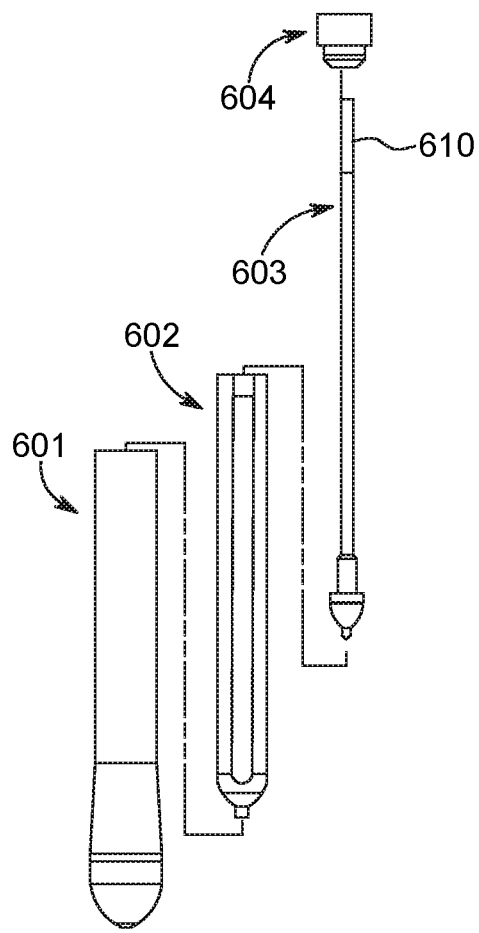
FIG. 19 depicts an assembly view of the milling tip of FIG. 18, illustrating an outer barrel, a reservoir, a plunger, and a seal, according to an exemplary embodiment of the present disclosure.
Figure 20A:
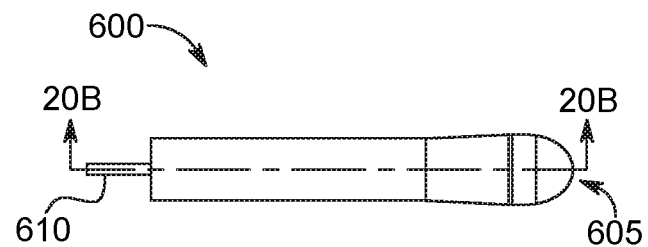
FIG. 20A depicts a side view of the milling tip of FIG. 18.
Figure 20B:
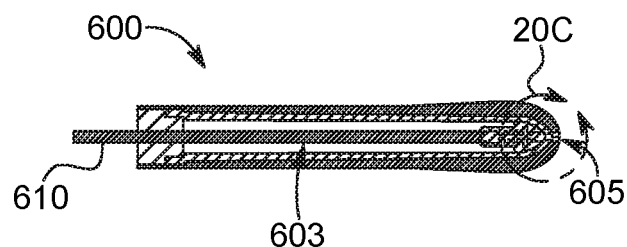
FIG. 20B depicts a cross-sectional view of the milling tip of FIG. 20A, taken along axial line 20B-20B.
Figure 20C:
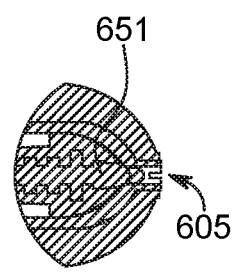
FIG. 20C depicts an enlarged view of a forwardmost portion of the milling tip of FIG. 20B.
Figure 20D:
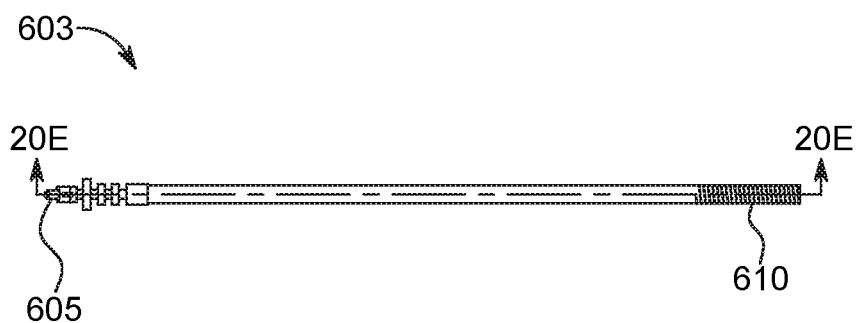
FIG. 20D depicts a side view of the plunger of FIG. 19, according to an exemplary embodiment of the present disclosure.
Figure 20E:
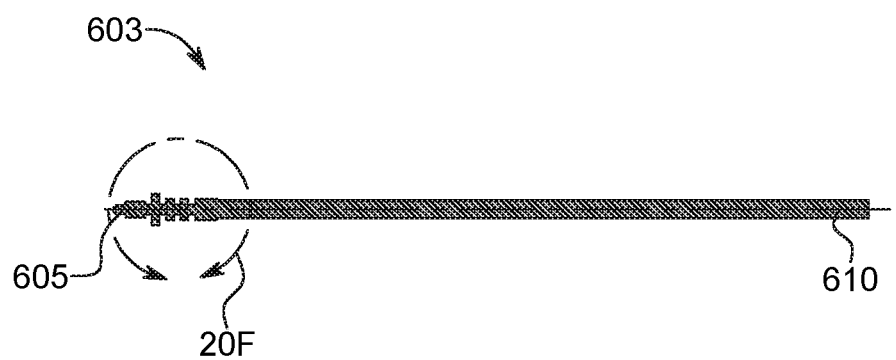
FIG. 20E depicts a cross-sectional view of the plunger of FIG. 19, along axial line 20E-20E.
Figure 20F:
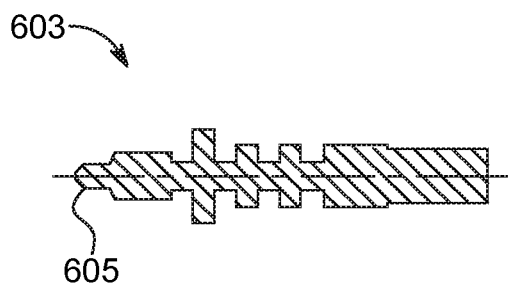
FIG. 20F depicts an enlarged view of a forwardmost portion of the plunger of FIG. 20E.

To accomplish the foregoing tasks, and as further illustrated in FIG. 2, the instrument 100 can include a base 300, a stage 400, a fill station 500, a backdrop assembly 700, and a head assembly 800. The instrument 100 can be used with different types of milling tips. The instrument 100 can be used with an exemplary milling tip 600 (FIG. 18). The base 300, the backdrop assembly 700, and the head assembly 800 are protected by a cover 111 (FIG. 1). Each of these components will now be described in greater detail.

Base 300

Figure 3:
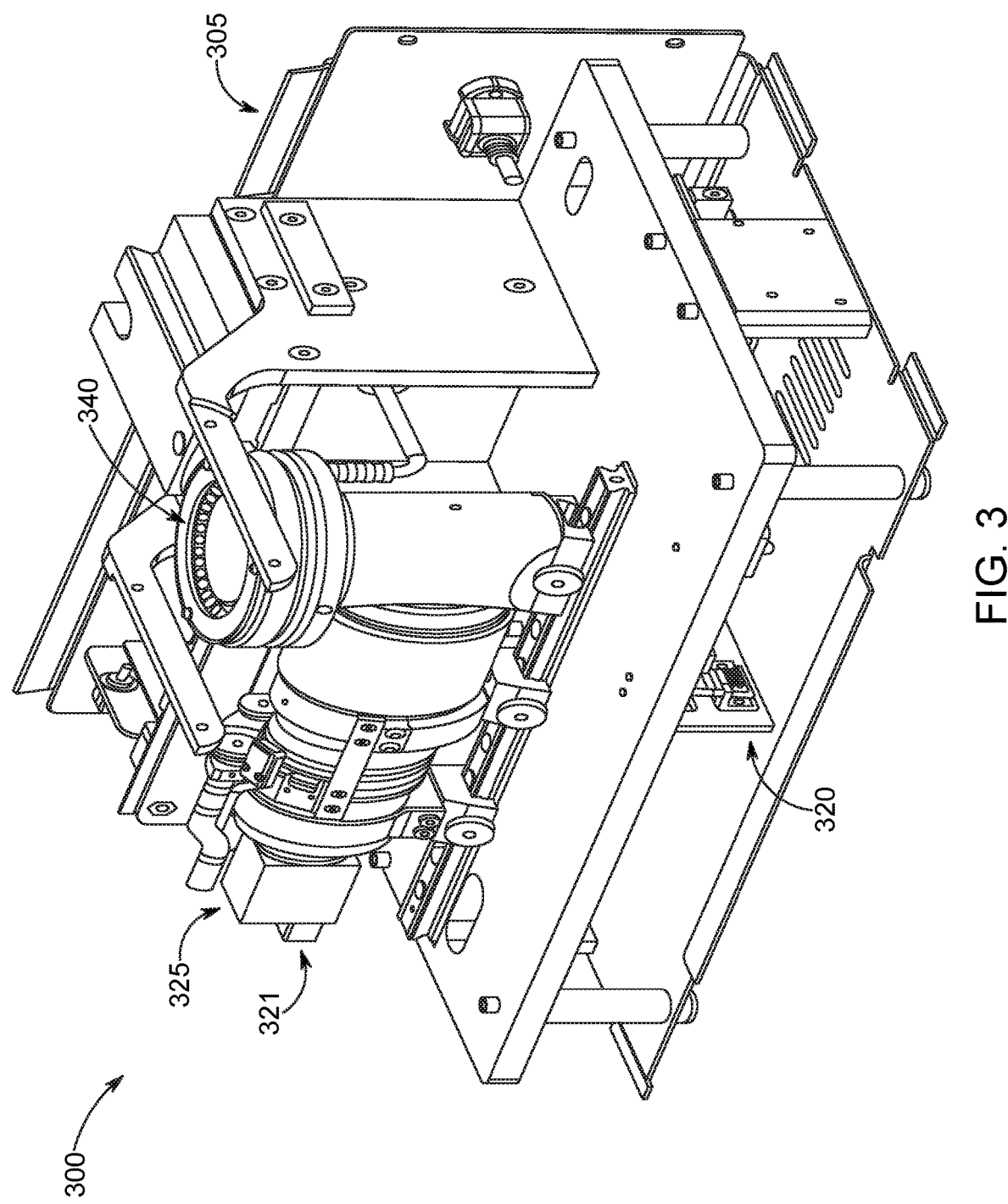
FIG. 3 depicts an enlarged view of the base that forms part of the tissue dissection instrument of FIG. 2, according to an exemplary embodiment of the present disclosure.

With reference to FIG. 3, an exemplary base 300 includes a support structure 305 onto which the remaining components are mounted. The base 300 further includes a workflow module (or processor) 320 that controls the automation of the instrument 100 by implementing the workflow, as it will be described later in more detail. The workflow module 320 is connected to a memory, whether locally or remotely on a remote server. The memory stores computer-readable instructions that, when executed by the processor 320, cause the processor 320 to execute the workflow, as it will be described in greater detail.

An optical system 321 may include a camera 325 and a motorized lens 340. The camera 325 captures desired images of the slides, and further provides a means to verify the size and presence of the milling tips 600, the presence of the collection vials, and the presence and volumes of the dissection buffer solution. According to an exemplary embodiment, the size of each milling tip 600 exceeds approximately 70 uL, and in some embodiments ranges between approximately 200 uL to 300 uL. The lens 340 provides means for focusing the images, providing illumination to the slides, and enabling the zooming (or magnification) function of the live images to any user defined level.

Stage 400

Figure 4:
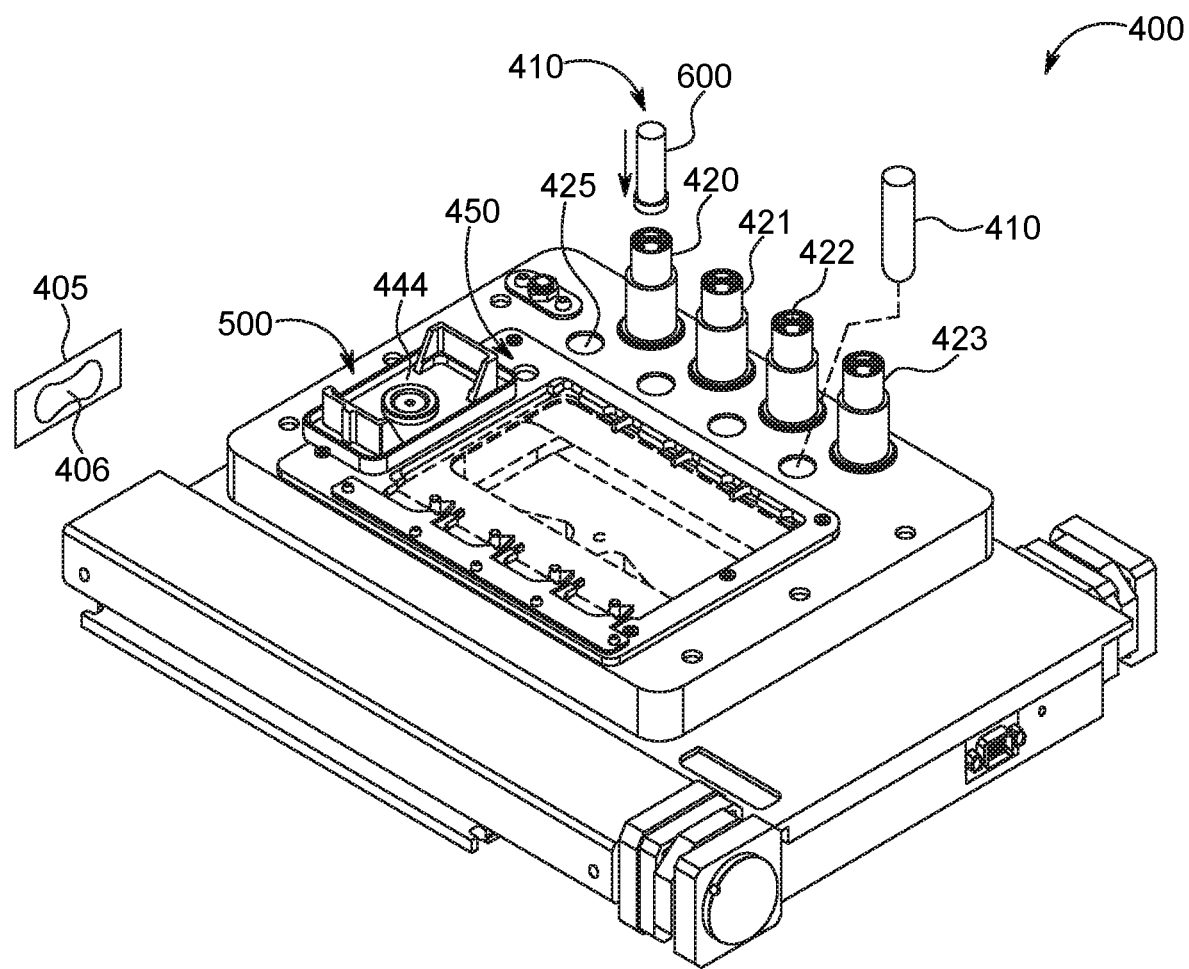
FIG. 4 depicts an enlarged view of the assembled stage that forms part of the tissue dissection instrument of FIG. 2, according to an exemplary embodiment of the present disclosure.

An exemplary assembled stage 400 is illustrated in FIG. 4 and is readily detachable from the head assembly 800 for ease of transportation. FIGS. 5 through 16 depict the main components of the stage 400, according to an exemplary embodiment of the present disclosure. The stage 400 performs numerous functions, among which are the following:

The stage 400 has the capacity and capability to concurrently accommodate and collect samples from several tissue slides 405. While the present exemplary tissue dissection instrument 100 is described as processing four tissue slides 405 on the stage 400 for illustration purpose only, it should be understood that the tissue dissection instrument 100 can serially process a different number of tissue slides 405.

Figure 17:
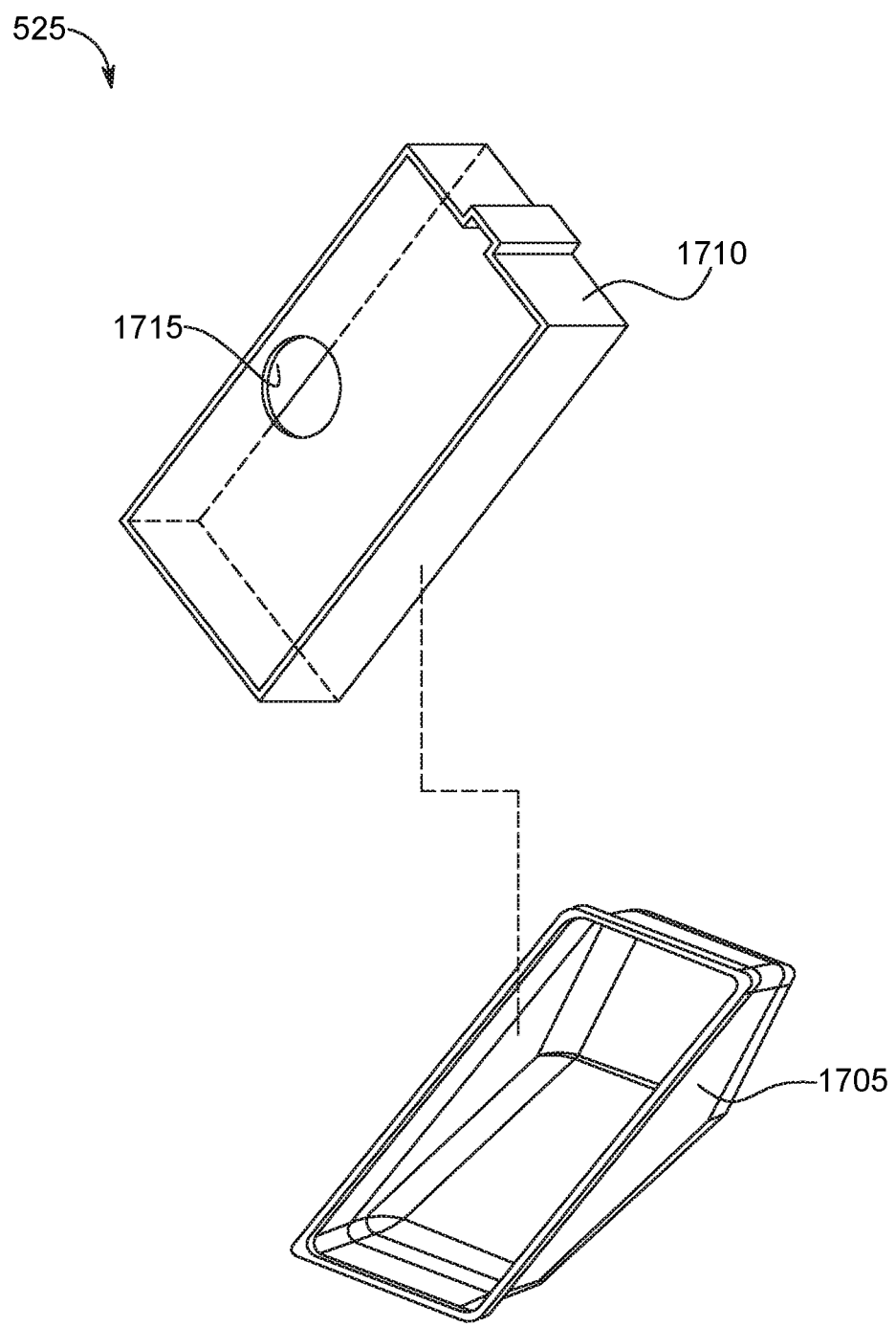
FIG. 17 depicts an assembly view of a fill station reservoir of FIG. 2 that forms part of the fill station, according to an exemplary embodiment of the present disclosure.

The stage 400 enables the automation of the filling and unloading of a plurality of milling tips 600 into a plurality of corresponding sample collection vials 410. To this end, the stage 400 includes a plurality of receptacles 411, 412, 413, 414 (FIG. 5) that are adapted to receive a corresponding number of spring-loaded milling tip holders 420, 421, 422, 423, for holding an equal number of milling tips 600. The milling tip holders 420, 421, 422, 423 are used for automatic loading of the milling tips 600 by the head assembly 800. The stage 400 further accommodates the fill station 500 that enables the automatic filling of the milling tips 600 with a buffer solution from a reservoir 525 (FIG. 17). In addition, the stage 400 includes receptacles or wells 425, 426, 427, 428 (FIG. 5) that are adapted to receive a corresponding number of sample collection vials 410, into which the milling tips 600 containing the buffer solution and collected samples are automatically unloaded (or dispensed), in preparation for forwarding to the clients for additional pathological analysis.

The stage 400 also includes an access 450 to a calibration grid 455 (FIG. 9), which enables a Z-axis actuator assembly 810 to selectively adjust the milling pressure applied by each milling tip 600 on the corresponding tissue slide 405 from which the sample 406 is being excised.

The stage 400 also enables the monitoring of the buffer solution fill status, such as the fills or depletion of the buffer solution, in order to determine if the sufficient volume of buffer solution has been dispensed into the milling tips 600.

Figure 5:
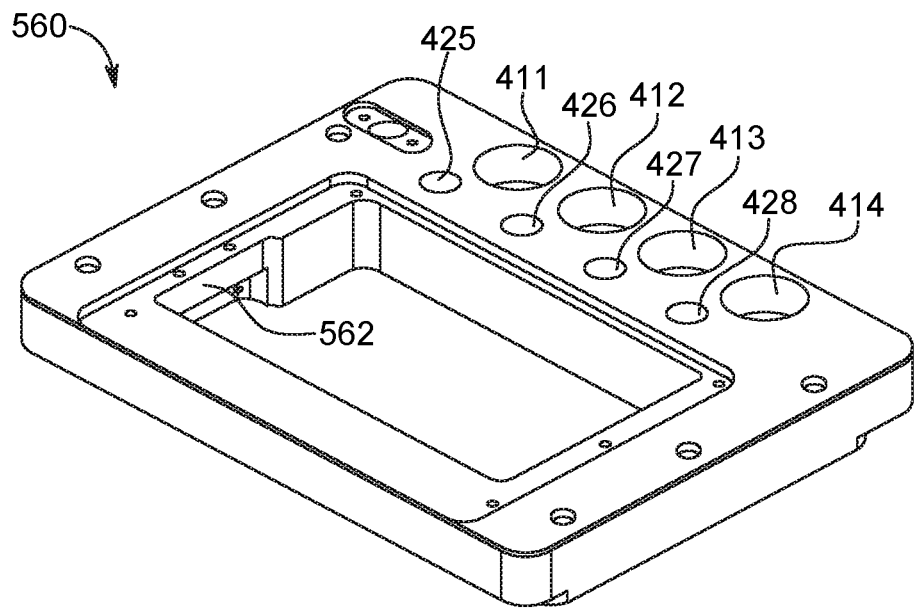
Figure 6:
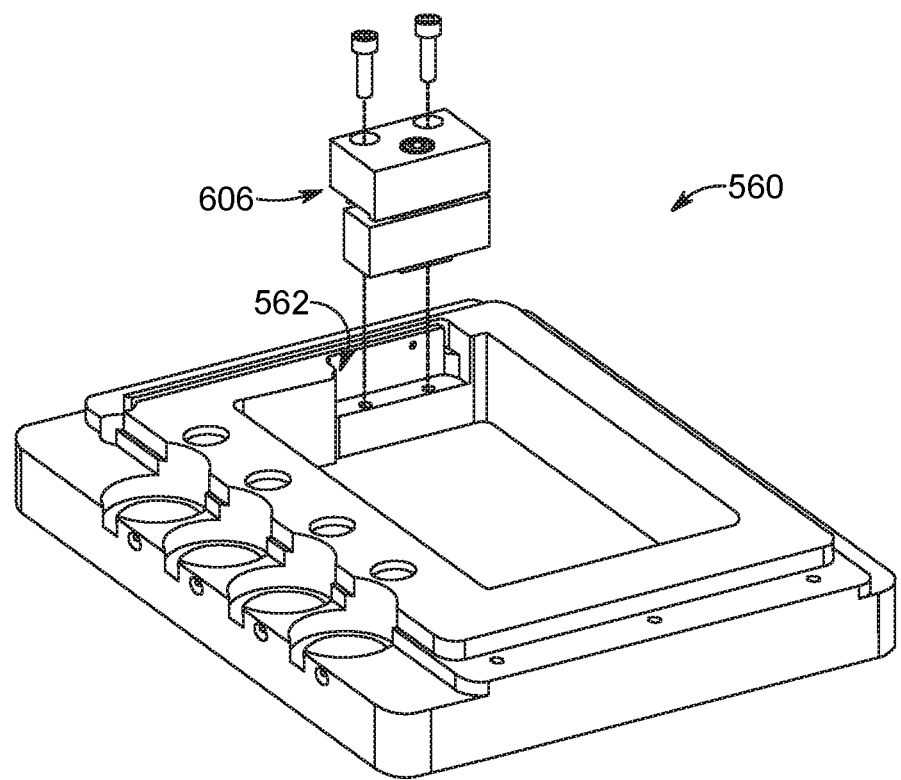
Figure 7:
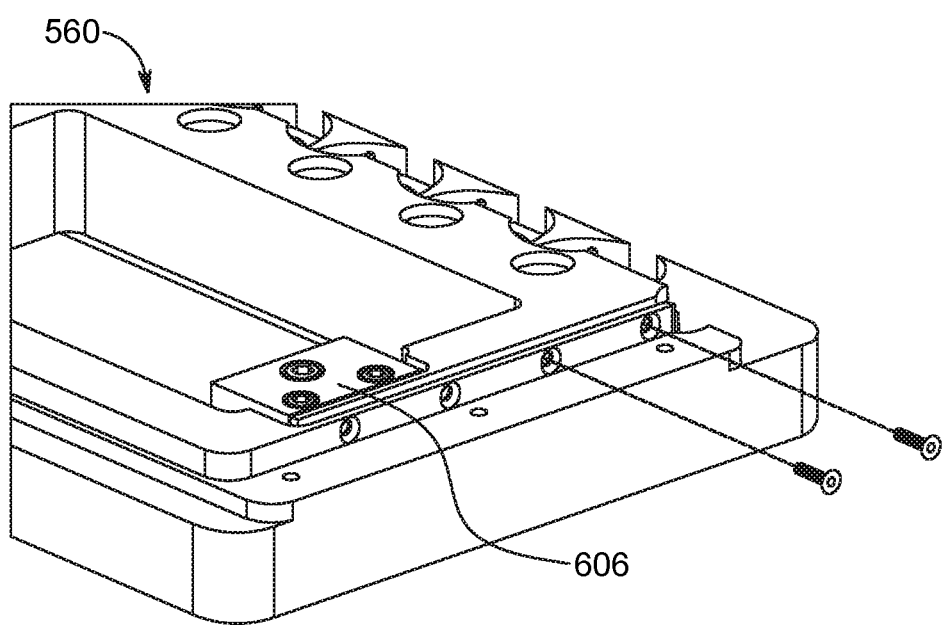

FIG. 5 depicts an exemplary tray 560 into which the receptacles 411, 412, 413, 414, 425, 426, 427, 428 are formed, to respectively receive the spring-loaded milling tip holders 420, 421, 422, 423 and the sample collection vials 410. The tray 560 further includes a fill station receptacle 562 that is shaped to seat a load cell block 606, as further illustrated in FIGS. 6, 7, 8. The load cell block 606 weighs the buffer solution in the filling station reservoir 525 (FIG. 17) in order to monitor the buffer solution fill status.

Figure 8:
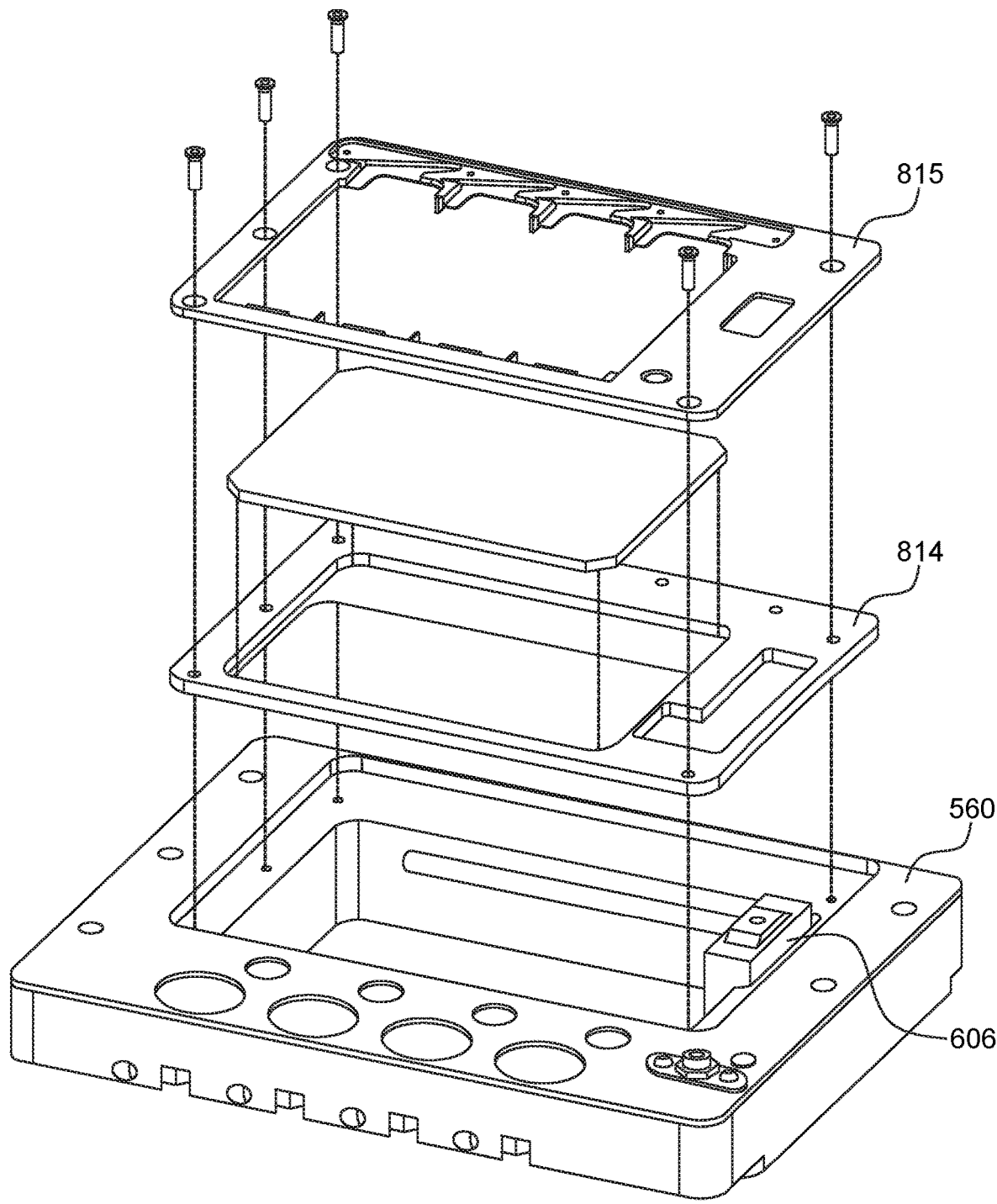
Figure 9:
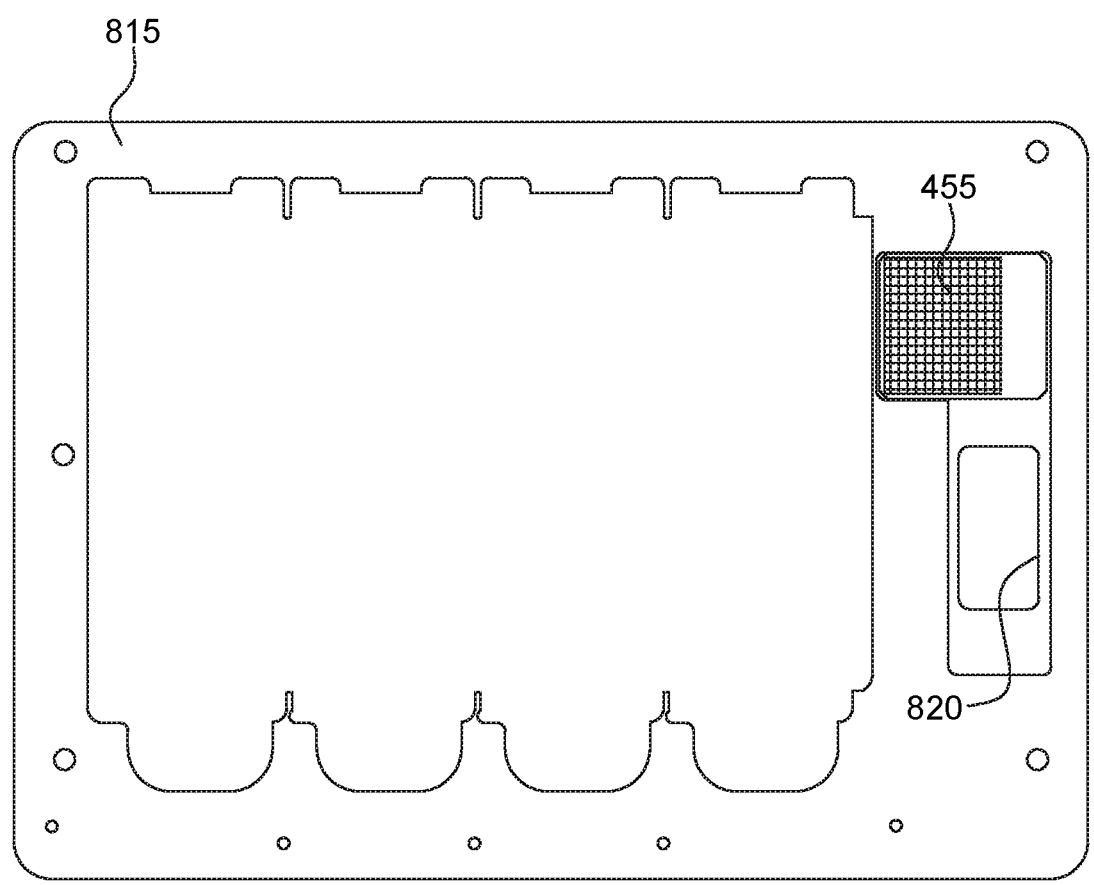

With reference to FIG. 8, the stage 400 further includes a bottom slide frame 805, a glass window or slide 814, and a top slide frame 815, that are secured to the tray 560. The calibration grid 455 is secured to the top slide frame 815, as shown in FIG. 9. A fill station opening 820 is formed in the top slide frame 815 to enable access to the load cell block 606.

Figure 10:
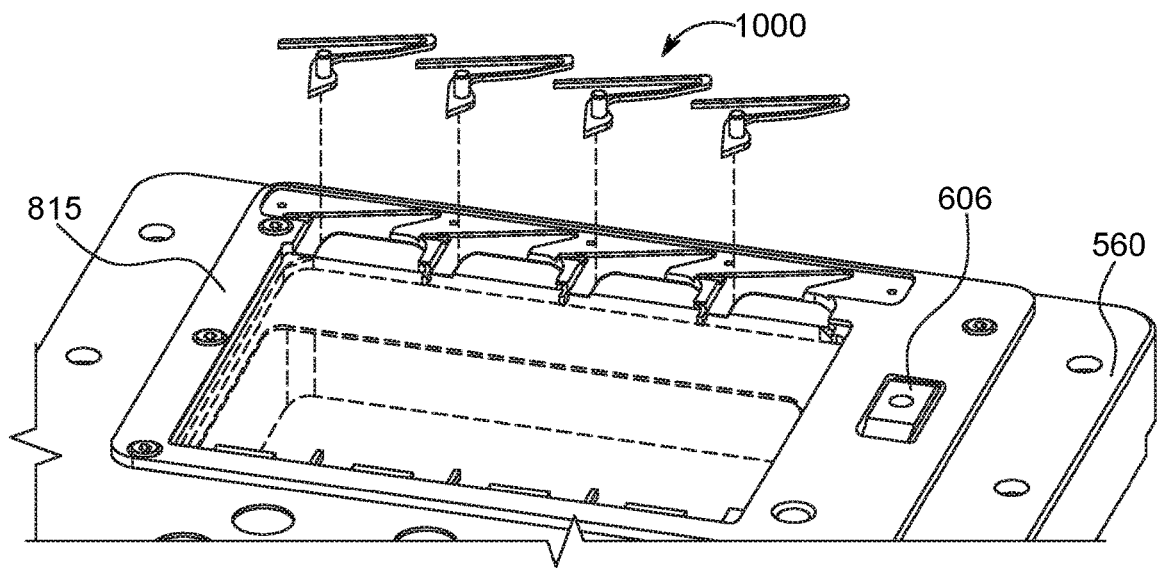
Figure 11:
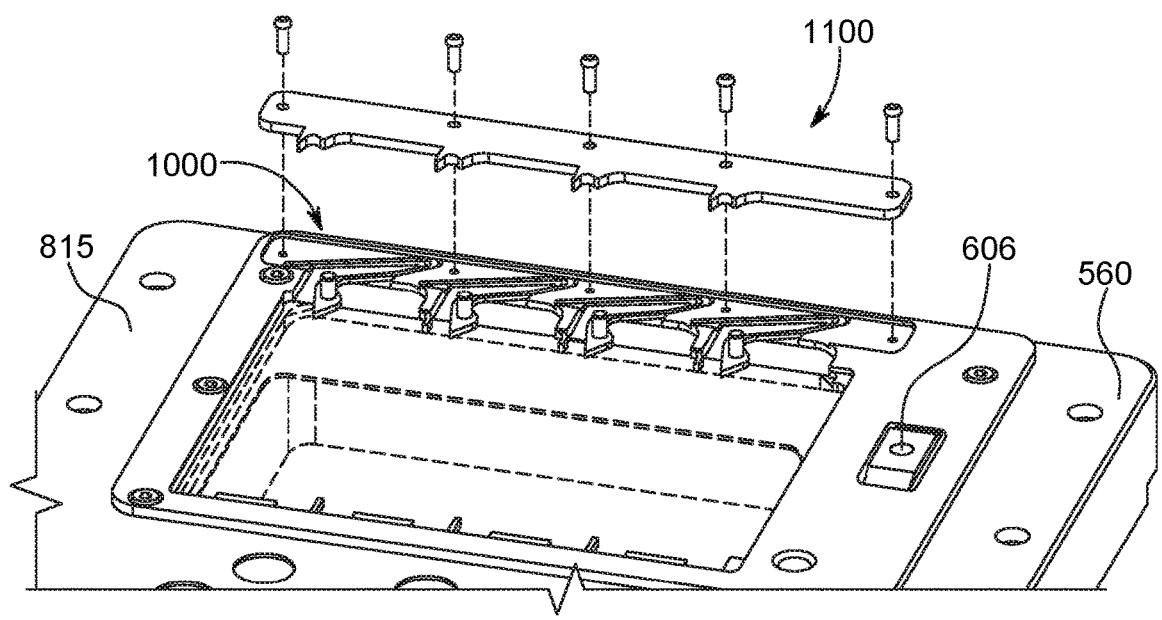

FIG. 10 depicts an exemplary assembly of a slide clamp spring assembly 1000 to the top slide frame 815. FIG. 11 depicts the assembly of a slide clamp cover 1100 in order to secure the slide clamp spring assembly 1000 to the top slide frame 815. The slide clamp spring assembly 1000 and the slide clamp cover 1100 respectively facilitate the seating and release of the tissue slides onto and from the top slide frame 815.

Figure 12A:
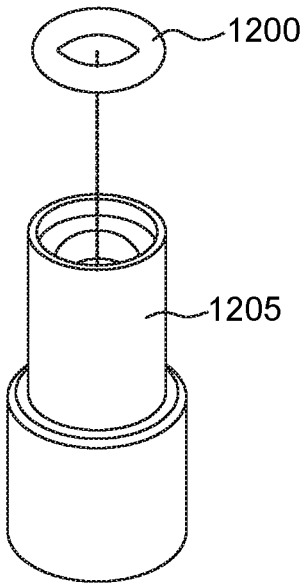
Figure 12B:
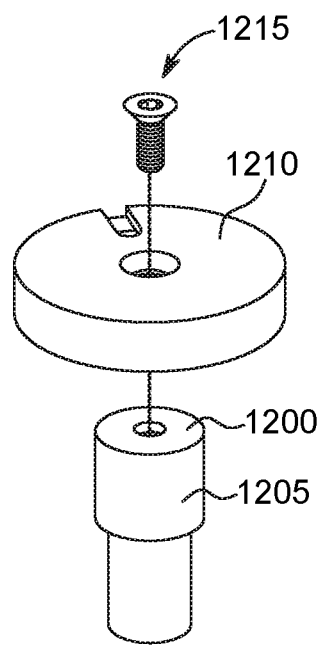
Figure 12C:
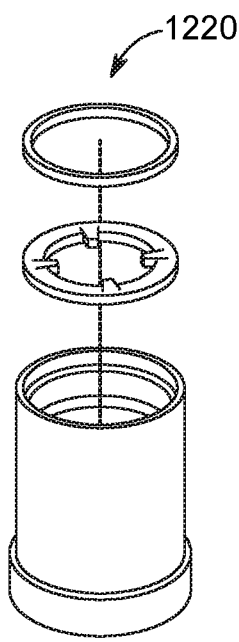
Figure 12D:
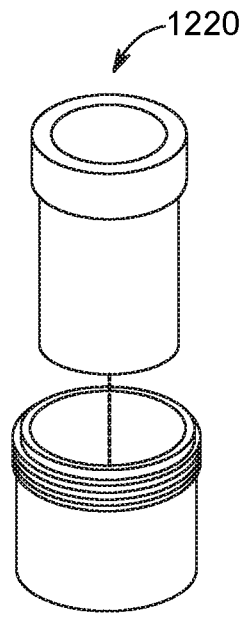
Figure 12E:
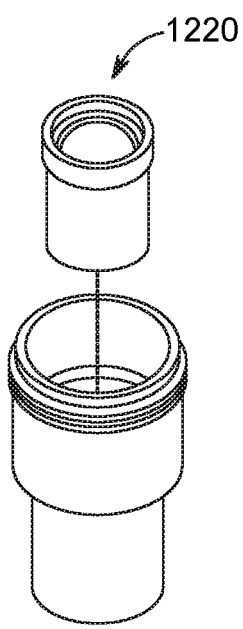

FIGS. 12A, 12B, 12C, 12D, 12E, 12F, 12G, depict exemplary sequential steps in the assembly of the milling tip holder assembly 420. An elastomeric O-ring 1200 is seated within a corresponding opening of a generally cylindrically shaped barrel 1205. A circularly shaped base 1210 is secured to the barrel 1205, with the O-ring 1200 sandwiched therebetween, to form a bottom support 1215. FIGS. 12C, 12D, 12E illustrate the assembly components of a telescoping receptacle 1220. As illustrated in FIGS. 12F, 12G, a spring 1230 is inserted within the telescoping receptacle 1220. The barrel 1205 of the bottom support 1215 is inserted inside the spring 1230, causing the spring 1230 to be compressed, and allowing the bottom support 1215 to be secured to the telescoping receptacle 1220.

Figure 13:
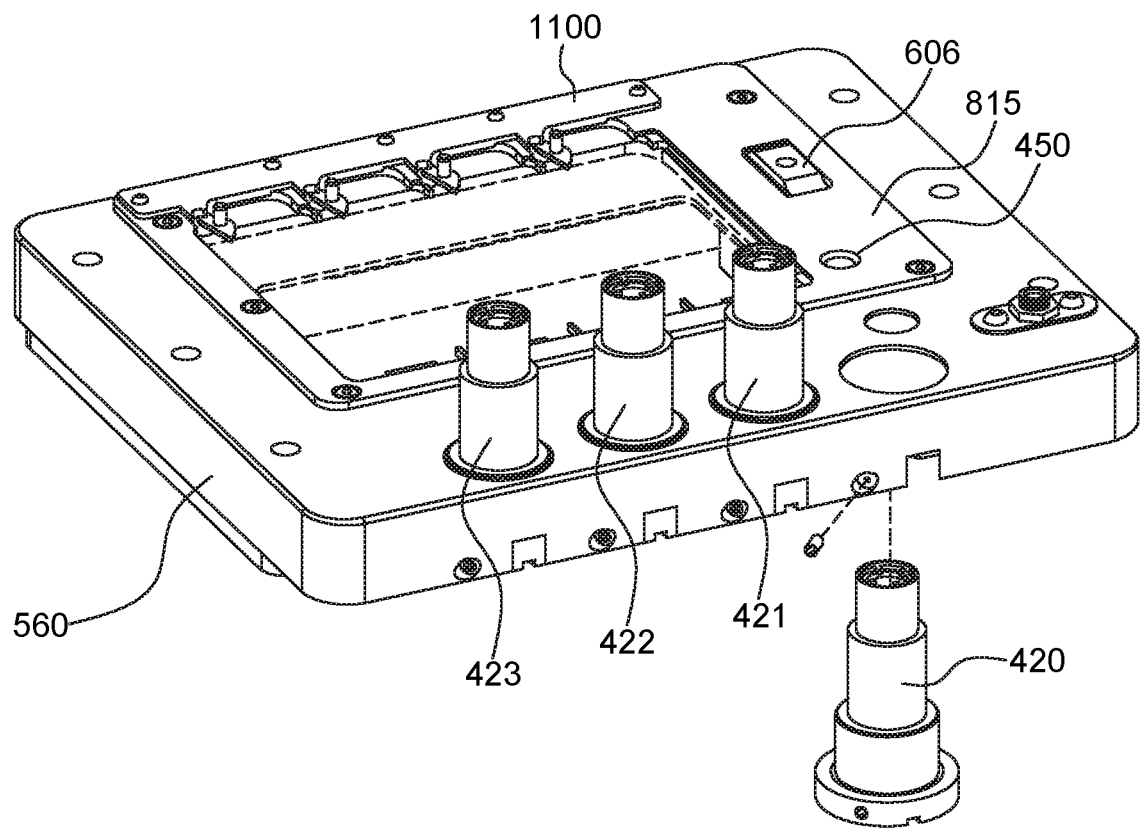

FIG. 13 depicts an exemplary assembly of four milling tip holders 420, 421, 422, 423 to the tray 560 with the load cell block 606 that is shown accessible through the top slide frame 815.

Figure 14:
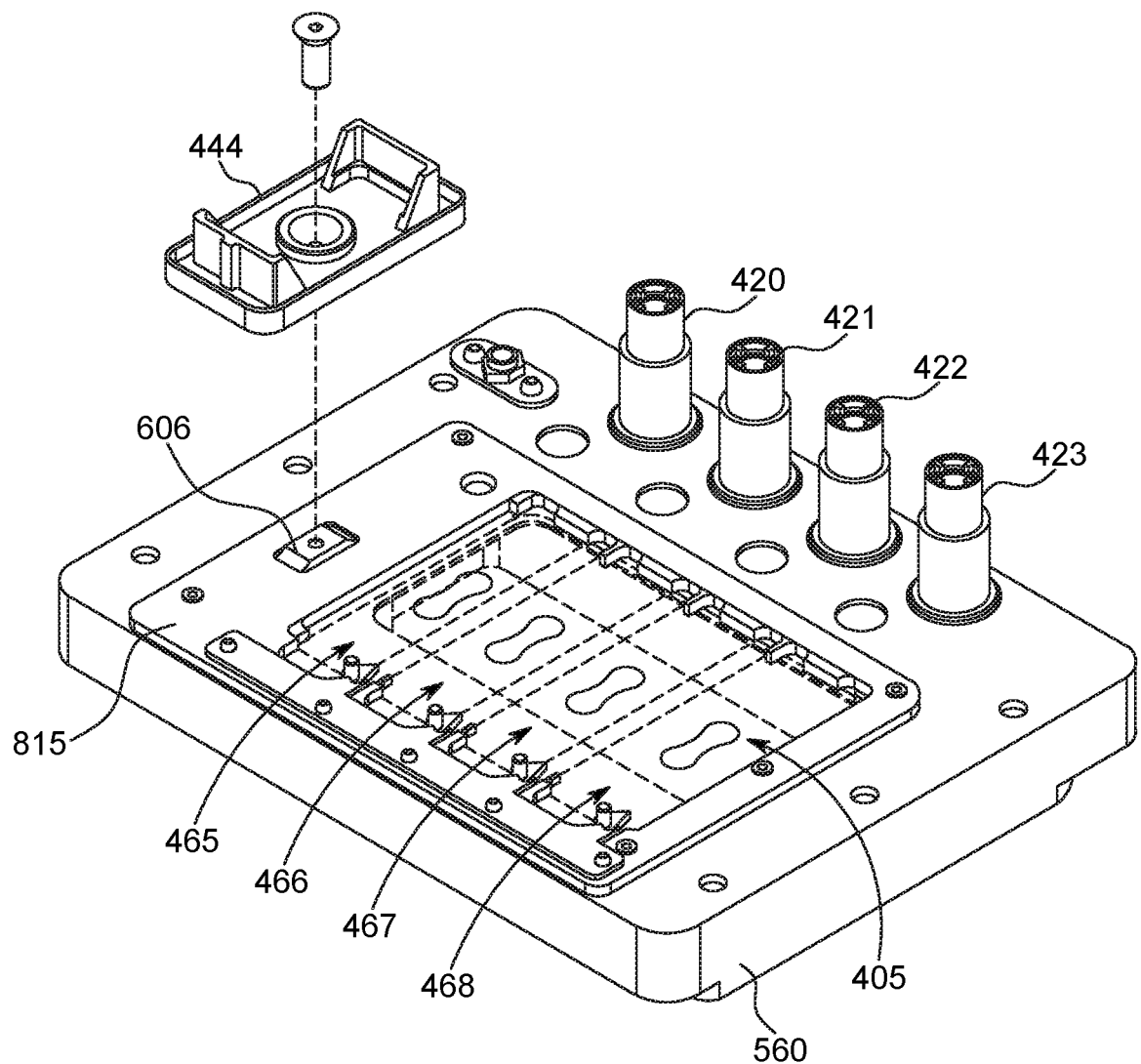

FIG. 14 depicts an exemplary reservoir riser 444 being secured to the load cell block 606. The reservoir riser 444 is designed to receive the filling station reservoir 525 (FIG. 17) that stores the buffer solution. FIG. 14 further depicts, in dashed lines, four sample slides 465, 466, 467, 467 (also collectively referred to with the numeral reference 405) loaded in position onto the top slide frame 815 of the stage 400.

Figure 15A:
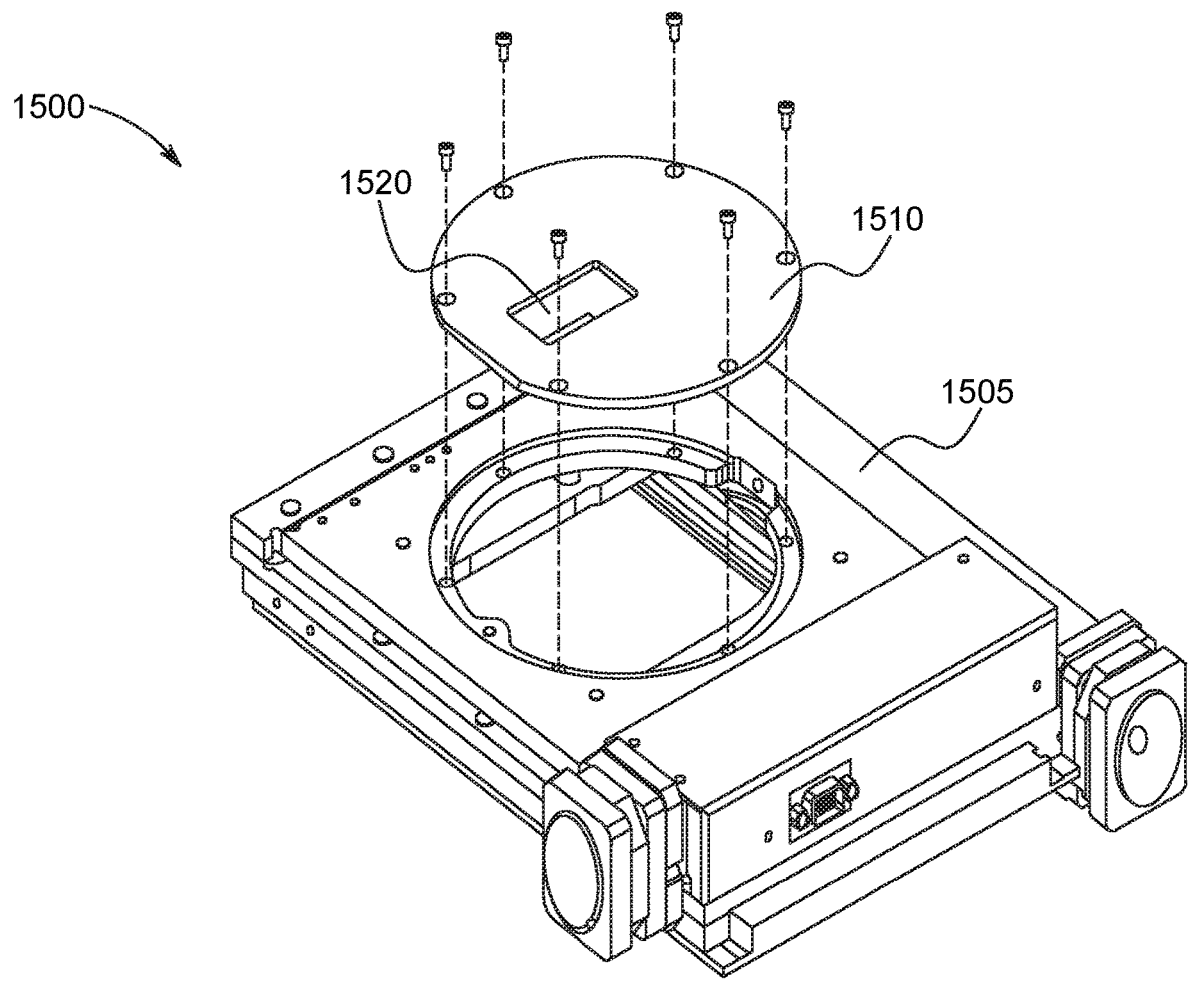
FIGS. 15A and 15B depict two assembly views of a support platform.
Figure 15B:
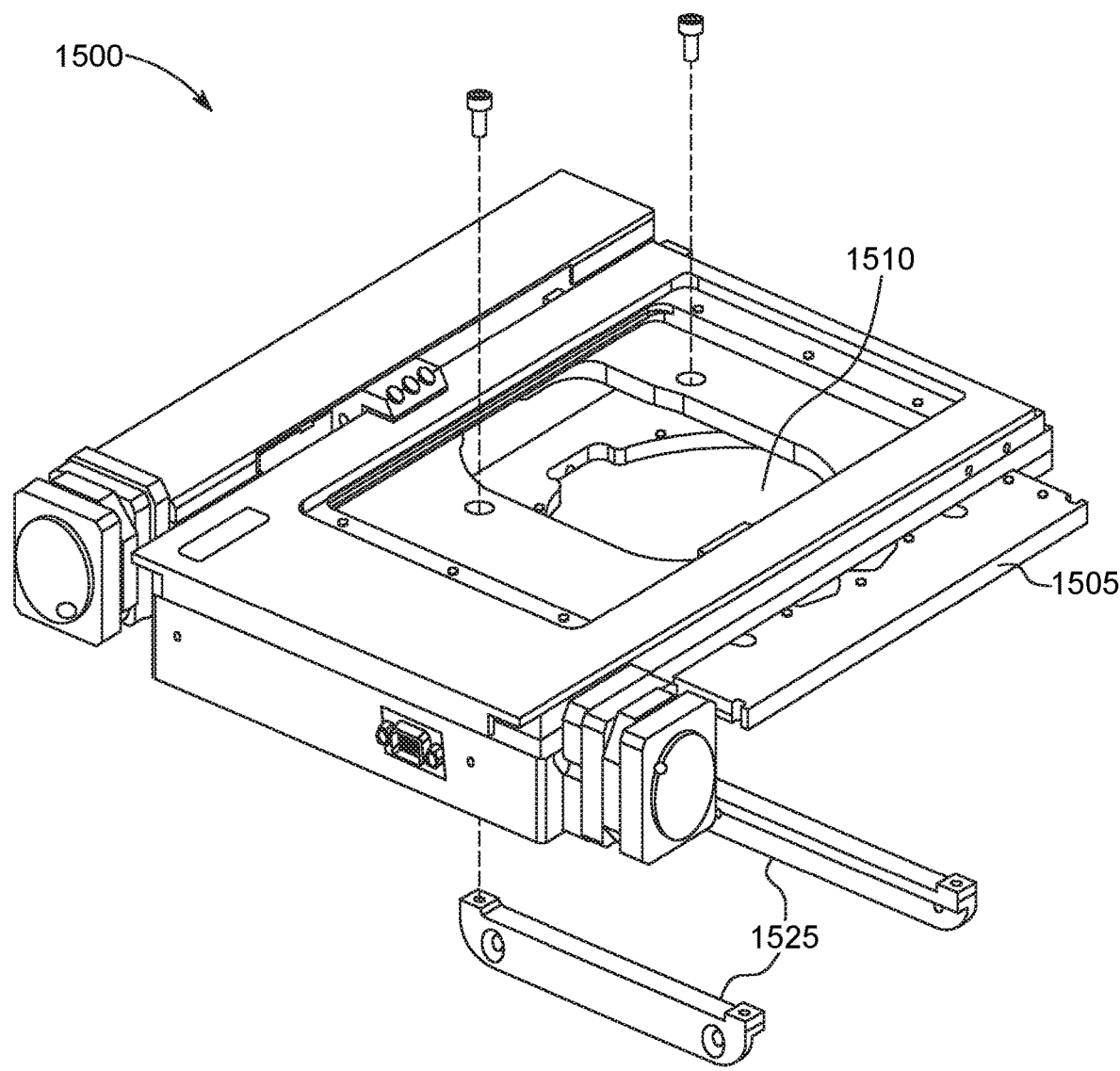
Figure 16:
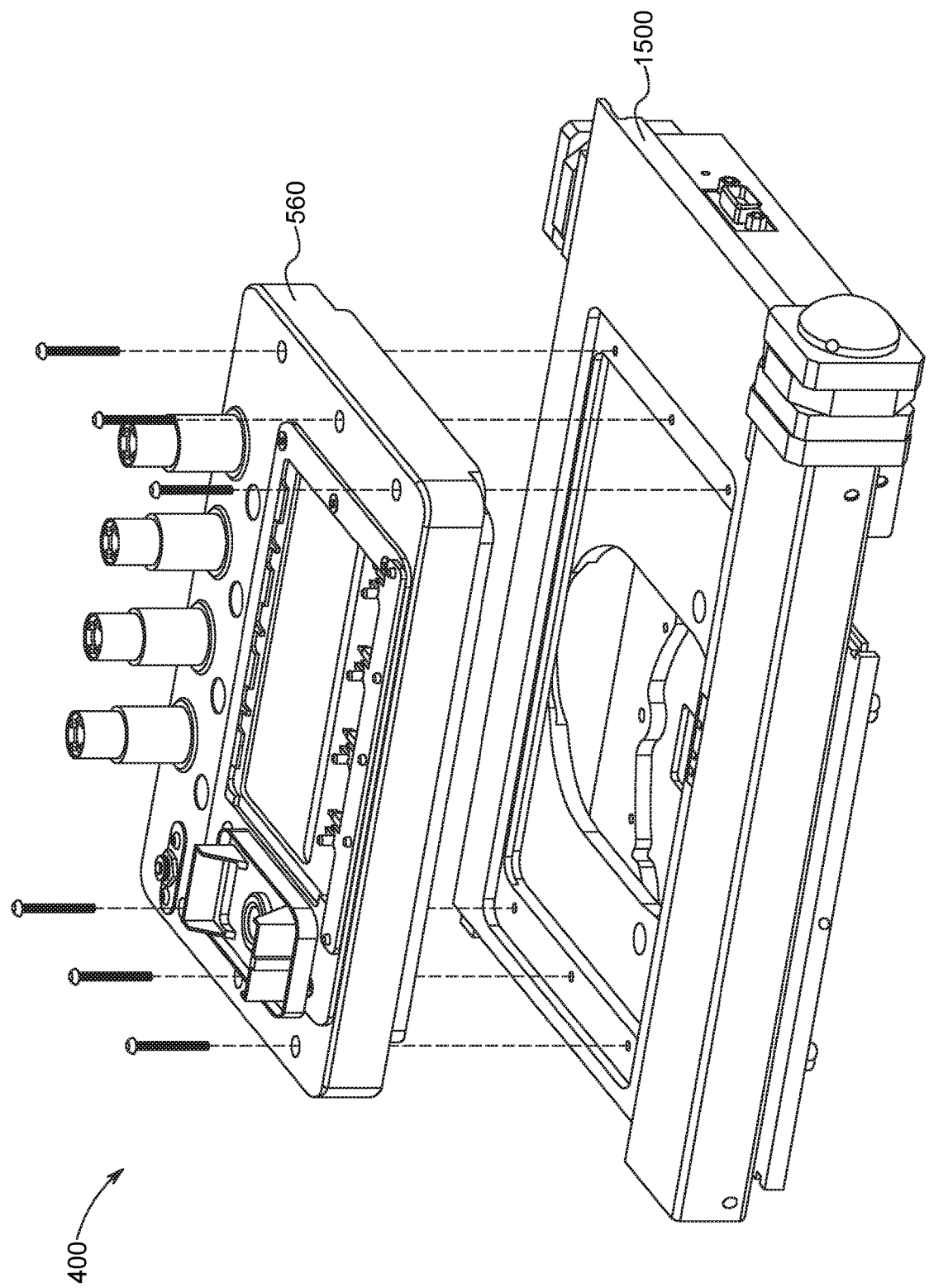

FIGS. 15A and 15B depict two assembly views of an exemplary support platform 1500. A generally circular opaque disc 1510 with an optical opening 1520 is secured to a base 1505. Two tracks 1525 are secured to the base 150 to guide the support platform 1500 and thus the completely assembled stage 400, into position in the head assembly 800. FIG. 16 depicts the assembly of the tray 560 and the support platform 1500, to complete the assembly of the stage 400.

Fill Station 500

FIG. 17 depicts an assembly view of the fill station reservoir 525 that forms part of the fill station 500. The fill station reservoir 525 includes a container 1705 that connects to the reservoir riser 444 which is already secured to the load cell block 606. The reservoir riser 444 forms platform edges to hold the container 1705, and is contoured to contain liquid in case there is a leak in the fill station reservoir 525. The fill station container 1705 has a generally inversed roof design that fits within the reservoir riser 444. A cover 1710 with a top opening 1715 fits atop the fill station container 1705, and enables the milling tip 600 to sample at the middle of the container 1705, in order to minimize the amount of dead space at the end of a fill. In one embodiment, the fill station 500 allows the automatic filling of a single milling tip 600 with buffer solution, at a time. The fill station 500 is electronically monitored, prior to the filling of the milling tips, in order to determine if enough buffer solution is available for the tissue dissection process.

Milling Tip 600

FIGS. 18, 19, 20A, 20B, 20C, 20D, 20E, 20F further illustrate the milling tip 600 for use in the tissue dissection instrument 100 according to an exemplary embodiment of the present disclosure. The milling tip 600 is generally comprised of an outer barrel 601, a reservoir 602, a plunger 603, and a seal 604, and is assembled by inserting the reservoir 602 into the outer barrel 601, and by further inserting the plunger 603 inside the reservoir 602. The plunger 603 is inserted through a threaded section 610 of the plunger 603 and into the outer barrel 601, in order to seal the buffer solution within the outer barrel 601 and to support the plunger 603 along an axial position. Silicone or another sealer can also be added to provide a further fluidic seal between the various component of the milling tip 600.

Upon completion of the assembly of the milling tip 600, the threaded section 610 is allowed to protrude from the seal and the outer barrel 601. When the milling tip 600 is securely seated in the corresponding milling tip holder 420, the threaded section 410 can be threaded to the head assembly 800, so that the milling tip 600 and can be retrieved from the milling tip holder 420 and automatically moved to be filled at the fill station 500.

The forwardmost section of the outer barrel 601 includes an opening 605 that is dimensioned such that when a milling force is applied to the milling tip 600, an excision blade 651 of the plunger 603 protrudes out of the opening 605 to perform the desired milling or cutting of the desired area (or areas) of interest on the tissue sample 406, and to further aspire the excised sample along with the buffer solution.

The variable size of the excision blade 651 defines the size of the milling tip 600, which enables the user to select one of numerous sizes. As an example only, the sizes can gradually range from fine to coarse in stepped increments. The size of the milling tip 600 is defined by the volume of the outer barrel 601 and the reservoir 602. As an example the volume of the outer barrel 601 can be approximately 350 ul.

Although other milling tips can be used with the tissue dissection instrument 100, one exemplary milling tip is described in U.S. Publication No. 2016/0251708, which is incorporated herein in its entirety by this reference. The head assembly 800 that retains the milling tip 600, causes the milling tip 600 to rotate while withdrawing the plunger 610, which simultaneously dispenses the buffer solution to the excision blade 65, dissects the tissue 406 within the designated areas of interest (as it will be explained later in more detail), and aspirates the dispensed buffer solution along with the excised tissue fragments into a designated collection vial 641, by depressing the plunger 610. The milling tip 600 may either be reloaded into a milling tip holder 420 or discarded to avoid cross contamination.

Backdrop Assembly 700

Figure 21:
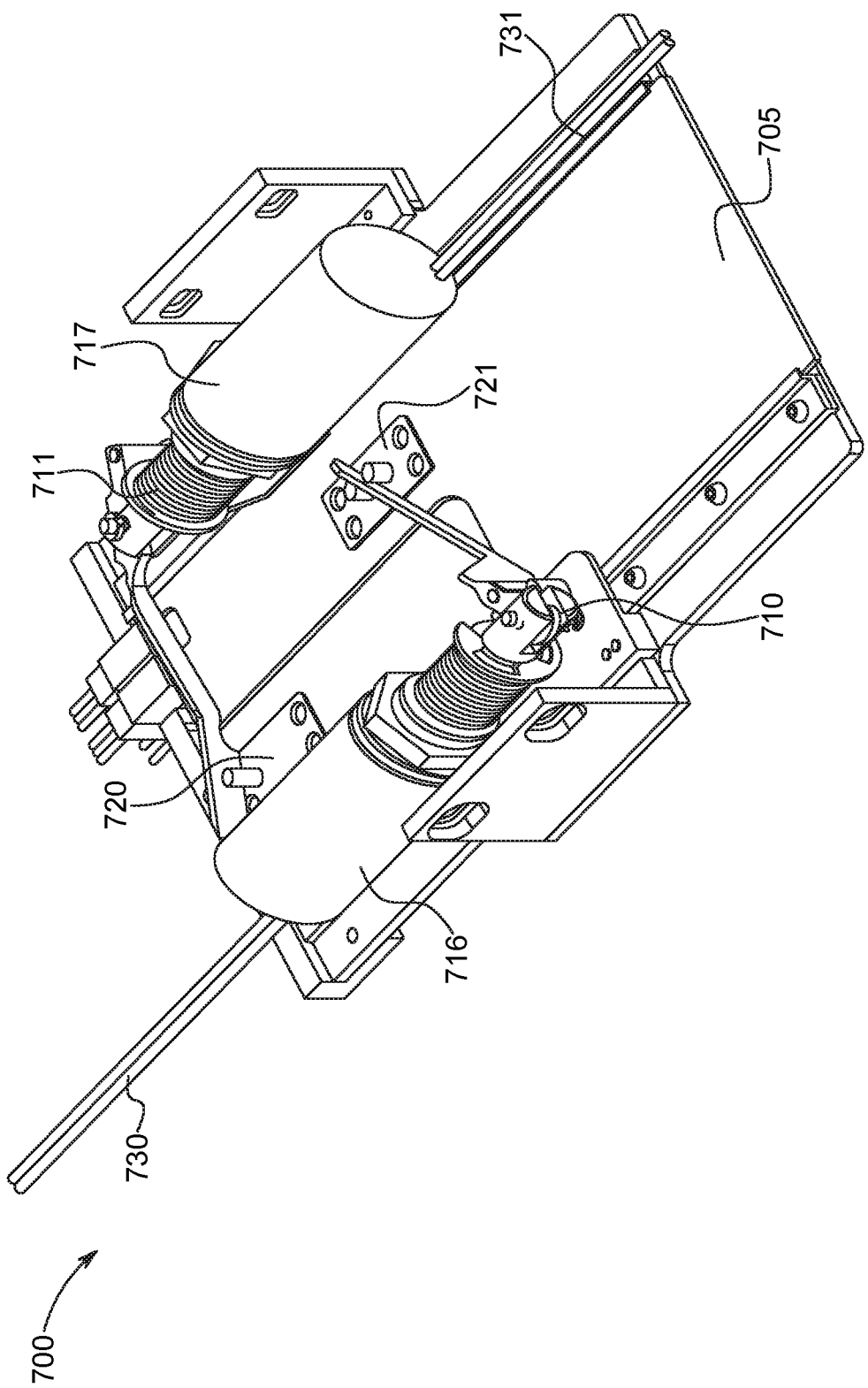
FIG. 21 depicts the backdrop assembly of FIG. 2, according to an exemplary embodiment of the present disclosure.

With reference to FIG. 21, it depicts the backdrop assembly 700 according to an exemplary embodiment of the present disclosure. In general, the backdrop assembly 700 comprises a backdrop base plate 705 on which two actuators 710 and 711 are mounted. The actuators 710 and 711 are respectively driven by two solenoids 716, 717, in order to drive either a lower backdrop slide 720 or an upper backdrop slide 721 in alignment with the illumination beam emanating from the optical system 321 (FIG. 3), through the base 400 (FIG. 4).

The backdrop assembly 700 is retractable and the automated activation of the solenoids 716, 717 provide both white and black backdrops on parallel rails 730, 731. The backdrop assembly 700 allows for either an automatic or a manual selection of one of several colored backdrops. For illustration purpose only, the exemplary backdrop assembly 700 includes an automated black backdrop that is provided by the actuation of the lower backdrop slide 720, and a white backdrop that is provided by the actuation of the upper backdrop slide 721. In addition, the backdrop assembly 700 provides a default no backdrop is selected if neither of the lower backdrop slide 720 or upper backdrop slide 721 is selected.

Optical alignment can be done through the backdrop assembly 700, enabling the users to optimize their slide image by selecting the most appropriate backdrop color based on the type of slide 406 on the stage 400 (e.g., white, silver, or black plate).

Head Assembly 800

Figure 22:
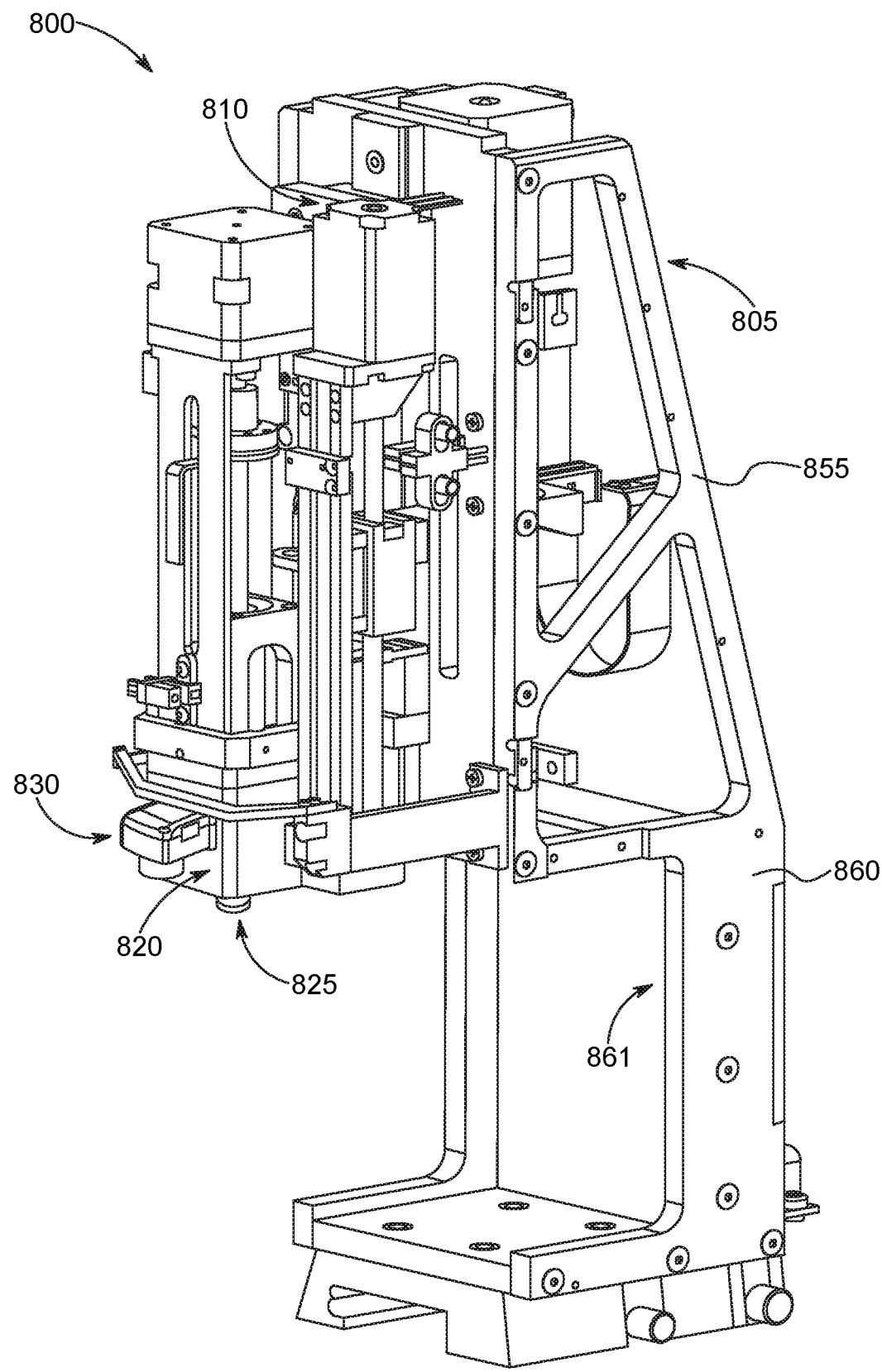
FIG. 22 depicts the head assembly of FIG. 2, illustrating a mount, barcode reader, an aspirator assembly, and a Z-axis actuator assembly, according to an exemplary embodiment of the present disclosure.
Figure 23:
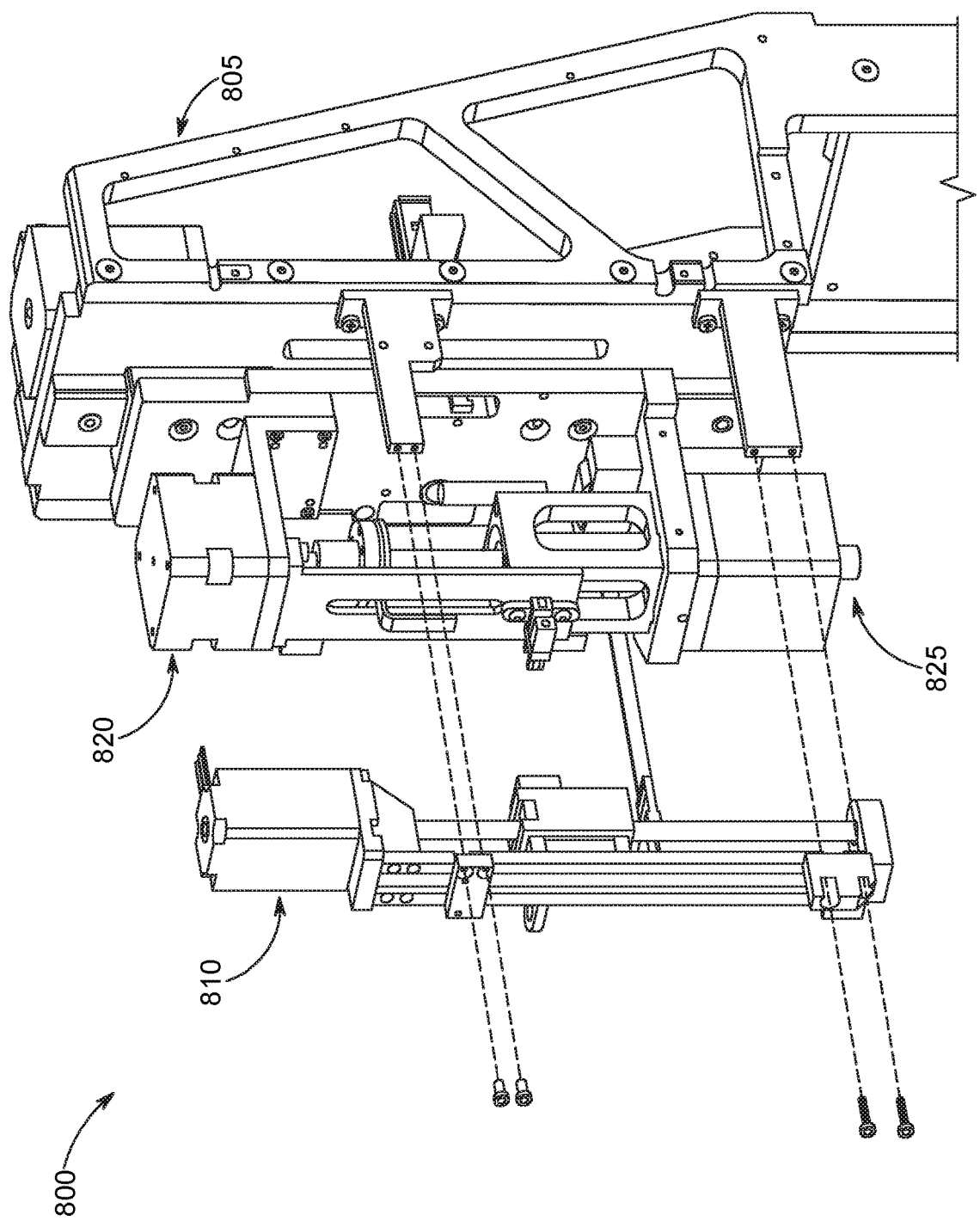
FIG. 23 depicts an assembly view of the head assembly of FIG. 22.

FIGS. 22 and 23 depict an exemplary head assembly 800 that may include a support structure (or mount) 805, a Z-axis actuator assembly 810, an aspirator assembly 820 that terminates in a milling tip interface 825, and a barcode reader 830, according to an exemplary embodiment of the present disclosure. The milling tip interface 825 threadably engages the threaded section 610 of the plunger 603.

The foregoing components of the head assembly 800 are secured, whether directly or indirectly, to an upper portion 855 of the support structure 805. The support structure 805 further provides a bottom section 860 the defines an empty compartment 861 which is sized and dimensioned to accommodate the base 300, the stage 400, and the backdrop assembly 700, as illustrated in FIG. 2.

In some embodiments, the Z-axis actuator assembly 810 is motorized so that it tows the aspirator assembly 820 and the barcode reader 830 along the Z-direction, along the support structure 805. By regulating the elevation of the aspirator assembly above the stage 400, the aspirator assembly 820 controls the pressure applied onto the sample slide 405 via the milling tip 600. In addition, the tissue dissection instrument 100 can be calibrated by applying a calibration force onto the calibration grid 455 through the milling tip 600.

The aspirator assembly 820 draws the mixture of the collected tissue sample 406 and the buffer solution into the milling tip 600.

The barcode reader 830 enables the automatic reading of the various barcodes on the fill station 500 to identify the buffer solution batch number; on the milling tip to identify it by batch number, size, and volume; and on the collection vials 410 in order to associate the collections vials with the excised sample and buffer solution. Optionally, a manual barcode reader can additionally be provided to read the foregoing data, or if the automatic reading of the data by means of the barcode reader 830 becomes difficult to achieve.

Figure 24:
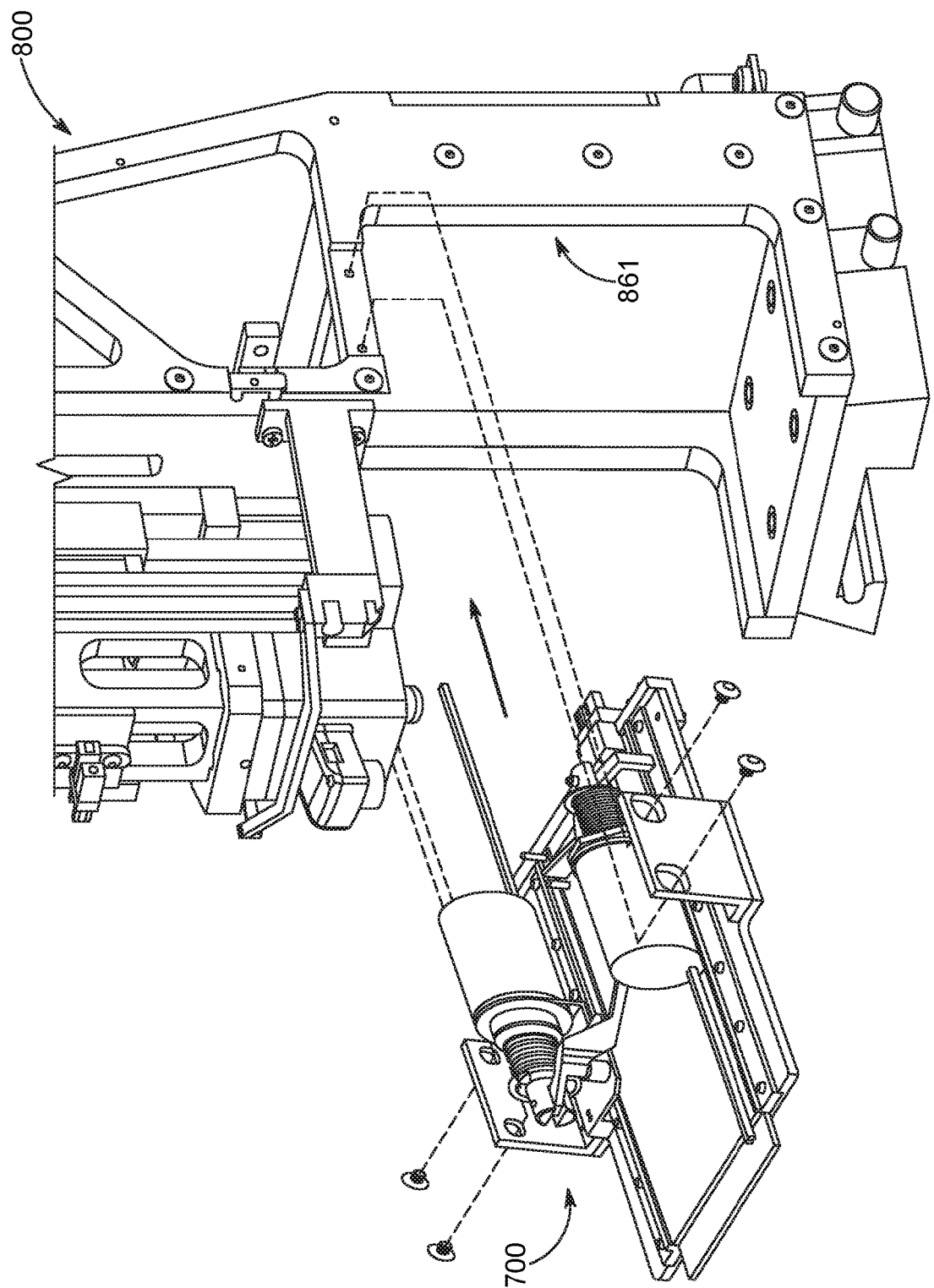
FIG. 24 depicts an assembly view of the head assembly of FIG. 22 and the backdrop assembly of FIG. 21.

FIG. 24 depicts the backdrop assembly 700 being assembled within the compartment 861 of the head assembly 800.

Workflow 2500

Figure 25:
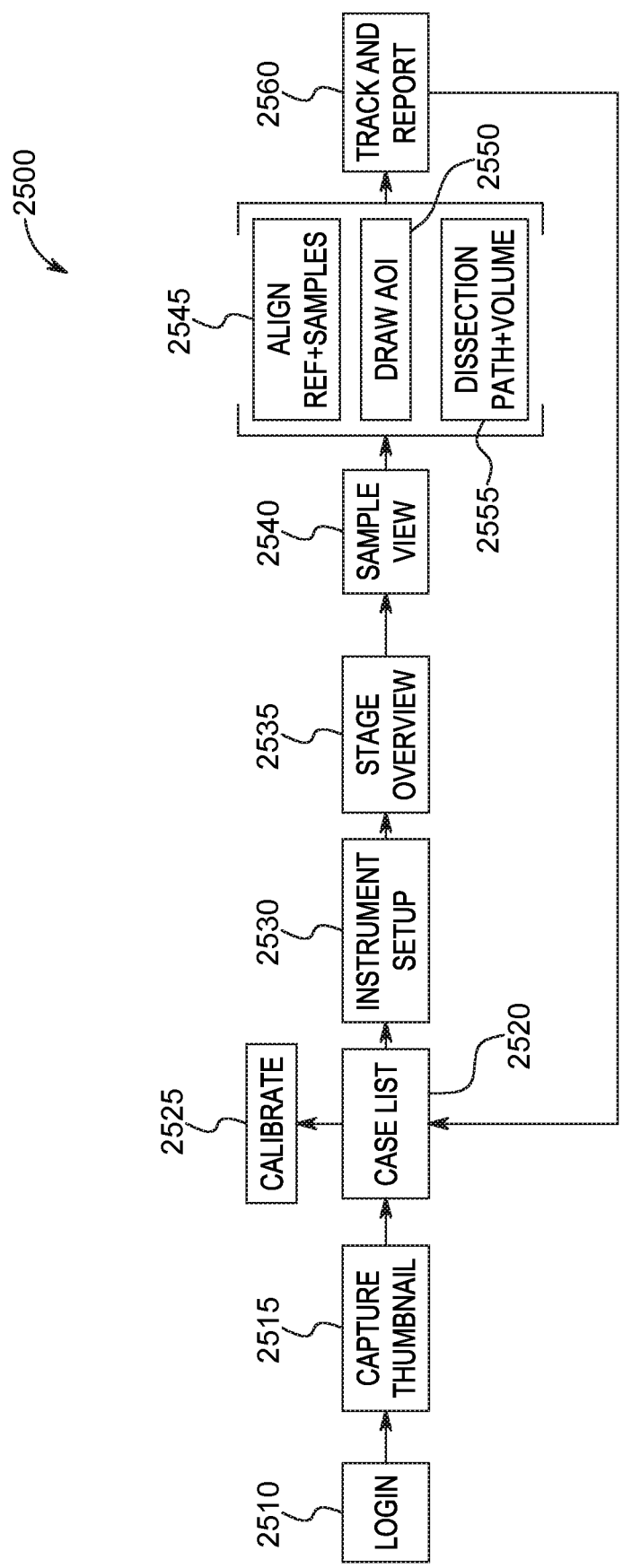
FIG. 25 illustrates a general workflow for operating the tissue dissection instrument, according to an exemplary embodiment of the present disclosure.

FIG. 25 represents an exemplary workflow 2500 for operating the tissue dissection instrument 100, according to an exemplary embodiment of the present disclosure. The workflow 2500 includes a user interface, and can reside on the workflow module 320, a local server, a remote server, or a remote processor. At step 2510, the user starts by logging in to the tissue dissection instrument 100. Login is an important way to track who is using the tissue dissection instrument 100, as well as opening a session for time tracking and other similar applications. As soon as the user logs in, he or she will be prompted with a warning to check if the stage 400 is clear from obstructions.

Once the tissue dissection instrument 100 is initialized, the workflow 2500 proceeds to step 2515 to capture a low resolution image of the stage 400 and to read the various barcodes, as described earlier, using the barcode reader 830.

At step 2520 of the workflow 2500, the user inputs the case list information. The user determines if the tissue slides 405 relate to an open case or to a new case. If the open case option is selected, and the site has an integrated laboratory information system ("LIS") and barcode system, the tissue dissection instrument 100 will be able to connect the slides 405 to the open case in the LIS system for downstream data review. The user may also access previous cases completed on the tissue dissection instrument 100.

If, on the other hand, the user determines that this is a new case, or if the tissue dissection instrument 100 is not integrated with a LIS with a barcode system, the user will be able to "create a new case" from the screen and proceed to calibrate the tissue dissection instrument 100 at step 2525, if calibration was not previously performed.

The user calibrates a sensor within the load cell block 606 of the fill station 500, by attaching an empty reservoir 525 and by selecting a "Fill Station Empty" key on a computer or monitor. The processor 320 reads and records the voltage output from the load cell block 606. The user then fills the reservoir 525 with a precise weight (and/or volume) of buffer solution and selects a "Fill Station Full" key. The processor 320 reads and records the voltage output from the load cell block 606. The processor 320 calculates the variation between the two measured readings, and uses this variation in the readings along with entered weight (and/or volume) to calculate a voltage/gram constant for the load cell block 606.

In addition, the user has the ability to calibrate the automatic tip pressure actuator, which is also referred to herein as the Z-axis actuator assembly 810. The automatic tip pressure actuator 810 allows the user to adjust the amount of pressure to be exerted by the milling tip 600 on the tissue sample to 406 during the excision process. The tip pressure can be manually or automatically adjusted based at least on the tissue type and the type and size of the selected milling tip 600. The objective of this calibration step is to ensure that the tissue dissection instrument 100 consistently dissects tissue samples 406 across various types of tissue samples 406 and milling tips 600. The calibration is performed on an indented section (or access) 450 of the stage 400.

Once the calibration stage 2525 is confirmed to have been completed, the workflow 2500 guides the user to the "Instrument Setup" step 2530. With further reference to FIG. 26, it illustrates an exemplary screen shot 2600 that is associated with the setup step 2530. At this step 2530, the user inputs the case information 2610 (if no LIS or barcode is present) and specifies the type of tissue sample 406 being used. The user will also have a chance to import a digital reference image 2625 stored on his or her computer (or the software retrieves it automatically from the LIS).

The user also enters the necessary parameters to enable the calculation of the desired tissue volume 2620 to be excised. The tissue volume 2620 is calculated based on the tissue thickness, type, and downstream application selected for the case. The tissue volume 2620 is configurable by an administrator based on lab protocols. The calculated tissue volume 2620 is considered a guideline, and the user can manual enter the desired amount. The user has the further option of manually entering additional relevant notes 2630.

Figure 27:
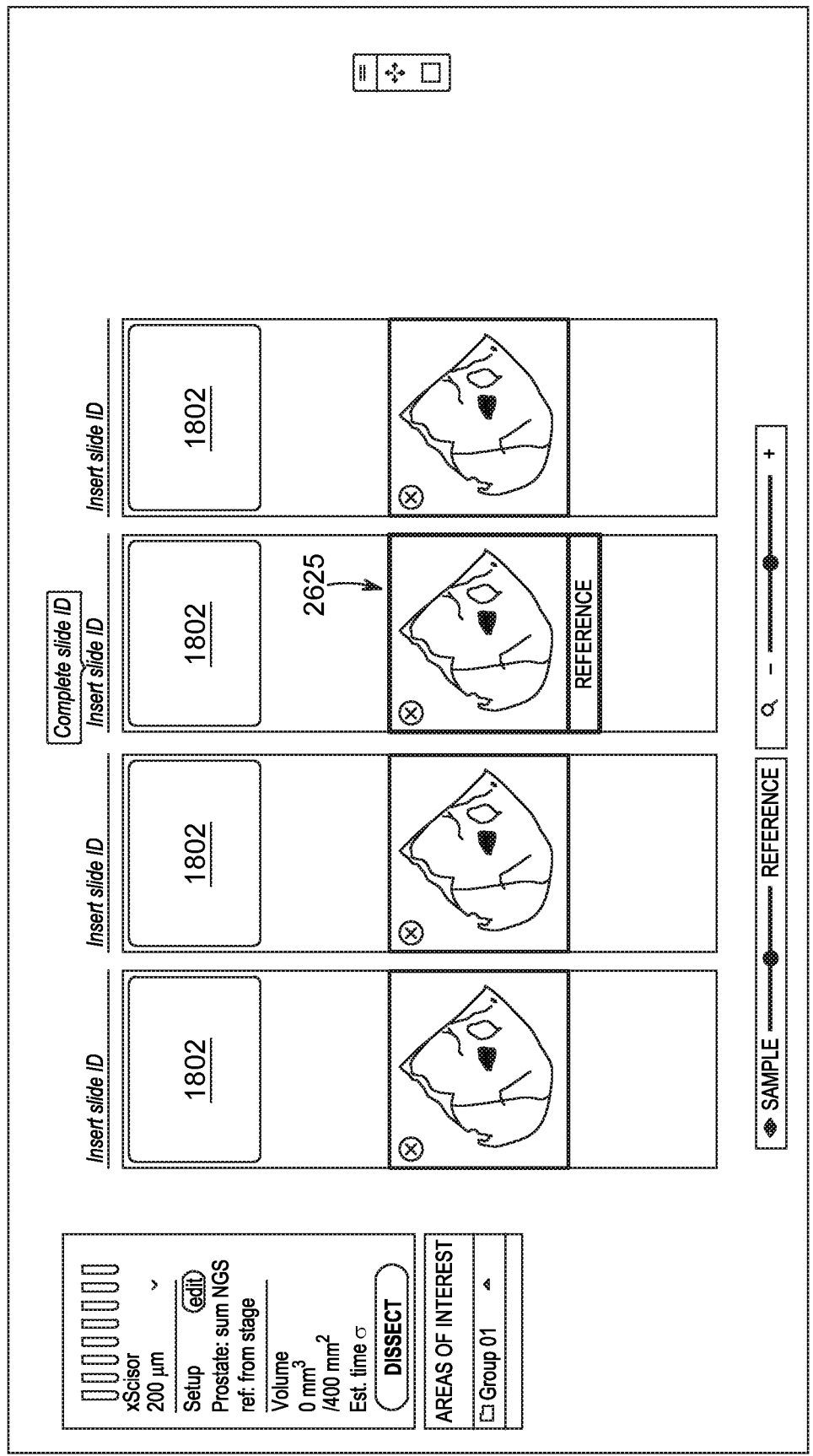
FIG. 27 illustrates an exemplary screen shot associated with a "Stage Overview" or "Stage Setup" step of the workflow of FIG. 25, according to an exemplary embodiment of the present disclosure.

FIG. 27 illustrates an exemplary screen shot 2700 associated with a "Stage Overview" or "Stage Setup" step of the workflow of FIG. 25, according to an exemplary embodiment of the present disclosure. The user ensures that the fill station reservoir 525 is loaded onto the load cell block 606 in order to monitor the buffer solution fill status (e.g., type, weight, volume).

The user fills the reservoir 525 with the desired buffer solution, and monitors the weight of the aqueous buffer solution in order to manage the dispensation of the buffer solution by means of the milling tip 600. The workflow 2500 will generate an error message in the event of an error in the fill volume, calibration error, etc. The workflow 2500 calibrates the fill station sensor within the load cell block 606 when the fill station 500 is filled with the customer buffer solution.

The user loads the desired number of milling tips 600 into the milling tip holders 420, 421, 422, 423, and further loads a corresponding number of collection vials 410 into the collection vial holders or wells 425. The workflow 2500 verifies the size and presence of the loaded milling tips 600. To this end, and for illustration purpose only, three different sizes of milling tips 600 can be used with the tissue dissection instrument 100, though other sizes can alternatively be selected. In the illustrated embodiment, the milling tips 600 are produced in three colors: Yellow, Green, and Blue that correspond to different sizes. As an example a yellow tinted milling tip 600 refers to the smallest size, the green tint refers to a medium size, while the blue tint refers to the largest size. The digital camera 321 acquires an image of the loaded milling tips 600, and the digital image is analyzed by the tissue dissection instrument 100, which recognizes and reports back on the presence and sizes of the loaded milling tips 600.

The following is a more detailed explanation of the step of recognizing the loaded milling tips 600. The tissue dissection instrument 100 is placed in a milling tip detection configuration: stage position, led brightness, zoom/focus/iris settings, backdrops (720, 721) retracted, and Z-axis actuator 810 in detection position.

Next, a digital detection image of the milling tips 600 is captured by the camera 321. In order to determine which pixels are in the detection ROI (region of interest), the user uses crosshair calibration to find the center of the milling tip 600 in the detection image, and uses scale calibration to crop out an approximately 3 mm radius ROI circle centered over the milling tip 600.

Each pixel within the detection ROI is then converted to hue, saturation, value (brightness), and chroma. The pixels are sorted by brightness, and the top 10% of the pixels are removed from the list, in order to help remove dust specks that may be on the glass window 814, which show up as bright spots in the detection image. The remaining pixels are then sorted by chroma, and the bottom 50% of these pixels are removed from the list, in order to remove dark pixels that are highly saturated, but do not have a reliable hue, leaving just the remaining most "colorful" pixels.

The tissue dissection instrument 100 then computes the average brightness of the remaining pixels. The tissue dissection instrument 100 can optionally compute the average hue of the remaining pixels, with the understanding that since hue is a circular quantity, simple averaging might not yield the optimal result. One alternative method would be as follows:

For each pixel treat the hue as an angle and compute the X, Y coordinates of that angle on a circle.
    Average the X components of all the pixels, and average the Y components of these pixels.
    Compute the angle that points to the average X coordinate, and the average Y coordinate, and use that angle to represent the average hue.

The tissue dissection instrument 100 determines if a milling tip 600 is not present as follows: If the average brightness of the pixels in the detection ROI (after above filtering) is less than the configured detection threshold, return a "No Milling Tip Detected" message.

Otherwise, the tissue dissection instrument 100 determines that a milling tip 600 is present and proceeds to determine the type of this milling tip 600, as follows: For each milling tip (600) type, the tissue dissection instrument 100 computes the difference between the average hue of the pixels in the detection ROI, and the configured hue for the milling tip type, again accounting for the circular nature of hue. The tissue dissection instrument 100 then returns the type of the milling tip 600 with the closest hue to the average of the pixels in the detection ROI.

The user enters the dissection path for multiple collection vials 410. Based on the dissection settings for the milling tip (600) size, sample type, or tissue thickness, the workflow 2500 will assign the weight to be applied onto the milling tip head too to the glass window 814, by the Z-axis actuator assembly 810.

The tissue dissection instrument 100 further verifies the presence or absence of the sample collection vials 410. To this end, the glass windows 810 is located beneath the sample collection vials, through which the camera 321 acquires a photo of the position of the sample collection vials 410. If this position is blocked, the tissue dissection instrument 100 reports that the presence of a sample collection vial 410. Otherwise, if the tissue dissection instrument 100 reads the clear backlight (i.e., it is not blocked), it reports that no sample collection vial 410 is present.

The workflow 2500 continues by reporting if there is enough buffer solution within the fill station 500 to complete the number of dissections and milling tips 600 required for a dissection run, and if needed, it will prompt the user to fill the reservoir 525 with buffer solution. The workflow 2500 will generate an error message in the event of an error with a buffer draw. In addition, the workflow 2500 will continuously monitor the dispensation of the buffer solution as it is withdrawn to fill the milling tip 600.

The tissue dissection instrument 100 verifies that the dissection buffer solution has been collected by the milling tip 600, as follows: when the milling tip 600 is drawing buffer solution from the fill station 500, the load cell block 606 monitors the reduction in the overall weight of the reservoir 525, as the liquid buffer solution is drawn from the fill station 500 and loaded into the milling tip 600. In an exemplary embodiment, the tissue dissection instrument 100 is configured to monitor a change in the weight of the reservoir 525 greater than 350 ul or 0.35 g.

FIG. 28 represents another exemplary screen shot 2800 associated with the stage overview step 2535 of the workflow 2500 of FIG. 25, for a monitoring and collecting dashboard according to an exemplary embodiment of the present disclosure. The dashboard shows one yellow tinted (i.e., small sized) milling tip 600 present in the first position (i.e., first leftmost position), that is loaded in the first holder 420. As an example, this milling tip 600 is filled with 250 um of buffer solution. In addition, the dashboard also shows that one corresponding (i.e., yellow tinted) collection vial 410 is present and inserted in the first (i.e., leftmost) vial collection well 425.

Figure 29:
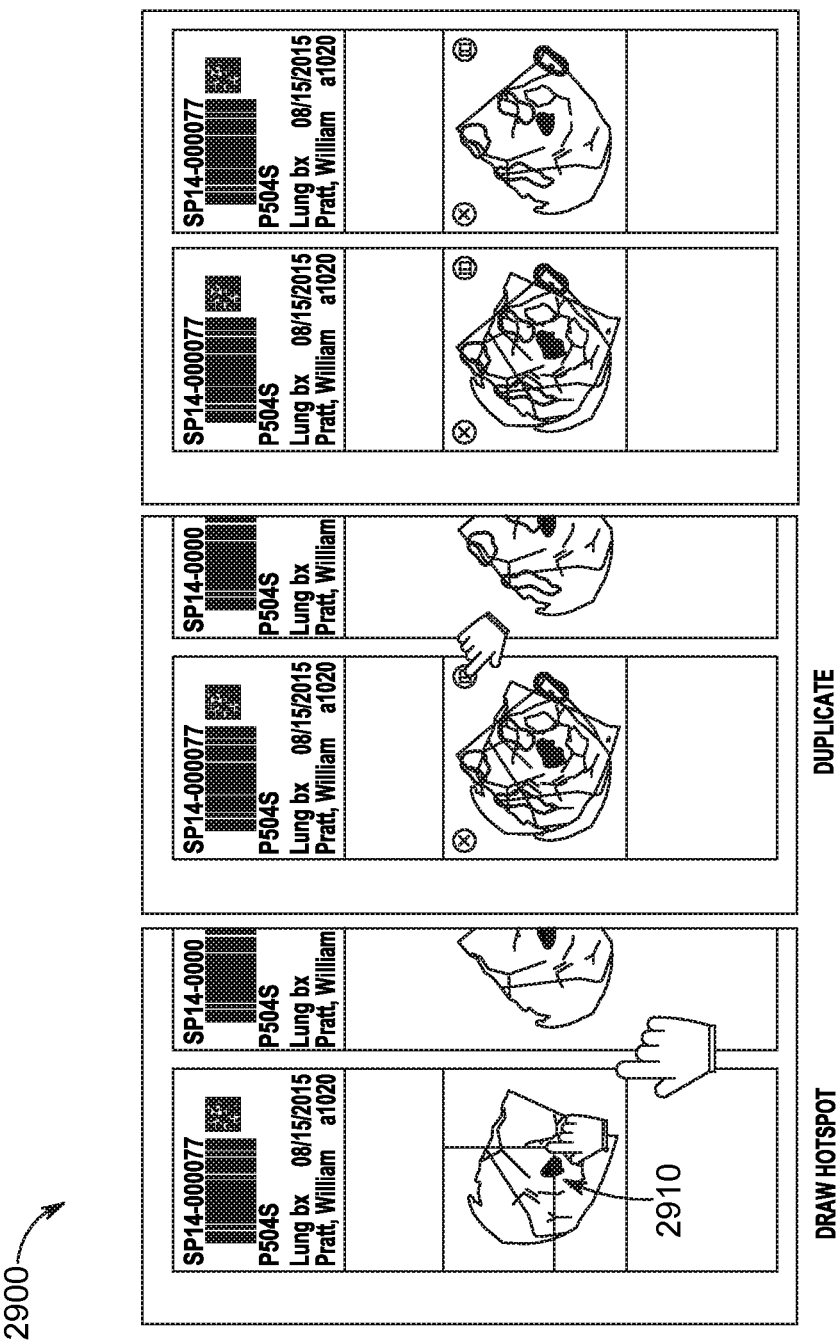
FIG. 29 represents an exemplary screen shot associated with a "Sample View" step of the workflow of FIG. 25, according to an exemplary embodiment of the present disclosure.

FIG. 29 illustrates an exemplary screen shot associated with a "Sample View" step 2540 of the workflow 2500 of FIG. 25, according to an exemplary embodiment of the present disclosure. The user has the ability to import a digital reference image 2625 that may have been pre-stored in a database (or the workflow 2500 retrieves it automatically from the LIS). In the event that the reference slide 2625 is mounted on the stage 400, the user has the ability to capture a low resolution reference image, and thus leaves the "Import Reference" field blank in the corresponding setup page.

The user loads four sample slides 465, 466, 467, 468 (also collectively referred to with the numeral reference 405) in position onto the top slide frame 815 of the stage 400. If the sample slides 465, 466, 467, 468 do not have barcodes, the user has the chance to input them here. This information will be included in the final report.

At this step 2540, the user can create, delete, or duplicate "hotspots" on the reference slide 2625. As used herein, the term "hotspots" refers to the sections of the tissue sample that needs to be captured in a higher resolution. The hotspots are also status indicators and they indicate if the tissue has been captured or not, and if the user checked the alignment and areas of interest on each tissue sample 406.

From this view, the user can define which samples he or she wishes to dissect. In a scenario where a hotspot overlaps over the target volume, the user can simply remove the overlapping hotspot. If the auto detection fails to recognize the tissue correctly, the bounding can be transformed. If no tissue is detected, the user can draw the first hotspot 2910 for duplication onto the loaded samples loaded on the sample slides 465, 466, 467, 468.

Figure 30:
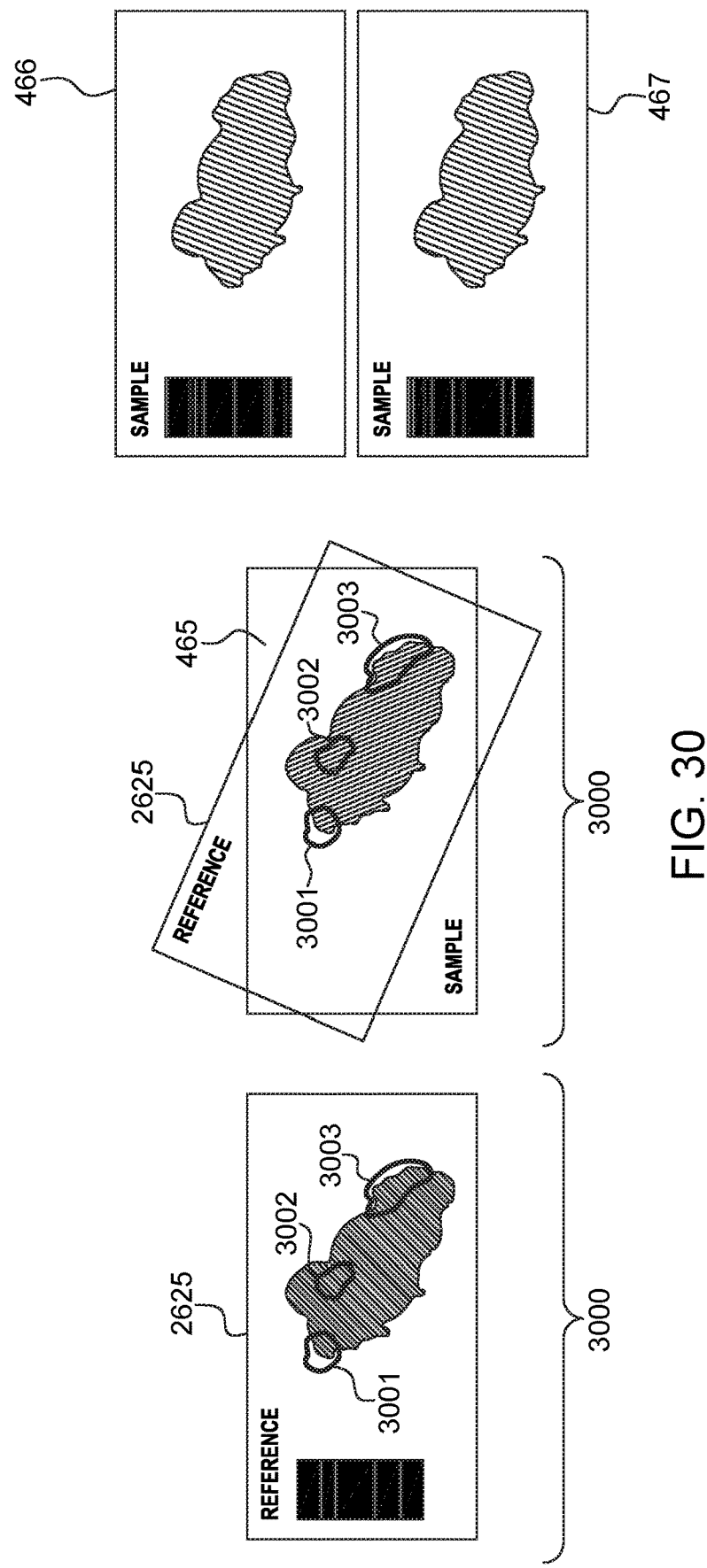
FIGS. 30 and 31 represent screen shots associated with the steps of the workflow of FIG. 25, for respectively aligning the reference slide with the various sample slides, and for drawing or annotating the areas of interest, according to an exemplary embodiment of the present disclosure.
Figure 31:
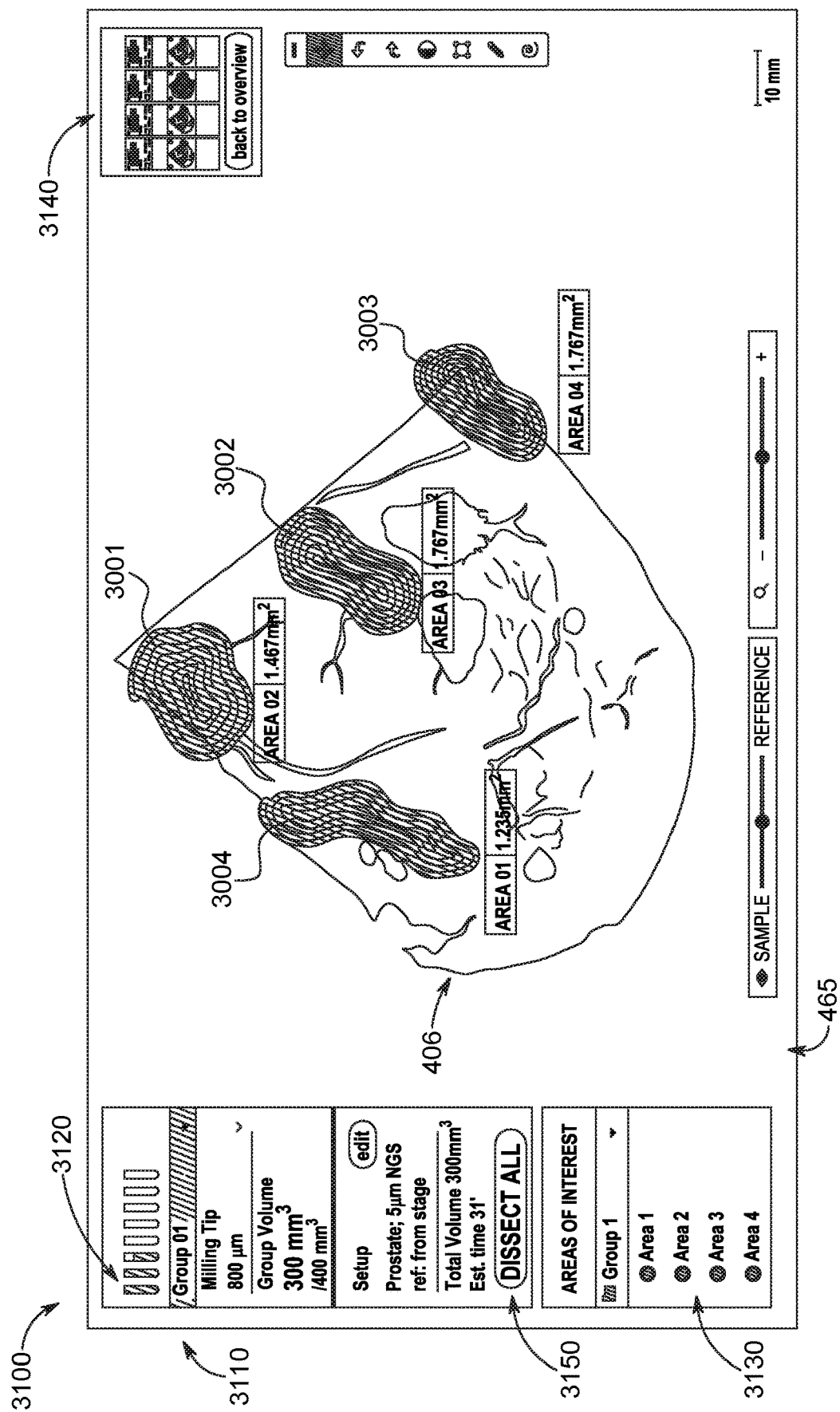

FIGS. 30 and 31 further illustrate the steps 2545 and 2550 of the workflow 2500 for respectively aligning the reference slide 2625 with the various sample slides 465, 466, 467, and for drawing or annotating the areas of interest ("AOIs"), according to an exemplary embodiment of the present disclosure. For further clarity, in an exemplary illustration, the reference slide 2625 can be the first cut of an FFPE block that has an H&E stain. The reference slide 2625 Is reviewed by a pathologist who annotates the areas of interest to dissect. The reference slide can be equated to a map with coordinates that identify the areas of interest 3001, 3002, 3003, 3004 (collectively referred to as AOI or AOIs 3000). The reference slide 2625 can either be an imported image from a scanner or an image captured from the stage 400. The reference slide 2625 is then aligned to the tissues on the serial slides, which is a crucial step to identify the AOIs 3000.

As the sequential cuts are not usually reviewed by the pathologist, the reference image or slide 2625 is key to finding the equivalent areas in the subsequent tissues on the sample slides 465, 466, 467, 468. The objective is to collect as much volume of the tissue sample 406 as possible from the AOIs, to be analyzed in various downstream applications.

The tissue samples 406 are the sequential cuts were the tissue is collected. These samples 406 are physically loaded on the tissue sample slides 465, 466, 467, 468 onto the stage 400, and the software utilized by the present exemplary embodiment cannot transform or alter these samples 406, other than provide image contrast. Once the reference slide is aligned with the first tissue sample slide 465, the AOIs 3000 are subsequently transferred on to the remaining sample slides 466, 467, 468 by the software of workflow 2500.

The transfer and alignment of the reference slide image onto the sample slides 465, 466, 467, 468 can be done manually by the user or automatically by the workflow 2500. An exemplary method of effecting such transfer is described for example in patent application, publication No. WO 2016120433A1, which is incorporated herein in its entirety by this reference, and which generally describes a clinical workflow for meso-dissection of biological specimens and tissue slides by incorporating annotation and inter-marker registration modules within digital pathology imaging and meso-dissection (or milling) systems. Images of a reference slide a milling slide may be acquired using the same imaging system, with the annotations on the image associated with the milling slide being based on the inter-marker registration. Each image along with its respective annotations and meta-data may be associated with a project or a case, and stored in an image management system. A same-marker registration may be used to map annotations from the annotated image of the milling slide to a live image of the milling slide. The milling slide may be milled based on the annotations, with milled tissue output into a contained that is labeled in association with the labeled input slides.

FIG. 31 illustrates a screen shot 3100 that shows the various AOIs 3001, 3002, 3003, 3004 (or 3000) projected onto the tissue sample slide 465. At this stage, the user can fine tune the alignment of the AOIs 3000 and annotate the tissue sample 406. In addition, if automation is in place, this will be a quick review that everything is aligned and dissection is ready to be initiated, or to revise the dissection path and volume (step 2555 of the workflow 2500).

The dashboard illustrated in the screen shot 3100 further provides the user with a dissection information panel 3110 that offers a visual indication of the buffer solution consumption and the target volume. In this exemplary illustration, an indicator 3120 shows approximately two and a third (2.33) vials being filled, which reflects the desired volume of the buffer solution to be collected in the first three collection vials 410. In this illustration, each milling tip 600 has a capacity of approximately 800 um, with a group total volume of 300 mm$^3$.

The dashboard illustrated by the screen shot 3100 also provides the user with an AOI panel 3130 that reflects the four AOIs 3000 to be excised. The dashboard also provides a navigator panel 3140, which enables the user to select and click on the hotspot of choice to advance to the next sample or to return to a previous sample for overview. A "Dissect All" key 3150 can be pressed by the user once the user is satisfied that the entire setup is complete and the excision process can proceed.

Figure 32:
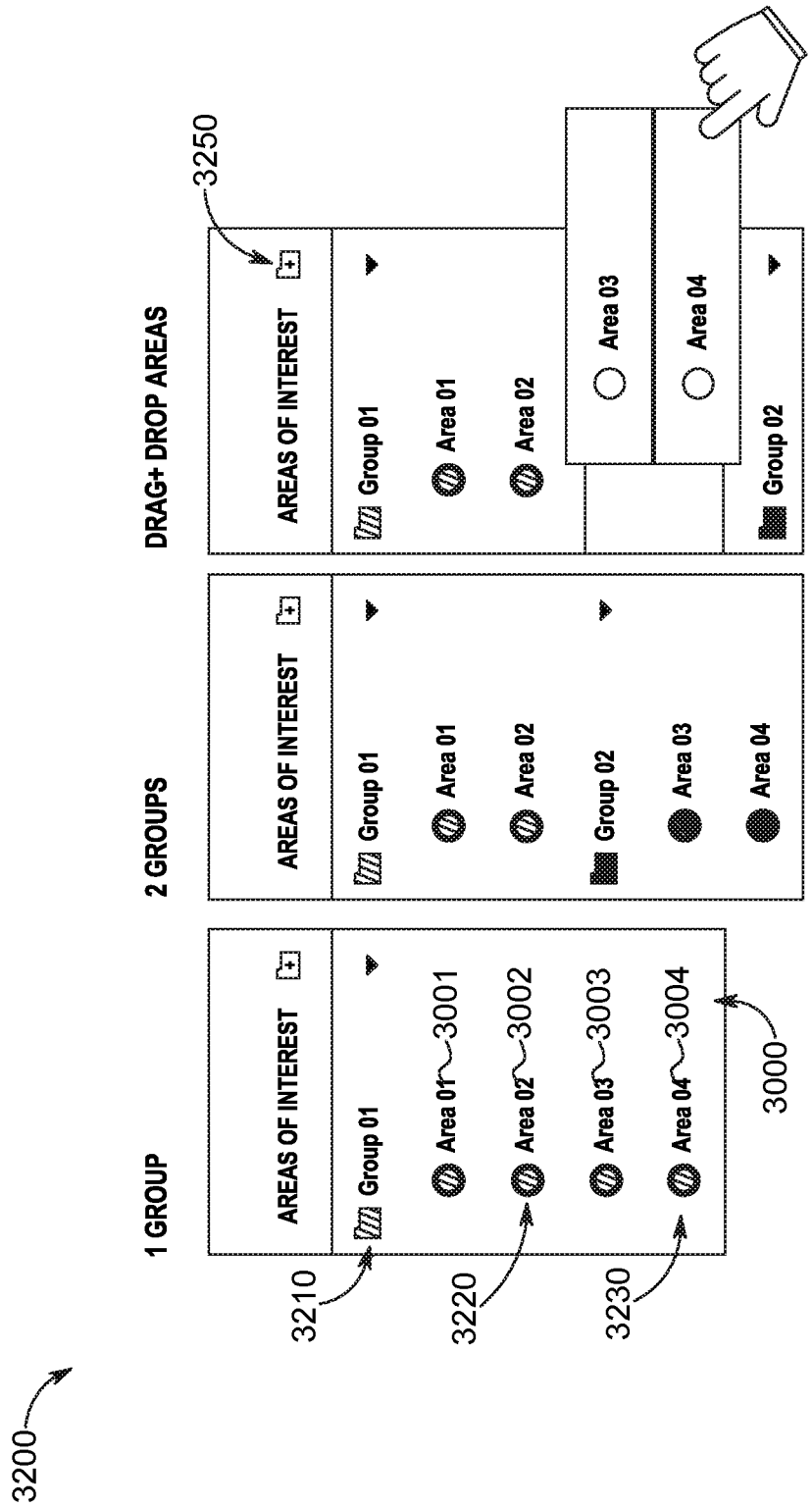
FIG. 32 represents a screen shot of an AOI panel according to an exemplary embodiment of the present disclosure.

FIG. 32 represents a screen shot 3200 of an AOI panel according to an exemplary embodiment of the present disclosure. The AOI panel provides the user with the ability to visually determine how many areas of interest are recognized by the tissue dissection instrument 100, as well as the ability to rename and change the color and grouping of each area of interest 3000.

As an example, by double clicking or long pressing the "Group 01" icon 3210, the user has the ability to rename Group 01 and to change its color. By selecting or unselecting the "Area 02" icon 3220, the user has the ability to view the dissection path for the AOI 3002, as an outline. By right clicking the "Area 04" icon 3230, the user has the ability to delete or remove the particular AOI 3004. By clicking the "AREAS OF INTEREST" icon 3250, the user has the option to add a new AOI group or a new area of interest.

Figure 33:
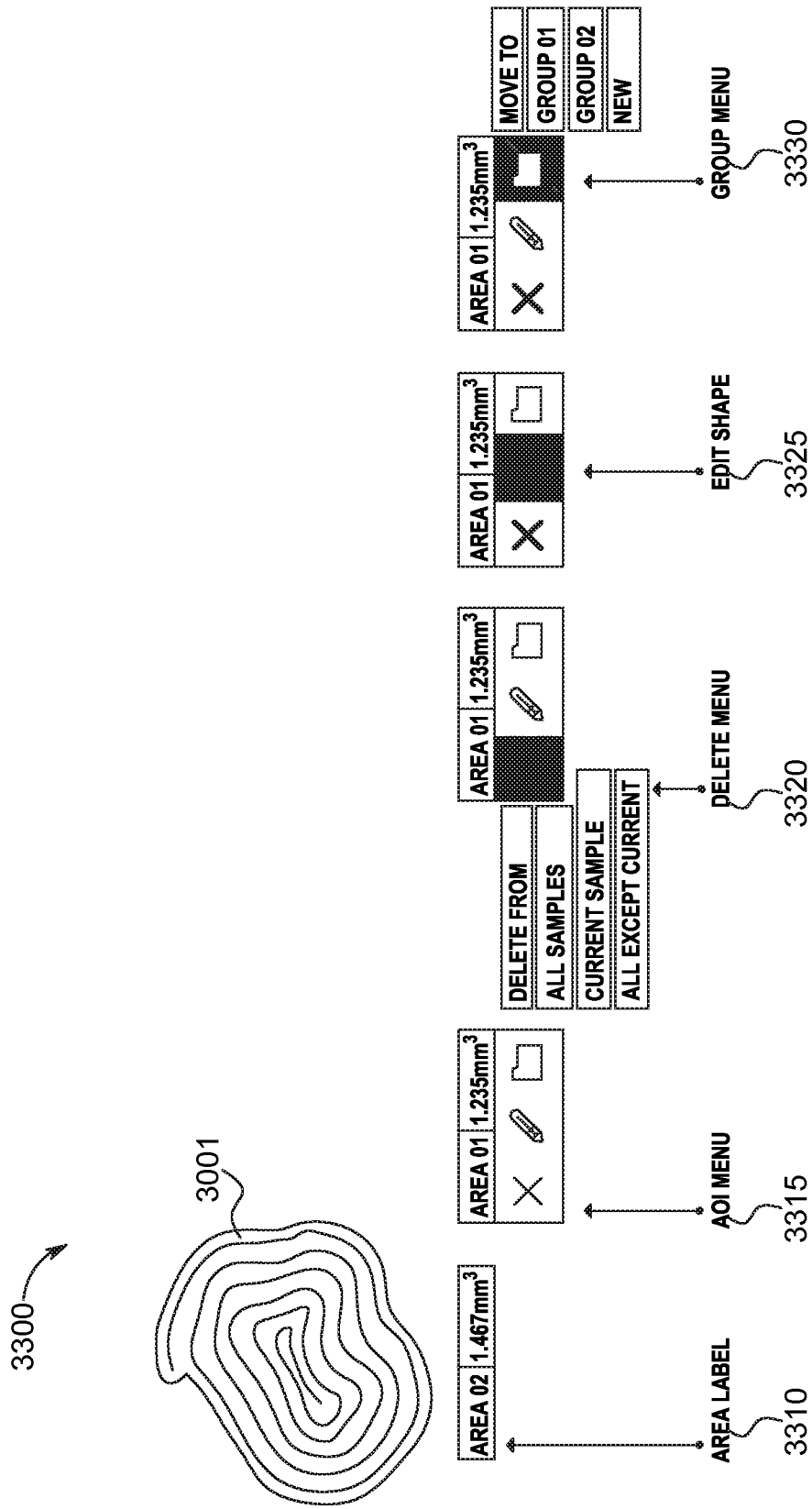
FIG. 33 represents a screen shot of an "AOI—Menu States" panel according to an exemplary embodiment of the present disclosure.

FIG. 33 represents a screen shot 3300 of an "AOI—Menu States" panel according to an exemplary embodiment of the present disclosure. This panel provides the user with a detailed view of the settings of each individual AOI 3001, and with the ability to selectively refine these settings. As an example, the panel provides the user with an area label 3310, an AOI menu 3315, a delete menu 3320, an edit shape menu 3325, and a group menu 3330.

Figure 34:
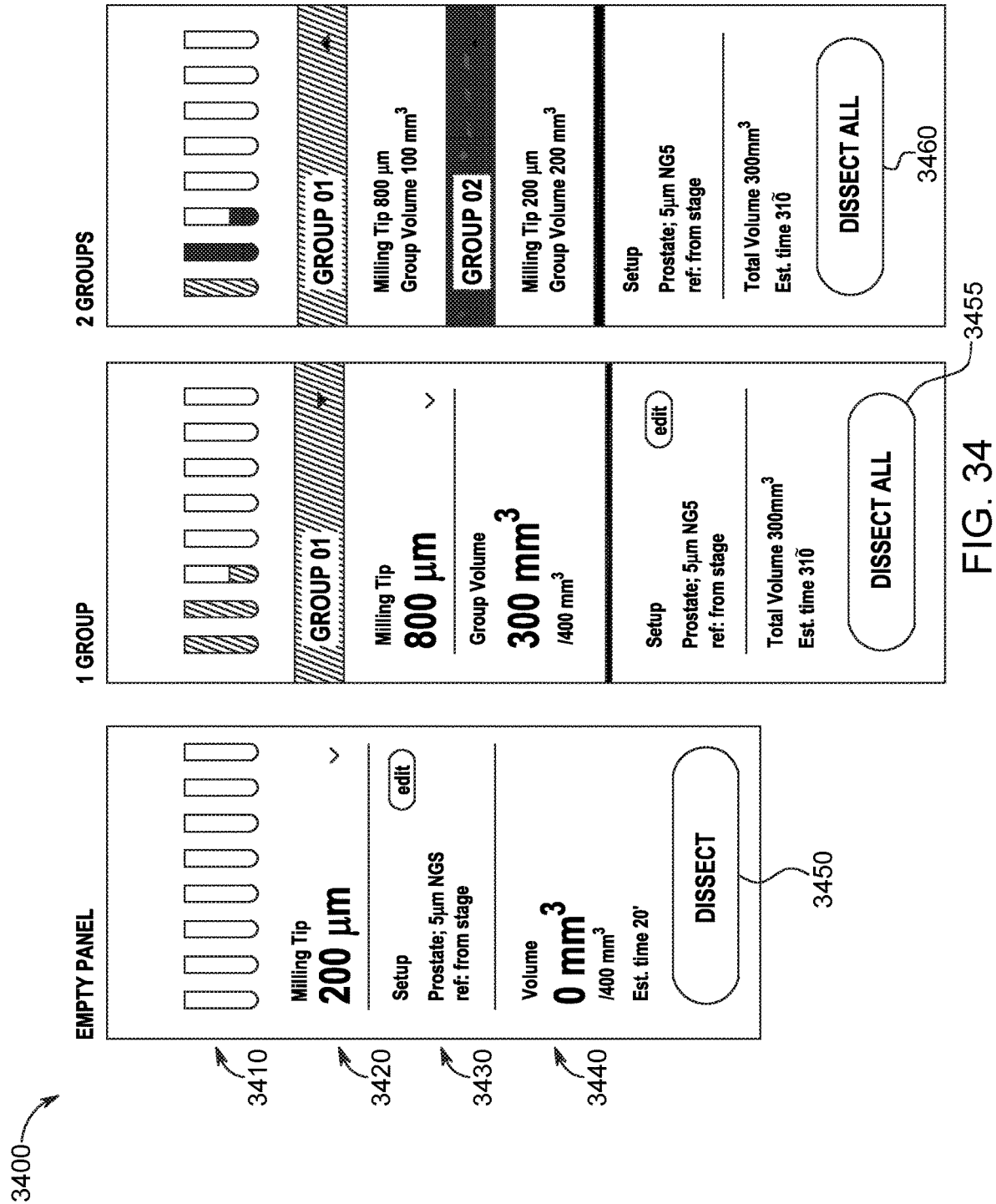
FIG. 34 represents a screen shot of a "Dissection Info" panel according to an exemplary embodiment of the present disclosure.

FIG. 34 represents a screen shot 3400 of a "Dissection Info" panel according to an exemplary embodiment of the present disclosure. This panel provides the user with the following: a visual indicator 3410 of each milling tip 600 consumption of buffer solution; a drop down menu that provides details about the milling tips 600 that affect the dissection path; a setup selection key 3430 that returns the user to the setup page; a volume indicator 3440 that provides the user with a real time volume estimation of the buffer solution; and with a plurality of "Dissect" keys 3450, 3455, 3460 that selectively initiate the dissection of the group or groups of choice.

Figure 35:
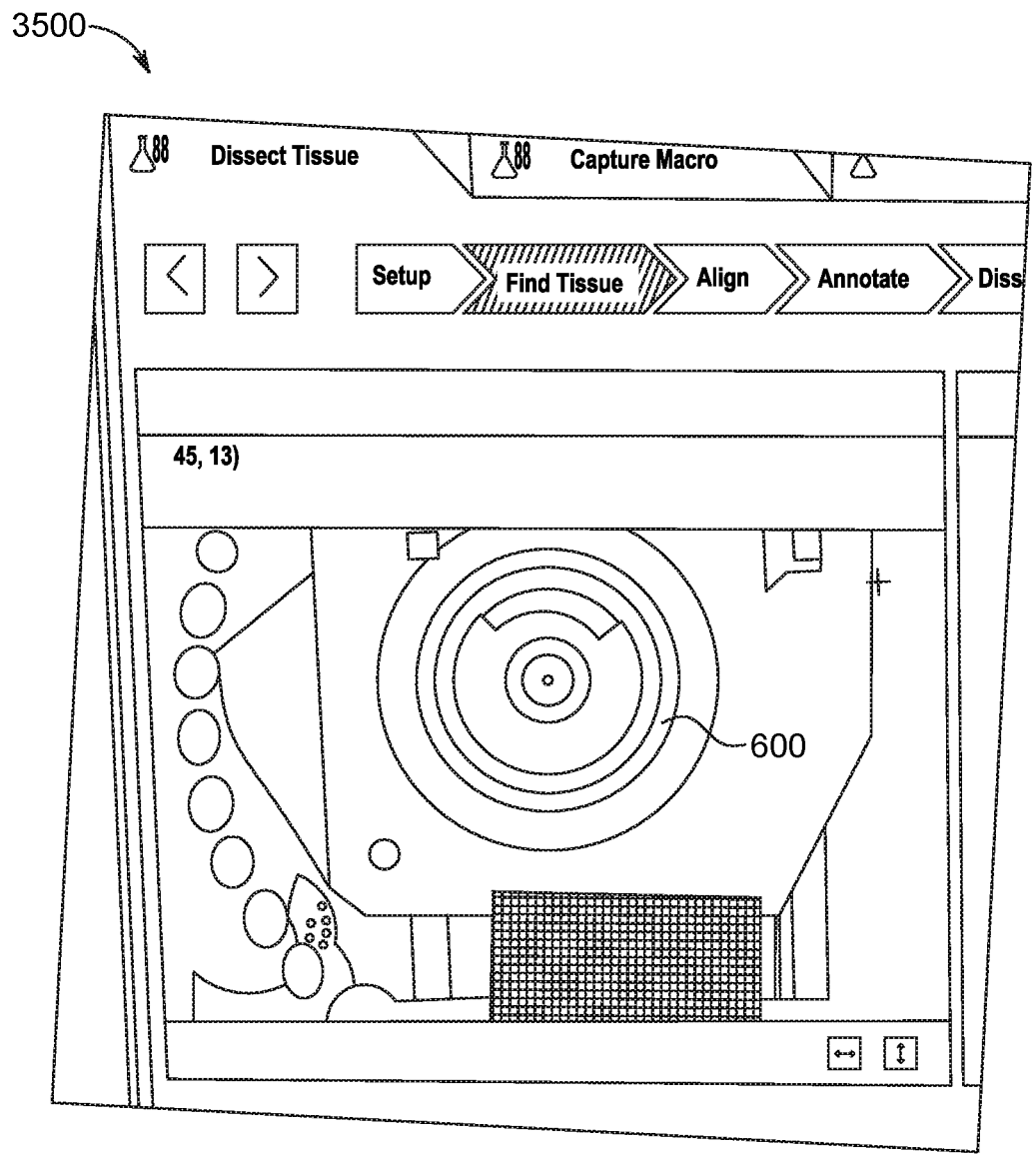
FIG. 35 represents a camera shot of a milling tip upon initiation of a "Dissect" function of the workflow, according to an exemplary embodiment of the present disclosure.

Once all the milling tips 600 and the are loaded into the tip holders 420, 421, 422, 423; the collection vials 410 are loaded in their corresponding wells 425; the proper buffer solution is filled in the fill station 500; and the AOIs 3000 selected, the user can press any one of the "Dissect" keys 3450, 3455, 3460 to selectively initiate the dissection step 2555 of the workflow 2500. In response, the head assembly 800 will pick up the first milling tip 600 at the tip holder 420 and will move the milling tip 600 to the field of view of the camera 321. FIG. 35 represents a camera shot 3500 of the milling tip 600 upon initiation of a "Dissect" function (step 2555) of the workflow 2500.

As explained earlier, the software or workflow 2500 uses a color recognition algorithm to determine if the correct milling tip 600 is loaded (i.e., presence and size). If the finding is acceptable to the user, the tissue dissection instrument 100 automatically moves the milling tip 600 to the fill station 500 to load the milling tip 600 with the buffer solution. The workflow 2500 monitors if enough buffer solution was drawn by monitoring the weight change of the fill station 500 (or the reservoir 525).

The tissue dissection instrument 100 then performs a serial dissection on multiple sample slides 405 and annotated the regions. If the following has not already been confirmed, once the dissection is complete, the camera 325 moves to the collection vial wells 425 and the tissue dissection instrument 100 confirms the presence of absence of a collection vial 410. If the collection vial 410 is present, the tissue dissection instrument 100 dispenses the content of the milling tip 600 (i.e., mixture of buffer solution and collection tissues 406) into the collection vial 410. The tissue dissection instrument 100 repeats the foregoing dissection step until all the desired tissue samples 406 have been excised.

Figure 36:
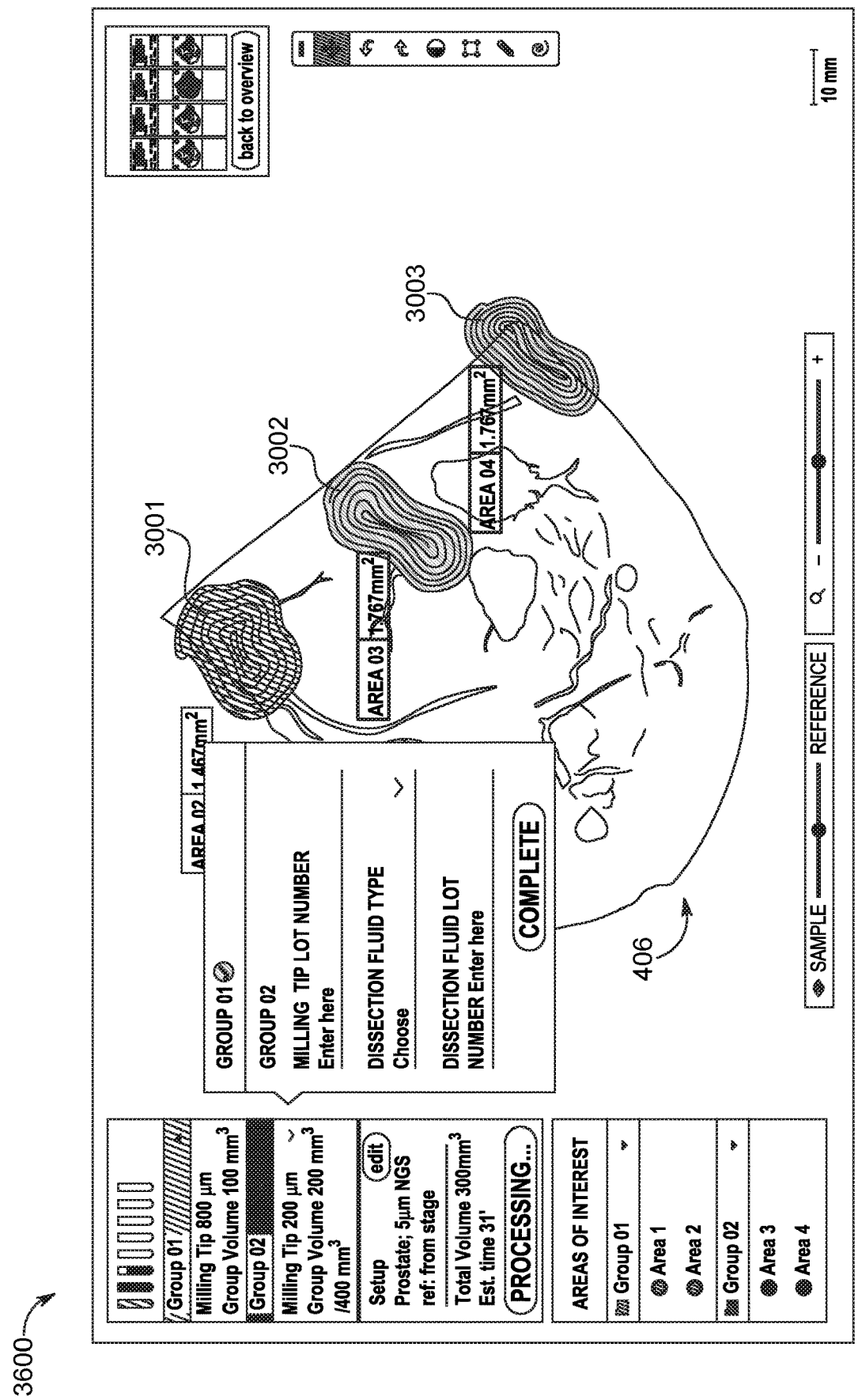
FIG. 36 represents a screen shot that illustrates the initiation of the dissect function, according to an exemplary embodiment of the present disclosure.

FIG. 36 represents a screen shot 3600 that illustrates the initiation of the "Dissect" function. The screen shot 3600 shows the assignment of the various AOIs 3000 and their respective distribution over the designated groups. As an example, AOI 3001 and AOI 3004 (FIG. 37) are assigned to Group 01, with a blue color identification to indicate that the associated milling tip 600 has a larger capacity. AOIs 3002 and 3003 on the other hand, were assigned to Group 02, with a green color identification to indicate that the associated milling tip 600 has a medium capacity. In addition, the panel enables the user to add the lot numbers and buffer solution information even after the user has already initiated the "Dissect" function.

Figure 37:
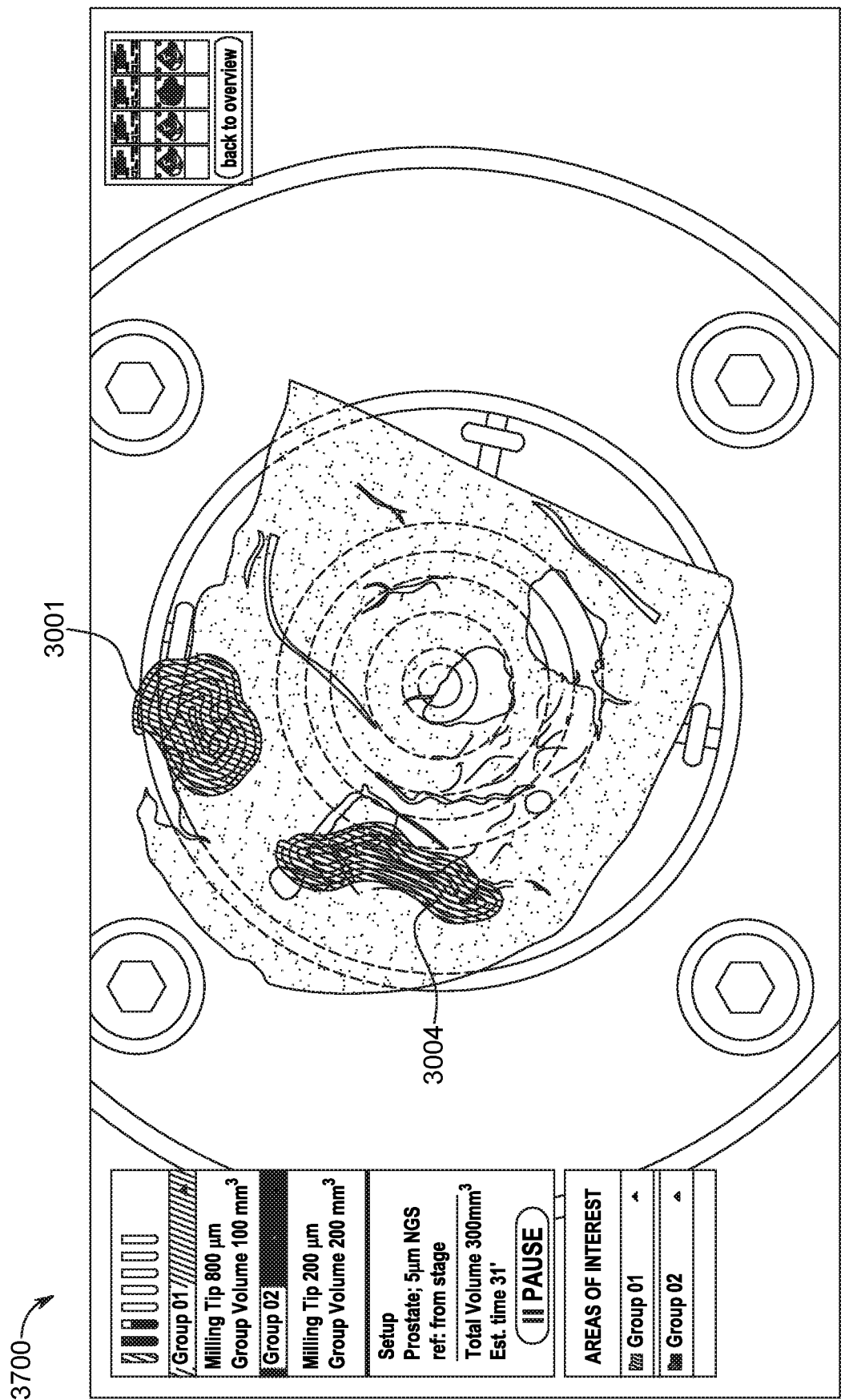
FIG. 37 represents a camera shot (or image) showing the removal of the AOIs assigned to one of the AOI groups, according to an exemplary embodiment of the present disclosure.

FIG. 37 represents a camera shot 3700 showing the removal of the AOIs 3002, 3004 that are assigned to AOI Group 02 (green colored), with the AOIs 3001, 3002 remaining.

Figure 38:
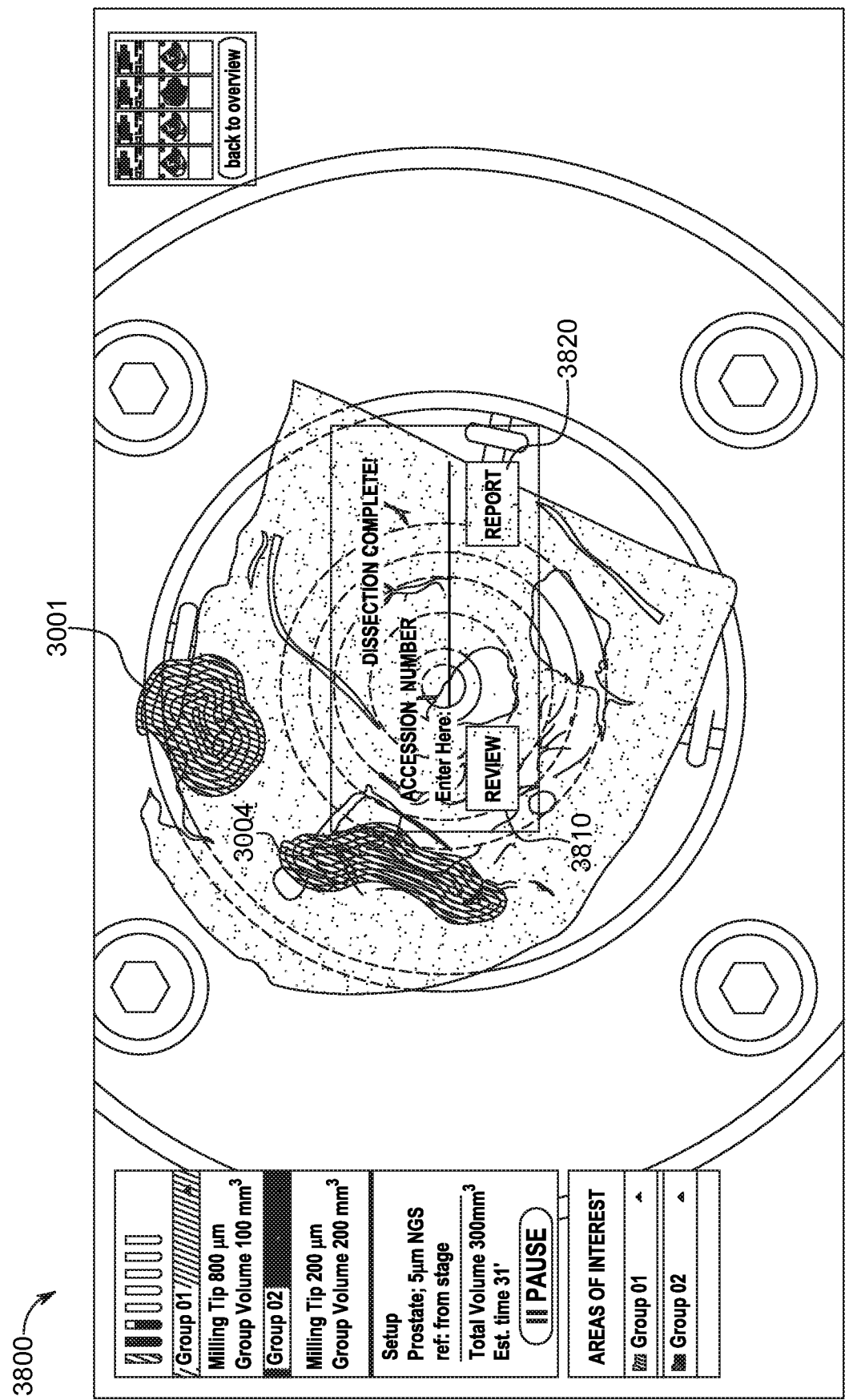
FIG. 38 is another representation of the camera shot of FIG. 37, after the user has paused or stopped the dissection process, according to an exemplary embodiment of the present disclosure.

FIG. 38 is another representation of the camera shot 3700 after the user has paused or stopped the dissection process, giving the user two options: either rework (3810) to pick up the leftover tissue (AOIs 3001, 3004), or complete the dissection and report the findings (3820). The user has the option to enter the accession number.

Figure 39:
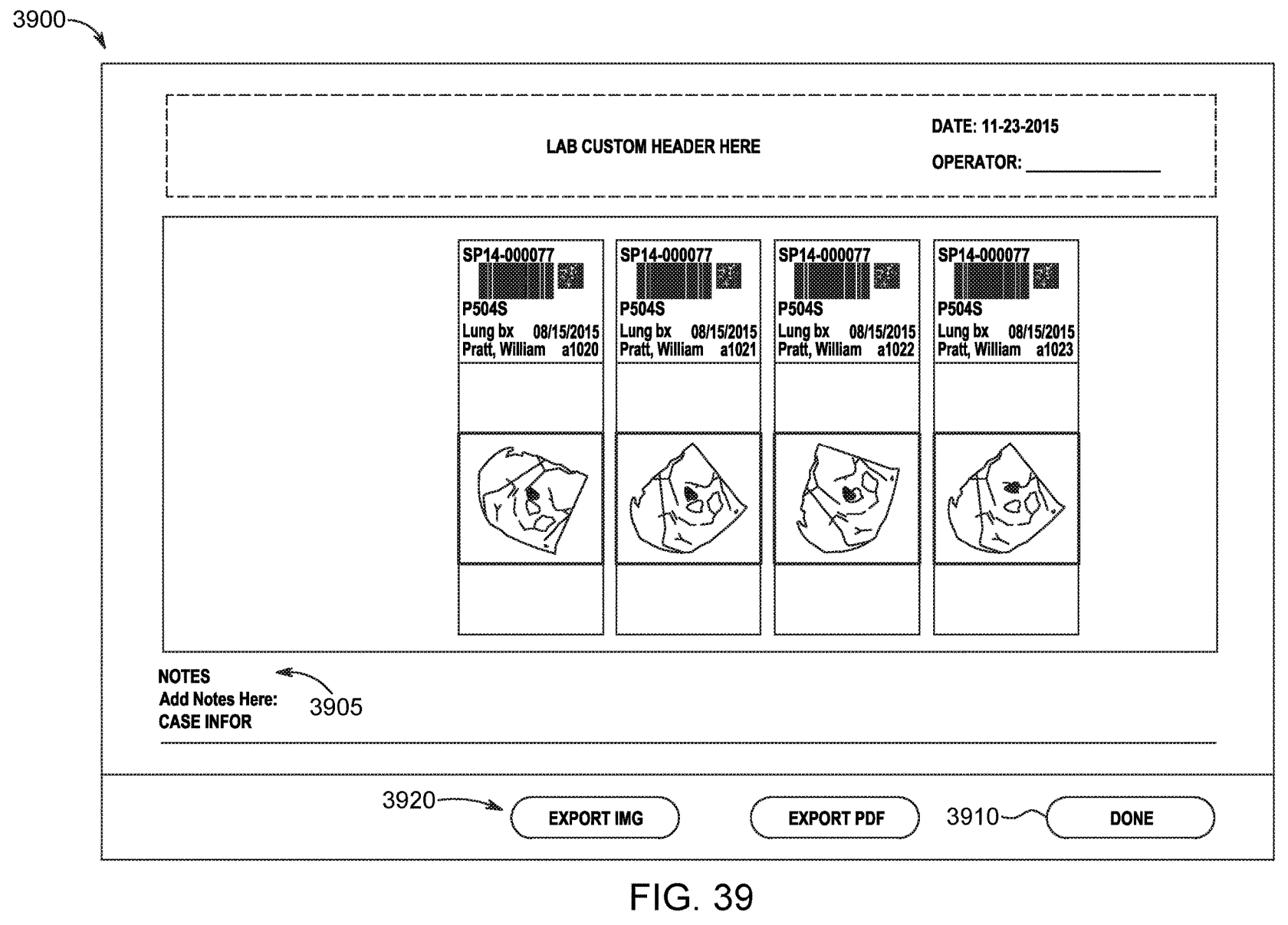

FIG. 39 represents a screen shot 3900 of the final report that is prepared according to an exemplary embodiment of the present disclosure. The report 3900 records as many actions of the workflow 2500 as possible, including the overview, hotspots, tracking ID numbers, and the AOIs 3000 that were dissected. The final report provides the user with the options to enter additional notes 3905, return to the case list by pressing the "Done" key 3910, and to export the report in one of several formats 3920.

The sample tracking procedure 2560 of workflow 2500 is automatically performed by the tissue dissection instrument 100 that records the following metadata:
  User: who performed the dissection task.
  Reagents used: User enters buffer information, Milling tip lot number.
  Case information: Records patient information, order information, pathologist and case notes.
  Images of the reference slide 2625 used to transfer the annotations: Stores an image of the reference slide 2625. The image is available as a TIF file and is reported in the final sample report 3900. Reference images may be imported from an outside digital pathology system or scanned live on the stage.
  Before and after dissection events are recorded: Key steps within the process are recorded. During the dissection process the tissue sample 406 is taken from the sample slide 405. Images of the sample slide 405 are acquired prior and after the dissection process. The post dissection image is of the actual dissection. The following images are taken during the dissection process:
    Reference image: digital image of the imported or annotated image.
    Annotations: The annotations drawn on the sample slide.
    Milling path: The milling path the system calculated to perform on the slide.
  A sample report: the sample reports presents all information pertinent to the sample to include: User, reagents, images of the slides, dissection area collected, sample collection numbers and site information.

Figure 40:
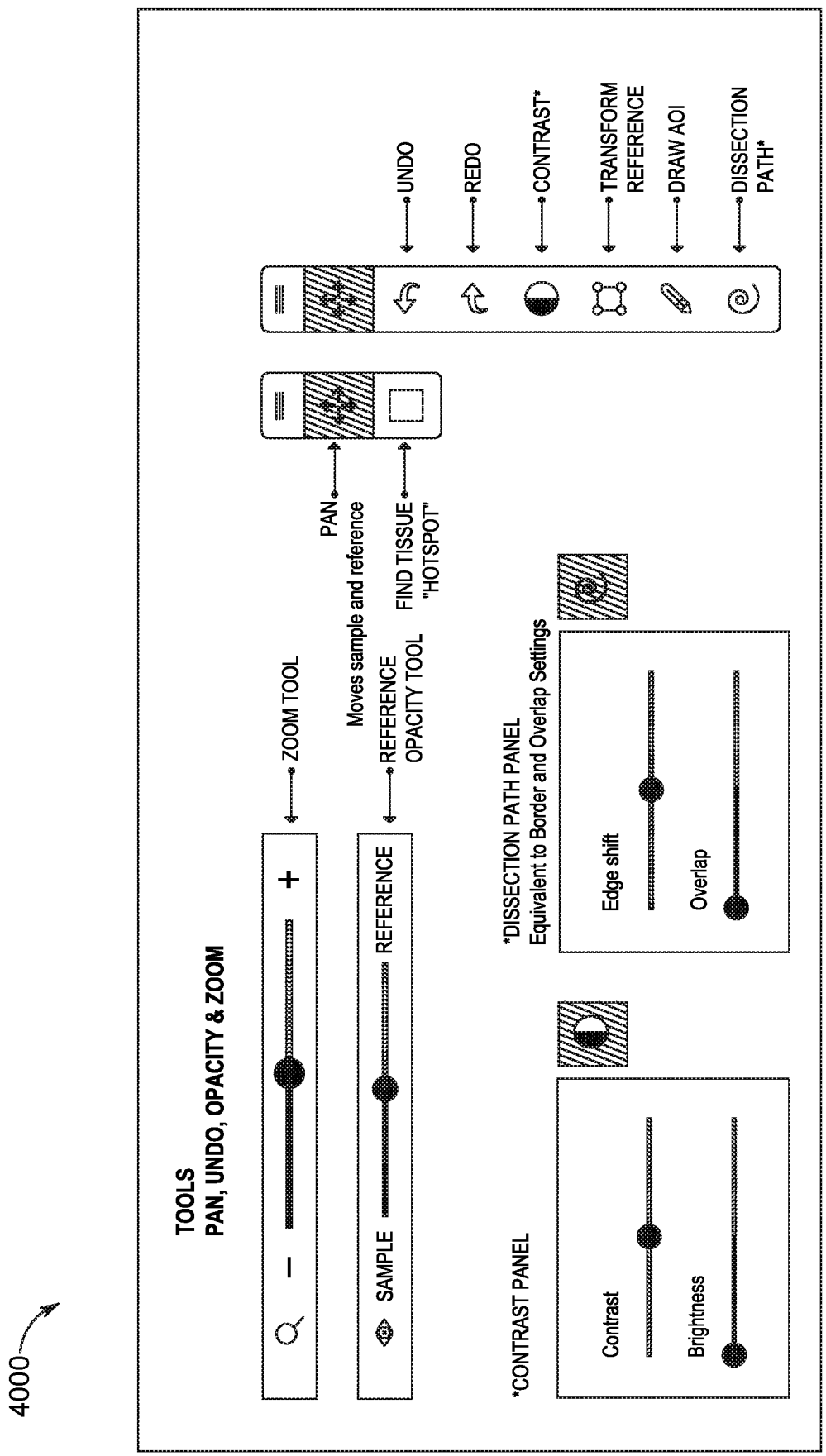
FIGS. 40, 41, 42 represent screen shots of various tools that are available to a user during the operation of the tissue dissection instrument, according to an exemplary embodiment of the present disclosure.
Figure 41:
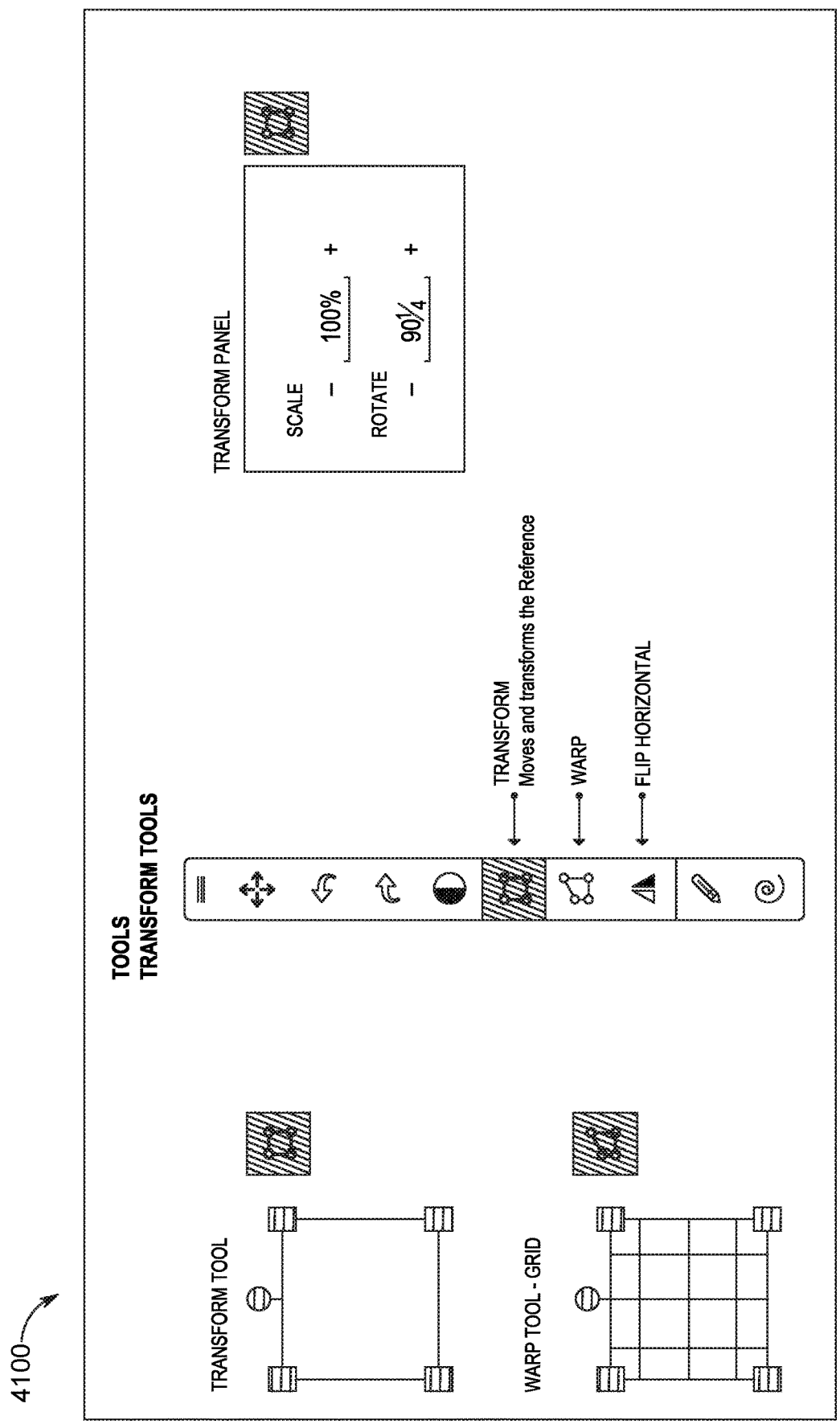
Figure 42:
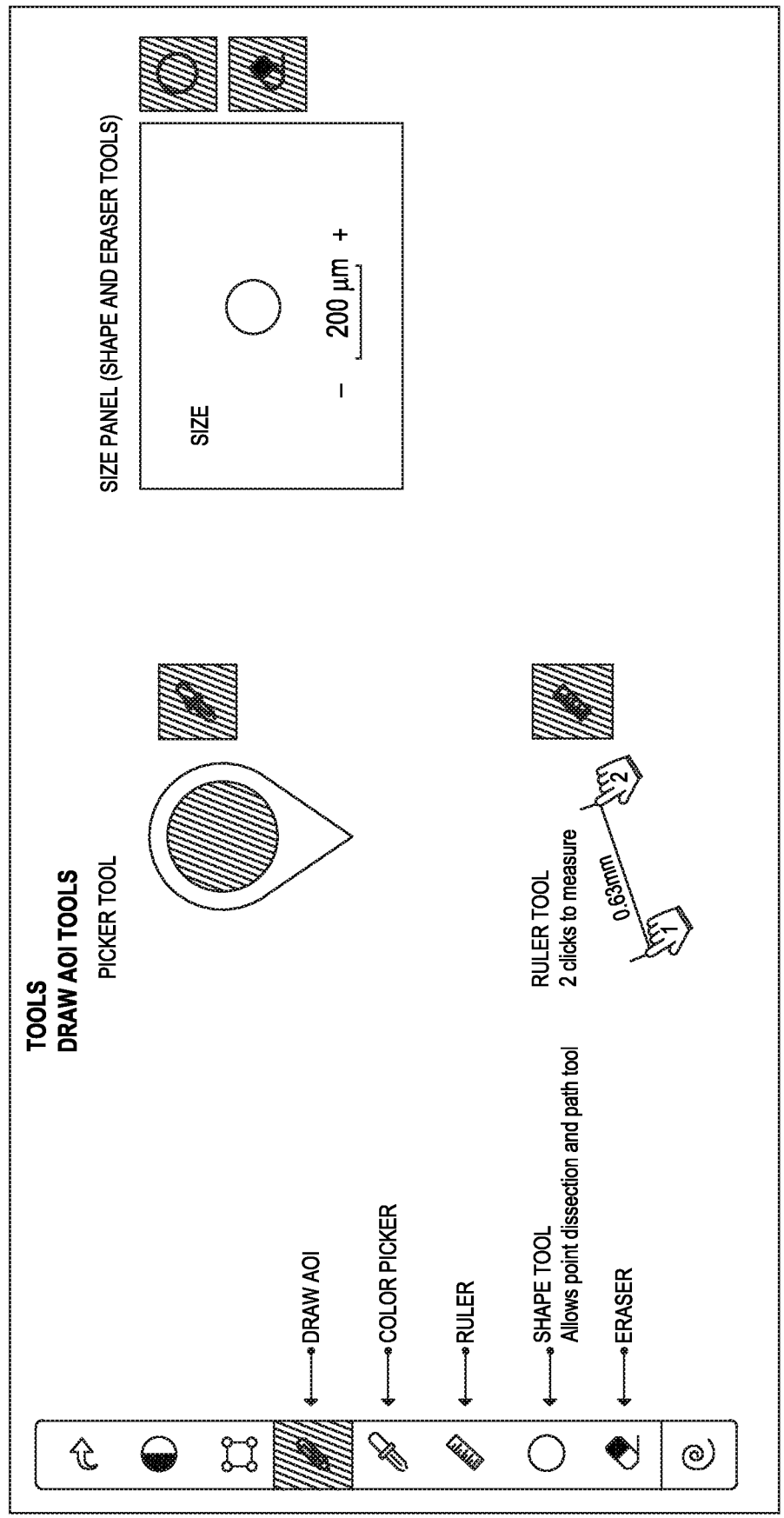

FIGS. 40, 41, 42 represent screen shots 4000, 4100, 4200, respectively of various tools that are available to a user during the operation of the tissue dissection instrument 100. FIG. 40 illustrates the pan, undo, opacity, and zoom tools. FIG. 41 illustrates the transformation tools. FIG. 42 illustrates the drawing and AOI tools.

Figure 43:
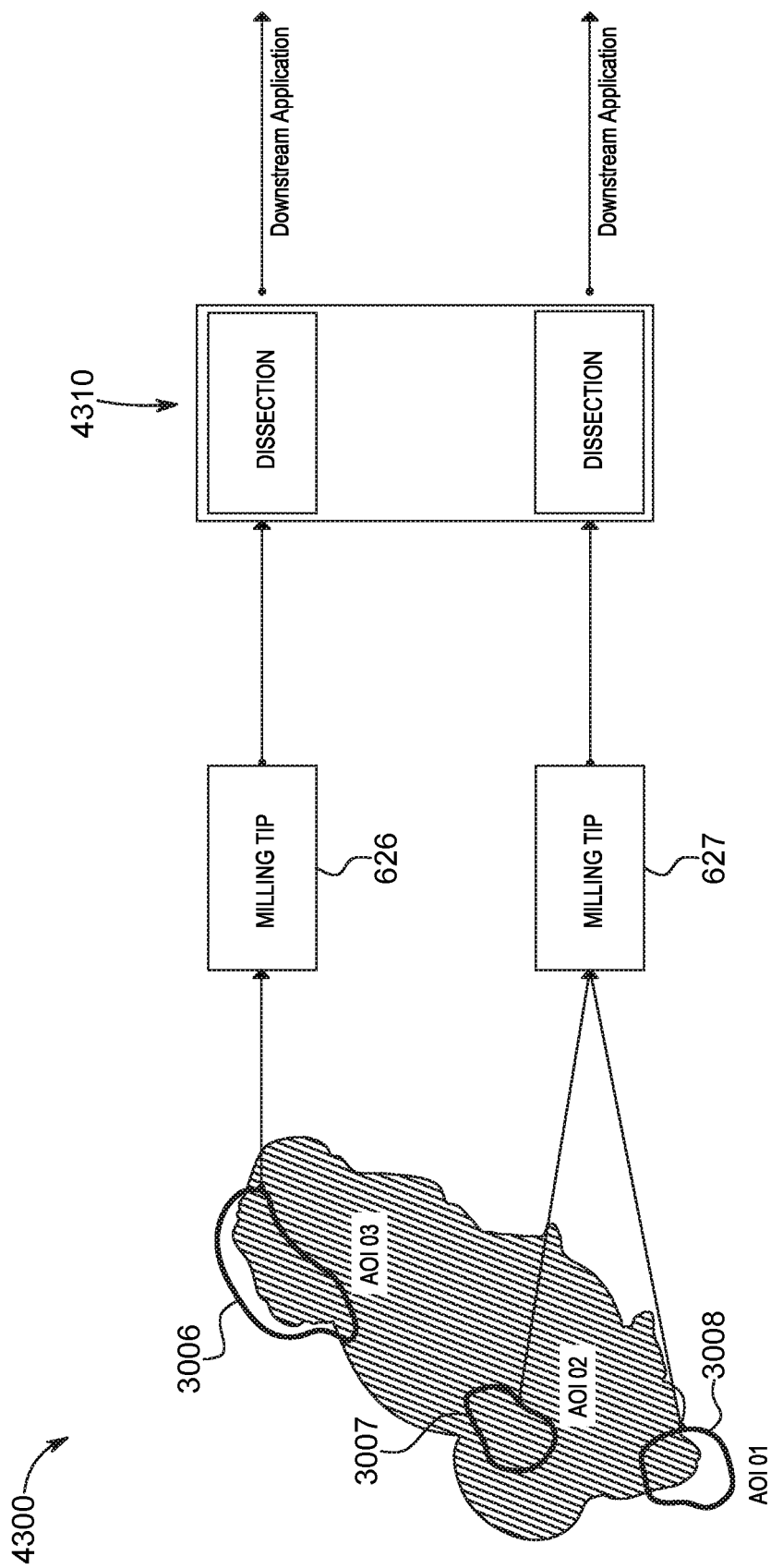
FIGS. 43, 44, 45, 46 represent screen shots of various features that are available to the user during the operation of the tissue dissection instrument, according to an exemplary embodiment of the present disclosure.
Figure 44:
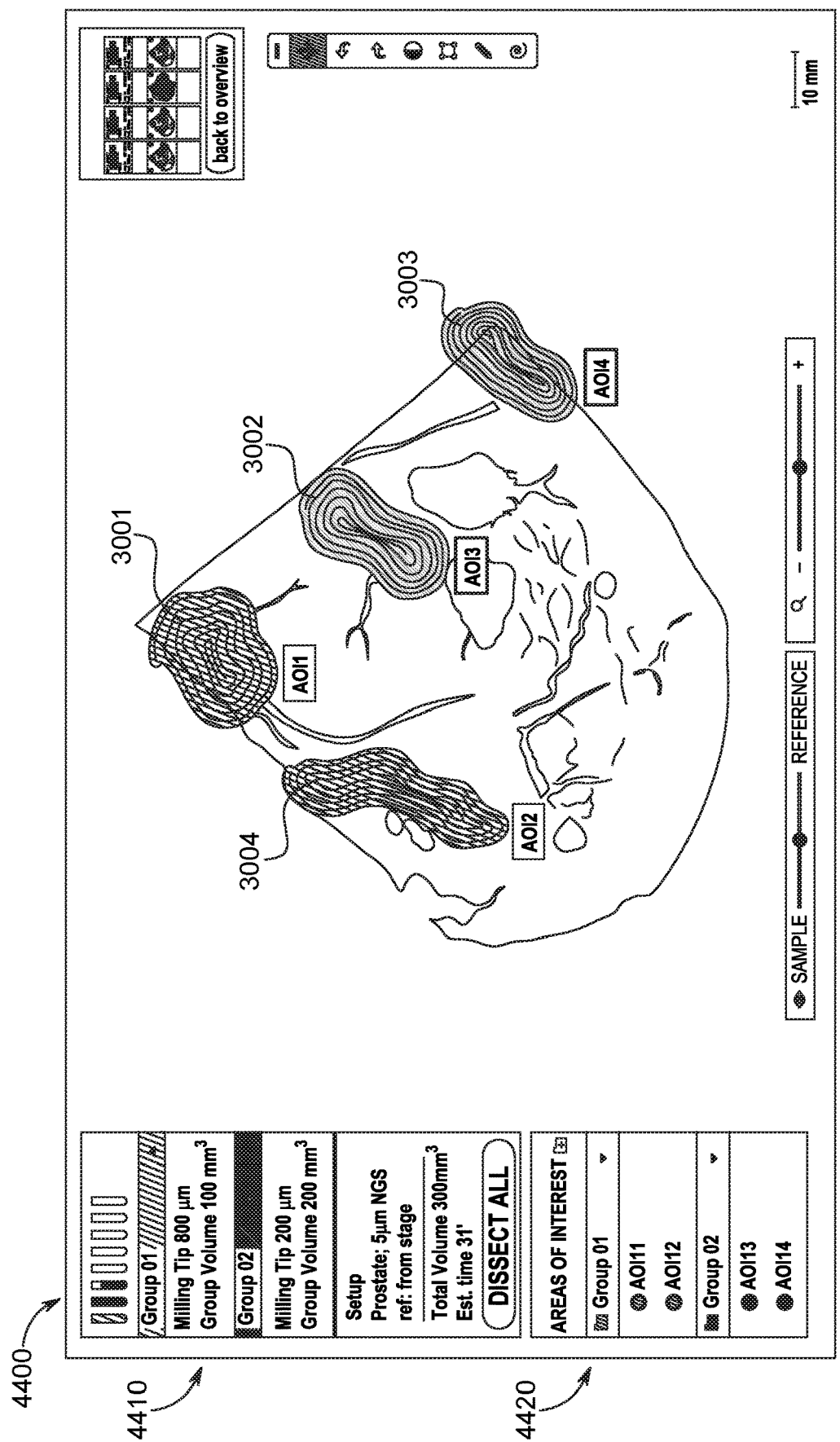

FIGS. 43, 44, 45, 46 represent screen shots 4300, 4400, 4500, 4600, respectively of various features that are available to the user during the operation of the tissue dissection instrument 100. FIGS. 43 and 44 illustrate the AOI grouping features. There could be a need to define different outputs for certain AOIs 3000. In this case it becomes crucial to be able to group the AOIs 3000 and to define different collection vials 410 for each group of AOIs 3000. In this illustration, AOI 3006 is assigned its own group (yellow color) and milling tip 626, while AOIs 3007 and 3008 are grouped together (red color) and assigned to milling tip 627. Each group of AOIs will be dissected separately in preparation for separate analysis, such as by different downstream applications. The dissection process 4310 is done in a batch. One group is dissected first, and the collected tissue is placed into a first set of collection vials, as described earlier. Then, the second group is dissected and places into a second set of second vials.

With reference to screen shot 4400, a "Dissection Info" panel 4410 is split into two color-coded groups: Group 01 that corresponds to the blue colored AOIs 3001, 3004, and Group 02 that corresponds to the green-colored AOIs 3002, 3003. The panel 4410 allows the user to define the milling tip 600 for each individual AOI. An "Area of Interest" panel 4420 is also split into the same two color-coded groups: Group 01 and Group 02. The "Area of Interest" panel 4420 allows the user to drag and drop AOIs into different groups. If a group is deleted, the AOIs return to Group 01. The grouping of the areas of interest is important for example, for assigning each group to a different biological specimen (e.g., tumor type) being excised.

Figure 45:
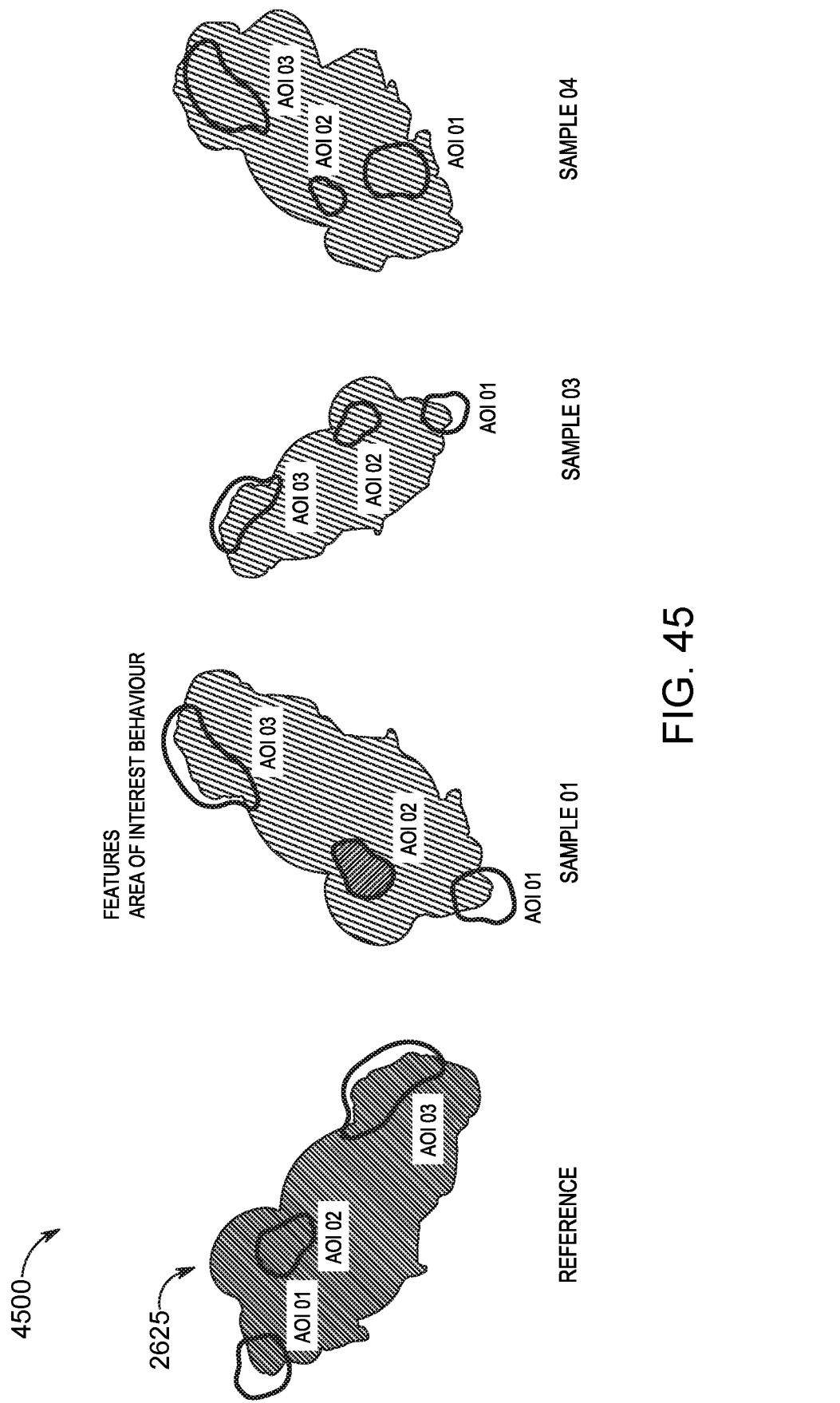

Screen shot 4500 of FIG. 45 illustrates the AOI behavior features. AOIs travel and may change along the sequential cuts. In most cases, transforming and/or warping the reference slide 2625 will suffice. However, in certain more difficult cases, it becomes important for the tissue dissection instrument 100 to allow the user to selectively edit the shapes of the AOIs in a specific sample but maintaining the same name to facilitate tracking.

Figure 46:
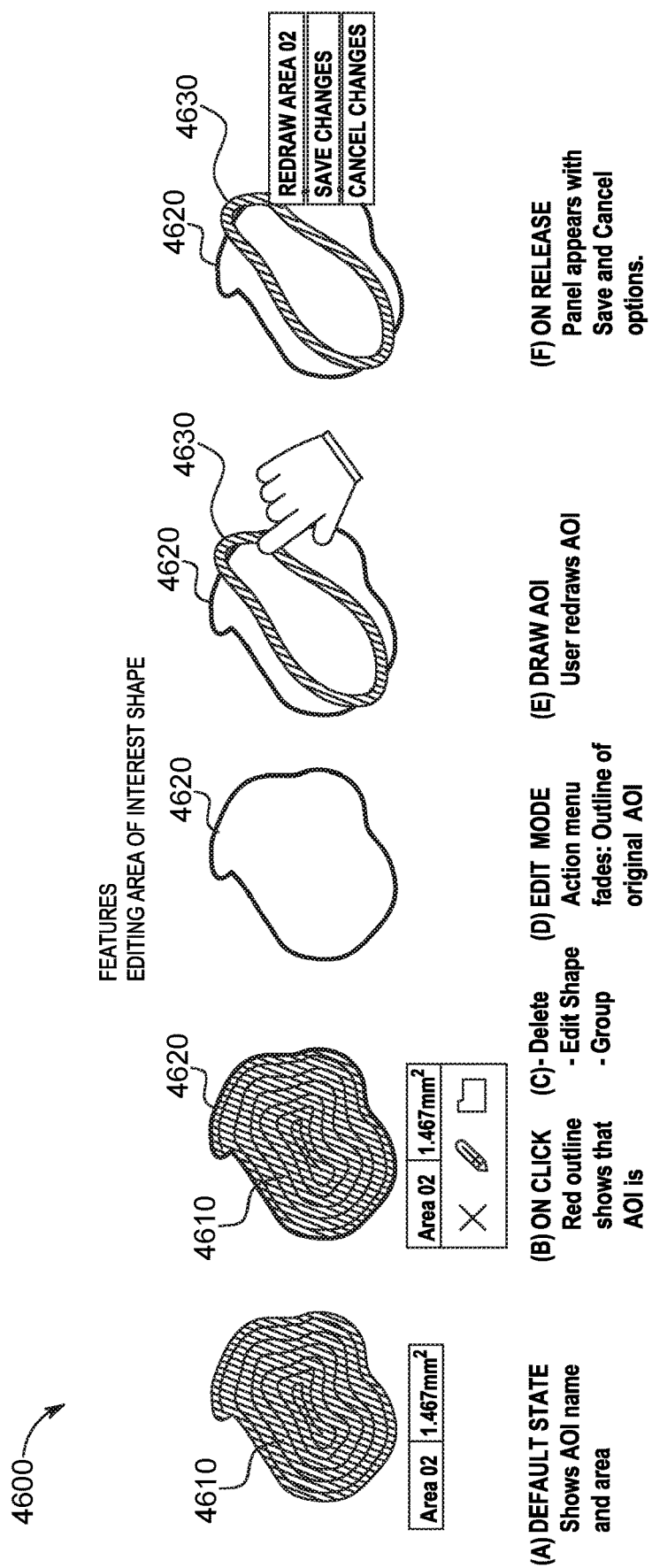

Screen shot 4600 of FIG. 46 illustrates the AOI shape editing features. In certain circumstances, it might be necessary to adjust an AOI shape because of the way it evolves through the sequential cuts. So, instead of creating unique AOIs throughout the samples, the tissue dissection instrument 100 allows the user to selectively alter the shape of an AOI 4610 in specific slides but retaining the same name.

View (A) illustrates a "Default State," which shows the AOI name and area. View (B) illustrates an "On Click State," which shows a red outline 4620 that highlights the selection of the particular AOI 4610, and provides the user with an "Action" menu: to delete, edit the shape, or group the AOI 4610. View (C) illustrates an "Edit State," that causes the "Action" menu to fade, and the outline 4620 of the original AOI 4610 to remain visible in red color. View (D) illustrates a "Draw State," which allows the user to redraw the AOI in comparison to the original AOI outline 4620. The redrawn AOI 4630 is illustrated in a different color, e.g., blue color, for ease of identification. View (F) illustrates the "On Release State," which provides the user with the options to either save or cancel the redrawn AOI 4630. If saved, the redrawn AOI 4630 will replace the original AOI 4610, assuming its grouping and color.

In each of the flow charts described herein, one or more of the methods may be embodied in a computer readable medium containing computer readable code such that a series of steps are performed when the computer readable code is executed on a computing device. In some implementations, certain steps of the methods are combined, performed simultaneously or in a different order, or perhaps omitted, without deviating from the spirit and scope of the invention. Thus, while the method steps are described and illustrated in a particular sequence, the use of a specific sequence of steps is not meant to imply any limitations on the invention. Changes may be made with regards to the sequence of steps without departing from the spirit or scope of the present invention. The use of a particular sequence is therefore, not to be taken in a limiting sense, and the scope of the present invention is defined only by the appended claims.

As it will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

As it will be further appreciated, the processes in embodiments of the present invention may be implemented using any combination of software, firmware or hardware. As a preparatory step to practicing the invention in software, the programming code (whether software or firmware) will typically be stored in one or more computer readable storage mediums for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The article of manufacture containing the programming code is used by either executing the code directly from the storage device, by copying the code from the storage device into another storage device such as a hard disk, RAM, etc., or by transmitting the code for remote execution using transmission type media such as digital and analog communication links. The methods of the invention may be practiced by combining one or more machine-readable storage devices containing the code according to the present invention with appropriate processing hardware to execute the code contained therein. An apparatus for practicing the invention could be one or more processing devices and storage systems containing or having network access to program(s) coded in accordance with the invention.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, R.F, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

In other words, the present invention provides a non-transitory computer-readable medium comprising instructions which, when executed by a processor, cause the processor to perform a plurality of operations comprising:— causing a load cell block of a fill station of an instrument to be automatically calibrated; causing an automatic tip pressure actuator of the instrument to be calibrated; obtaining user input user input indicating tissue sample type and parameters to enable determination of tissue volume to be collected; causing the instrument to import a reference image that contains annotations; prompting the user to align the reference image to a first tissue sample slide, in order to automatically replicate the aligned reference image to other loaded tissue sample slides; and initiating a dissection, by the instrument, of one or more biological specimens based on the annotations.

The instructions, when executed by the process, may further cause the processor to perform at least one of the following operations:

prompt the user to select areas of interest to be dissected;
prompt the user to selectively group the areas of interest into independent groups;
prompt the user to confirm that a fill station reservoir is loaded onto the load cell block, and to monitor a buffer solution fill status;
prompt the user to load a desired number of milling tips and a corresponding number of collection vials;
prompt the user to enter a dissection setting;
report whether sufficient buffer solution is contained within the fill station reservoir to complete a dissection run;
report whether the dissection buffer solution has been collected by the milling tips during the dissection run; and
provide a visual color-coded illustration of the loaded milling tips and collection vials.

The instructions, when executed by the process, may further cause the processor to assign a weight to be applied onto each one of the milling tips based on the inputted tissue sample type and parameters and dissection setting.

The invention claimed is:

1. An instrument for automatically dissecting a biological specimen on a slide, the instrument comprising:
   a head assembly that includes a milling tip interface;
   a base mounted onto the head assembly, wherein the base includes a milling tip holder for retaining a milling tip;
   a stage mounted onto the head assembly, above the base;
   wherein the stage includes a fill station comprising a fill station reservoir that is fillable with a buffer solution;
   wherein the head assembly is configured to automatically secure the milling tip interface to the milling tip, and to move the milling tip to the fill station for filling with a predefined volume of buffer solution; and
   wherein the filled milling tip is configured to automatically dissect the biological specimen on the slide.

2. The instrument of claim 1, further comprising a collection vial mounted on the stage; and
   wherein the head assembly is configured to move the milling tip and to dispose of the milling tip within the collection vial, upon completion of the dissection of the biological specimen.

3. The instrument of claim 1, wherein the fill station reservoir comprises a container and a reservoir riser.

4. The instrument of claim 1, wherein the reservoir riser is coupled to a load cell block.

5. The instrument of claim 1, wherein the fill station is electronically monitored.

6. The instrument of claim 1, further comprising a collection vial mounted on the stage; and
   wherein the head assembly is configured to move the milling tip and to dispose of the milling tip into the collection vial, upon completion of the dissection of the biological specimen.

7. The instrument of claim 6, wherein the head assembly further includes an automatic tip pressure actuator that is configured to regulate pressure applied by the milling tip onto the biological specimen.

8. An instrument for automatically dissecting biological specimens on a plurality of slides, the instrument comprising:
   a head assembly that includes a milling tip interface;
   a base mounted onto the head assembly, wherein the base includes a plurality of milling tip holders for retaining a corresponding number of milling tips;
   a stage mounted onto the head assembly, above the base;
   wherein the stage includes a fill station comprising a fill station reservoir that is fillable with a buffer solution;
   wherein the head assembly is configured to automatically and sequentially select each one of the milling tips, to secure the selected milling tip interface to the selected milling tip, and to move the secured milling tip to the fill station to be filled with a predefined volume of buffer solution; and
   wherein the filled milling tip is configured to automatically dissect a portion of the biological specimens on the slide.

9. The instrument of claim 8, wherein the stage includes a load cell block;
   wherein the load cell block continuously monitors the weight of the buffer solution contained within the fill station reservoir in order to monitor the volume of the buffer solution dispensed to the milling tip, and to further determine whether sufficient buffer solution is available in the fill station reservoir to complete the dissection.

10. The instrument of claim 9, wherein the head assembly includes a backdrop assembly that provides a selection of backdrops of different colors.

11. The instrument of claim 9, wherein the head assembly further includes a bar code reader configured to read slide barcodes and collection vials barcodes.

12. The instrument of claim 9, wherein the stage includes a camera that acquires images of the milling tips, the collection vials, and the slides.

13. The instrument of claim 12, wherein the acquired images of the milling tips affirm the presence and size of each milling tip;
   wherein the acquired images of the collection vials affirm the presence of each milling tip and the volume of the buffer solution contained therewithin; and
   wherein the acquired images of the slides affirm the accuracy of the dissection of areas of interest defined onto the slides.

14. The instrument of claim 13, wherein the milling tips and the collection vials are color coded for identification purpose.

15. A method of using an instrument for automatically dissecting biological specimens on a plurality of slides, the method comprising:
   mounting a base onto a head assembly that includes a milling tip interface;
   mounting a stage onto the head assembly;
   placing a plurality of milling tips into a plurality of milling tip holders on the stage;
   placing a plurality of collection vials in corresponding wells that are formed in the stage;
   wherein the stage includes a fill station comprising a fill station reservoir that is fillable with a buffer solution;
   wherein the instrument is configured to cause a processor to perform the following operations, upon receiving an instruction to initiate operation:
      to automatically and sequentially select each one of the milling tips;
      for each selected milling tip, to secure the milling tip interface to the selected milling tip, and to move the secured milling tip to the fill station to be filled with a predefined volume of buffer solution; and
      to cause the selected milling tip to dissect at least a portion of the biological specimens on one of the plurality of slides.

16. The method of claim 15, further comprising at least one of:
   verifying the presence and/or size of the selected milling tip;
   verifying the presence of a corresponding collection vial; and
   upon completion of a dissection run, verifying that the buffer solution was collected.

17. The method of claim 15, further comprising acquiring an image of an annotated reference slide that includes a plurality of areas of interest to be dissected; and
   transferring and aligning the image of the annotated reference slide to the at least some of the plurality of slides.

18. The method of claim 17, further comprising serially dissecting across multiple areas of interest at one time.

19. The method of claim 15, further comprising grouping the plurality of areas of interest into separate groups.

20. The method of claim 19, further comprising dissecting each group of the plurality of separate groups independently.

* * * * *